United States Patent
Chen et al.

(10) Patent No.: US 12,371,487 B2
(45) Date of Patent: Jul. 29, 2025

(54) METHODS FOR OBTAINING ANTIBODIES THAT BIND TRANSMEMBRANE PROTEINS AND CELLS THAT PRODUCE THE SAME

(71) Applicant: Regeneron Pharmaceuticals, Inc., Tarrytown, NY (US)

(72) Inventors: Gang Chen, Yorktown Heights, NY (US); Ergang Shi, Sleepy Hollow, NY (US); Wen-Yi Lee, New Hyde Park, NY (US); David Suh, Midland Park, NJ (US); Glen Farr, Prospect, CT (US); Robert Babb, River Edge, NJ (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 532 days.

(21) Appl. No.: 17/558,645

(22) Filed: Dec. 22, 2021

(65) Prior Publication Data

US 2022/0195038 A1    Jun. 23, 2022

Related U.S. Application Data

(60) Provisional application No. 63/130,044, filed on Dec. 23, 2020.

(51) Int. Cl.
    *C07K 16/28*    (2006.01)
    *G01N 33/68*    (2006.01)

(52) U.S. Cl.
    CPC ............. *C07K 16/28* (2013.01); *G01N 33/68* (2013.01); *C07K 2317/14* (2013.01)

(58) Field of Classification Search
    CPC ................................. A61K 40/20; A61K 40/30
    See application file for complete search history.

(56) References Cited

U.S. PATENT DOCUMENTS

| | | | |
|---|---|---|---|
| 5,589,466 | A | 12/1996 | Felgner et al. |
| 5,973,972 | A | 10/1999 | Kwon et al. |

(Continued)

FOREIGN PATENT DOCUMENTS

| | | |
|---|---|---|
| WO | 2007/003041 A1 | 1/2007 |
| WO | 2008/074895 A1 | 6/2008 |

(Continued)

OTHER PUBLICATIONS

Gardill et al. (Nanodisc technology facilitates identification of monoclonal antibodies targeting multi-pass membrane proteins, Scientific Reports vol. 10, Article No. 1130 (2020)) (Year: 2020).*

(Continued)

*Primary Examiner* — Ann Montgomery
*Assistant Examiner* — Chau N. B. Tran
(74) *Attorney, Agent, or Firm* — Scully, Scott, Murphy & Presser, P.C.

(57) ABSTRACT

Disclosed are methods for obtaining cells that express antibodies that bind transmembrane proteins, methods for generating antibodies from such cells, antibodies to transmembrane proteins and fragments thereof, and nucleic acids encoding the antibodies. More particularly, the disclosure relates to methods for obtaining antibody-producing cells that express an antibody that binds to a transmembrane protein based on the use of lipid bilayer-membrane scaffold protein complexes to present transmembrane protein antigens to cells.

39 Claims, 6 Drawing Sheets

Figure 1A:
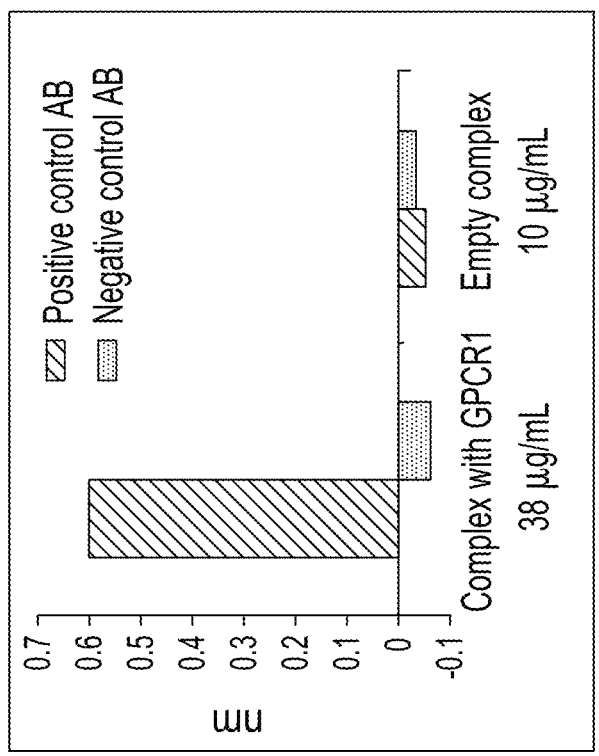

Specification includes a Sequence Listing.

(56) References Cited

U.S. PATENT DOCUMENTS

| | | | |
|---|---|---|---|
| 6,077,835 A | 6/2000 | Hanson et al. | |
| 7,662,410 B2 | 2/2010 | Sligar et al. | |
| 8,502,018 B2 | 8/2013 | Murphy et al. | |
| 8,642,835 B2 | 2/2014 | MacDonald et al. | |
| 8,697,940 B2 | 4/2014 | Macdonald et al. | |
| 8,791,323 B2 | 7/2014 | Murphy et al. | |
| 9,006,511 B2 | 4/2015 | Macdonald et al. | |
| 9,012,717 B2 | 4/2015 | Macdonald et al. | |
| 9,029,628 B2 | 5/2015 | Macdonald et al. | |
| 9,035,128 B2 | 5/2015 | MacDonald et al. | |
| 9,066,502 B2 | 6/2015 | Macdonald et al. | |
| 9,150,662 B2 | 10/2015 | Macdonald et al. | |
| 9,163,092 B2 | 10/2015 | Macdonald et al. | |
| 9,206,261 B2 | 12/2015 | Macdonald et al. | |
| 9,206,262 B2 | 12/2015 | Macdonald et al. | |
| 9,206,263 B2 | 12/2015 | Macdonald et al. | |
| 9,226,484 B2 | 1/2016 | Macdonald et al. | |
| 9,334,333 B2 | 5/2016 | Macdonald et al. | |
| 9,394,373 B2 | 7/2016 | Macdonald et al. | |
| 9,399,683 B2 | 7/2016 | Macdonald et al. | |
| 9,540,452 B2 | 1/2017 | Macdonald et al. | |
| 9,796,788 B2 | 10/2017 | McWhirter et al. | |
| 9,969,814 B2 | 5/2018 | McWhirter et al. | |
| 2006/0222654 A1 | 10/2006 | Delcayre et al. | |
| 2008/0305516 A1* | 12/2008 | Kjaergaard | C07K 16/00 435/69.6 |
| 2011/0195454 A1 | 8/2011 | McWhirter et al. | |
| 2012/0021409 A1 | 1/2012 | McWhirter et al. | |
| 2012/0192300 A1 | 7/2012 | Babb et al. | |
| 2013/0045492 A1 | 2/2013 | Babb et al. | |
| 2013/0185821 A1 | 7/2013 | Babb et al. | |
| 2013/0302836 A1 | 11/2013 | McWhirter et al. | |
| 2014/0357521 A1 | 12/2014 | Steyaert et al. | |
| 2015/0147822 A1 | 5/2015 | Marshall et al. | |
| 2016/0082125 A1 | 3/2016 | Frauenfeld | |
| 2018/0125043 A1 | 5/2018 | Guo et al. | |
| 2019/0204337 A1 | 7/2019 | Frauenfeld et al. | |

FOREIGN PATENT DOCUMENTS

| | | |
|---|---|---|
| WO | 2008/114020 A2 | 9/2008 |
| WO | 2011/097603 A1 | 8/2011 |
| WO | 2012/148873 A2 | 11/2012 |
| WO | 2013/134263 A1 | 9/2013 |
| WO | 2013/184761 A1 | 12/2013 |
| WO | 2014/145961 A2 | 9/2014 |
| WO | 2014/160179 A1 | 10/2014 |
| WO | 2014/160202 A1 | 10/2014 |
| WO | 2016/077666 A1 | 5/2016 |
| WO | 2017/214089 A1 | 12/2017 |
| WO | 2019/113065 A1 | 6/2019 |
| WO | 2019/231403 A1 | 12/2019 |
| WO | 2020/061473 A1 | 3/2020 |
| WO | 2020/061476 A1 | 3/2020 |
| WO | WO 2020/061477 A1 | 3/2020 |

OTHER PUBLICATIONS

Bhattacharya et al. (Nanodisc-Incorporated Hemagglutinin Provides Protective Immunity against Influenza Virus Infection, J Virol. Jan. 2010; 84(1): 361-371) (Year: 2010).*

Pedrioli et al. (Single B cell technologies for monoclonal antibody discovery, Trends in Immunology, Dec. 2021, vol. 42, No. 12) (Year: 2021).*

Boonyaratanakornkit and Taylor (Antigen-Specific B Cell Responses, Frontiers in Immunology, Jul. 2019) (Year: 2019).*

Trier et al. (Peptide antibodies in Clinical laboratory diagnostics, Advances in Clinical Chemistry, 2017) (Year: 2017).*

Gardill B. et al., "Nanodisc Technology Facilitates Identification of Monoclonal Antibodies Targeting Multi-Pass Membrane Proteins", Scientific Reports 10(1):DOI: 10.1038 (Jan. 24, 2020).

International Search Report and Written Opinion of the International Searching Authority dated May 6, 2022 received in International Application No. PCT/US2021/064769.

Alberts B. et al., "Programmed Cell Death (Apoptosis)", Molecular Biology of the Cell, 4th Edition (2002).

Flores-Romero H. et al., "Pore Formation in Regulated Cell Death", The EMBO Journal 39:e105753 (2020).

Hensel J.A. et al., "Characterization of Immune Cell Subtypes in Three Commonly Used Mouse Strains Reveals Gender and Strain-Specific Variations", Laboratory Investigation 99:93-106 (2019).

Lei L. et al., Antigen-Specific Single B Cell Sorting and Monoclonal Antibody Cloning in Guinea Pigs, Frontiers in Microbiology 10:672 (Apr. 2019).

Li H. et al., "Characterization of Spleen and Lymph Node Cell Types Via CITE-Seq and Machine Learning Methods", Frontiers in Molecular Neuroscience 15:1033159 (2022).

Medina CB et al., "Do Not Let Death Do Us Part: 'Find-Me' Signals in Communication Between Dying Cells and the Phagocytes", Cell Death and Differentiation 23:979-989 (2016).

Pedrioli A. et al., "Single B Cell Technologies for Monoclonal Antibody Discovery", Trends in Immunology 42(12):1143-1158 (Dec. 2021).

NCBI Reference Sequence No. XP_010980763.1 (2 pages) (Jan. 7, 2015).

NCBI Reference Sequence No. XP_010980767.1 (2 pages) (Jan. 7, 2015).

NCBI Reference Sequence No. XP_014588001.1 (2 pages) (Jan. 23, 2018).

NCBI Reference Sequence No. XP_014948870.1 (2 pages) (Dec. 17, 2015).

NCBI Reference Sequence No. XP_014965766.1 (2 pages) (Dec. 21, 2015).

NCBI Reference Sequence No. XP_016804947.1 (2 pages) (Jun. 2, 2016).

NCBI Reference Sequence No. XP_022270547.1 (2 pages) (Sep. 5, 2017).

Bayburt T.H. et al., "Self-Assembly of Discoidal Phospholipid Bilayer Nanoparticles With Membrane Scaffold Proteins", Nano Letters 2(8):853-856 (2002).

Bayburt T.H. et al., "Assembly of Single Bacteriorhodopsin Trimers in Bilayer Nanodiscs", Archives of Biochemistry and Biophysics 450:215-222 (2006).

Denisov I.G. et al., "Nanodiscs in Membrane Biochemistry and Biophysics", Chem. Rev. 117(6):4669-4713 (Mar. 22, 2017).

Foord S.M. et al., "International Union of Pharmacology. XLVI. G Protein-Coupled Receptor List", Pharmacological Reviews 57(2):279-288 (2005).

Flayhan A. et al., "Saposin Lipid Nanoparticles: A Highly Versatile and Modular Tool for Membrane Protein Research", Structure 236:345-355 (Feb. 2018).

Frauenfeld J. et al., "Making the Undruggable Druggable", Salipro Biotech (26 pages) (Dec. 2020).

Grant A. et al., "Expression and Secretion Vectors for Yeast", Methods in Enzymology 153:516-544 (1987).

Inagaki S. et al., "Biophysical Characterization of Membrane Proteins in Nanodiscs", Methods 59(3):287-300 (Mar. 1, 2013).

Jaakola V-P et al., "The 2.6 A Crystal Structure of a Human A2A Adenosine Receptor Bound to an Antagonist", Science 322(5905):1211-1217 (Nov. 21, 2008).

Jakobovits A. et al., "Production of Antigen-Specific Human Antibodies from Mice Engineered With Human Heavy and Light Chain YACsa", Ann. NY Acad. Sci. 764:525-535 (1995).

Lightwood D.J. et al., "Antibody Generation Through B Cell Panning on Antigen Followed by In Situ Culture and Direct RT-PCR on Cells Harvested En Masse From Antigen-Positive Wells", Journal of Immunological Methods 316:133-143 (2006).

Lin L. et al., "SLC Transporters as Therapeutic Targets: Emerging Opportunities", Nat Rev Drug Discov. 14(8):543-560 (Aug. 2015).

Loving R., "Discovery of Novel Therapeutics Against GPCRs, Ion Channels & Transporters", Salipro Biotech Poster, (2022).

Margulies D.H. et al., "Chapter 2—Induction of Immune Response", Current Protocols in Immunology, Supplement 89(1):2.0.1-2.0.3 (Apr. 2010).

(56) References Cited

OTHER PUBLICATIONS

Mendez M.J. et al., "Functional Transplant of Megabase Human Immunoglobulin Loci Recapitulates Human Antibody Response in Mice", Nature Genetics 15:146-156 (Feb. 1997).
Rolink A. et al., "A Subpopulation of B220+ Cells in Murine Bone Marrow Does Not Express CD19 and Contains Natural Killer Cell Progenitors", J. Exp. Med. 183:187-194 (Jan. 1996).
Rouck J. et al., "Recent Advances in Nanodisc Technology for Membrane Proteins Studies", FEBS Lett. 591(14):2057-2088 (Jul. 2017).
Santos R. et al., "A Comprehensive Map of Molecular Drug Targets", Nat Rev Drug Discov. 16(1):19-34 (Jan. 2017).
Schuler M.A. et al., "Nanodiscs as a New Tool to Examine Lipid-Protein Interactions", Methods Mol Biol. 974:415-433 (2013).
Sykes K.F. et al., "Linear Expression Elements: a Rapid, In Vivo, Method to Screen for Gene Functions", Nature Biotechnology 17:355-359 (Apr. 1999).
Van Der Heyde H.C. et al., "Analysis of Antigen-Specific Antibodies and Their Isotypes in Experimental Malaria", Cytometry Part A 71A:242-250 (2007).
Wang X. et al., "Human Immunoglobulin Variable Region Gene Analysis by Single Cell RT-PCR", Journal of Immunological Methods 244:217-225 (2000).
NCBI Reference Sequence No. NP_001092768.1 (8 pages) (Mar. 6, 2022).
NCBI Reference Sequence No. NP_001104257.2 (3 pages) (May 14, 2018).
NCBI Reference Sequence No. NP_001137581.1 (2 pages) (Jul. 3, 2020).
NCBI Reference Sequence No. NP_001280210.1 (3 pages) (Mar. 9, 2022).
NCBI Reference Sequence No. NP_001280211.1 (3 pages) (Dec. 1, 2021).
UniProtKB/Swiss-Prot No. O08562.1 (8 pages) (Feb. 23, 2022).
UniProtKB/Swiss-Prot No. P04775.1 (12 pages) (Feb. 23, 2022).
UniProtKB/Swiss-Prot No. P35498.2 (49 pages) (Feb. 23, 2022).
UniProtKB/Swiss-Prot No. P35499.4 (26 pages) (Feb. 23, 2022).
UniProtKB/Swiss-Prot No. Q9NY46.2 (12 pages) (Feb. 23, 2022).
UniProtKB/Swiss-Prot No. Q9UI33.2 (10 pages) (Feb. 23, 2022).
UniProtKB/Swiss-Prot No. Q9UQD0.1 (17 pages) (Feb. 23, 2022).
UniProtKB/Swiss-Prot No. Q9Y5Y9.2 (9 pages) (Feb. 23, 2022).
UniProtKB/Swiss-Prot No. Q14524.2 (58 pages) (Feb. 23, 2022).
UniProtKB/Swiss-Prot No. Q15858.3 (22 pages) (Feb. 23, 2022).
UniProtKB/Swiss-Prot No. Q28644.1 (7 pages) (Feb. 23, 2022).
UniProtKB/Swiss-Prot No. Q62205.2 (8 pages) (Feb. 23, 2022).
UniProtKB/Swiss-Prot No. Q99250.3 (32 pages) (Feb. 23, 2022).
NCBI Reference Sequence No. XP_001100368.1 (2 pages) (Apr. 26, 2019).
NCBI Reference Sequence No. XP_001496473.1 (2 pages) (Nov. 20, 2015).
NCBI Reference Sequence No. XP_003820970.1 (2 pages) (Jun. 5, 2020).
NCBI Reference Sequence No. XP_004004679.1 (2 pages) (Dec. 17, 2015).
NCBI Reference Sequence No. XP_004267302.1 (2 pages) (Apr. 15, 2020).
NCBI Reference Sequence No. XP_004283641.1 (2 pages) (Apr. 15, 2020).
NCBI Reference Sequence No. XP_007056690.1 (2 pages) (Jan. 23, 2019).
NCBI Reference Sequence No. XP_008256915.1 (3 pages) (Jun. 23, 2016).
NCBI Reference Sequence No. XP_008582720.1 (2 pages) (Jul. 22, 2014).
NCBI Reference Sequence No. XP_008588371.1 (2 pages) (Jul. 22, 2014).
European Office Action dated Mar. 14, 2025 received in European Application No. 21 847 855.0.

\* cited by examiner

METHODS FOR OBTAINING ANTIBODIES THAT BIND TRANSMEMBRANE PROTEINS AND CELLS THAT PRODUCE THE SAME

CROSS REFERENCE TO RELATED APPLICATION

This application claims the benefit of priority from U.S. Provisional Application No. 63/130,044, filed Dec. 23, 2020, the entire contents of which are incorporated herein by reference.

INCORPORATION BY REFERENCE OF SEQUENCE LISTING

The Sequence Listing in the ASCII text file, named as 36526_10465US01_SequenceListing.txt of 30 KB, created on Dec. 7, 2021, and submitted to the United States Patent and Trademark Office via EFS-Web, is incorporated herein by reference.

TECHNICAL FIELD

This disclosure generally relates to cells expressing antibodies that bind transmembrane proteins, methods for generating the same, antibodies to transmembrane proteins and fragments thereof, and nucleic acids encoding antibodies. More particularly, the disclosure relates to methods for obtaining antibody-producing cells that express an antibody that binds to a transmembrane protein based on use of lipid bilayer-membrane scaffold protein complexes to present transmembrane protein antigens to cells.

BACKGROUND

Transmembrane proteins, such as G-protein coupled receptors (GPCRs) and ion channels are the targets of nearly half of all FDA-approved small-molecule drugs, but very few antibodies have been approved for therapy thus far. See Santo, et al., *Nat. Rev. Drug Disc.* 16:19 (2017). Typically, methods utilized for screening antibodies or antibody-producing cells have been inefficient or unable to obtain antibodies that bind transmembrane proteins. For example, isolating and packaging multispan transmembrane proteins into carriers, such as in exosomes, virus-like particles, and proteoliposomes leave uncertainty as to whether sufficient amounts of biologically active proteins or conformationally accurate transmembrane proteins are present. Furthermore, GPCR-expressing cells have not been very successful as screening reagents, and small peptides derived from membrane-spanning transmembrane proteins are rarely successful in obtaining relevant antibodies due to their lack of conformational context. As such, new methods for obtaining and generating antibody to transmembrane proteins are needed.

SUMMARY OF THE DISCLOSURE

Disclosed herein are methods for obtaining antibodies to transmembrane proteins, which utilize lipid bilayer-membrane scaffold protein complexes to present transmembrane protein antigens to antibodies. The methods employ complexes that include a transmembrane protein of interest, as well as lipids and membrane scaffold proteins commonly found in membranes of naturally occurring cells, to present the transmembrane protein in its natural conformation to an antibody. As such, lipid bilayer-membrane scaffold protein complexes are used in the disclosed methods to identify and collect from a population of antibodies (or cells that express antibody) a particular subset of antibodies (or cells that express antibody) that bind to an epitope on a transmembrane protein that is accessible in nature, such as, for example, an extracellular domain or portions thereof. Therefore, the present methods bypass the need for time-consuming screening, identification and selection of epitope-specific antibodies by site-directed mutagenesis, and other known techniques, in order to ascertain whether or not a particular antibody recognizes a desired portion of a transmembrane protein of interest.

In one aspect, a method for obtaining antibodies or a population of cells that express antibody to a transmembrane protein of interest is provided that includes contacting a population of antibody-producing cells with a lipid bilayer-membrane scaffold protein complex that presents a transmembrane protein of interest or a portion thereof.

In some embodiments, the method includes contacting a population of antibody-producing cells with a lipid bilayer-membrane scaffold protein complex encompassing a transmembrane protein of interest or portion thereof to permit binding between the transmembrane protein antigen presented by the complex and an antibody on the surface of a cell and collecting bound antibody-producing cells.

In some embodiments, the population of antibody producing cells is a homogeneous population of cells made up of cells from one particular type of tissue, organ, or cell. In other embodiments, the population of antibody producing cells is a heterogeneous population of cells made up of cells from more than one type of tissue, organ, or cell. In certain embodiments, the population of antibody-producing cells includes tissue-derived cells from one or more of the spleen, lymph node, bone marrow, or other organ. In some embodiments, the population of antibody-producing cells includes lymphocytes. In particular embodiments, the population of antibody-producing cells includes blood cells. In certain embodiments, the population of antibody-producing cells includes peripheral blood cells, B cells, plasma cells, plasma cell myelomas, or a combination thereof. In specific embodiments, the population of antibody-producing cells is a population of B cells. In one embodiment, the population of antibody-producing cells is comprised of memory B cells. In one embodiment, the population of antibody-producing cells includes recombinant cells such as, for example, hybridomas.

In some embodiments, the methods include obtaining a population of antibody-producing cells from an animal. In certain embodiments, the population of antibody-producing cells is obtained from an animal that produces antibodies against a transmembrane protein of interest after immunization with a transmembrane protein of interest or nucleic acid immunogen that encodes the same. In certain embodiments, the animal or immunized animal is a mammal. In some embodiments, the mammal is a mouse, rat, goat, human, hamster, pig, monkey or guinea pig. In some embodiments, the mammal is not a human. In particular embodiments, the non-human mammal is a mouse, rat or goat. In specific embodiments, the mammal is a mouse. In another embodiment of the methods, the mammal is a human such as, for example, a human that has been exposed to an immunogen.

In some instances, the animal is immunized. In certain embodiments, the immunized animal is genetically-engineered. For example, the animal can be genetically-engineered such that the animal does not express a transmembrane protein of interest from an endogenous gene locus. In certain embodiments, the genetically-engineered animal is a non-human mammal such as, for example, a mouse, goat or rat, that includes a nucleic acid sequence encoding human immunoglobulin heavy chain (IgH) and human immunoglobulin light chain (IgL) variable regions. In some embodiments, the genetically-engineered animal includes a nucleic acid sequence encoding a human immunoglobulin heavy chain and a human immunoglobulin light chain variable region and also lacks the endogenous gene encoding a transmembrane protein of interest. In specific embodiments, the immunized, genetically-engineered animal is a mouse or rat such as, for example, a VELOCIMMUNE® mouse that includes a humanized IgH locus and/or a humanized Igκ light chain locus. In some embodiments, the immunized, genetically-engineered animal is a mouse that includes a humanized IgH locus and a humanized Igκ light chain locus, which lacks the endogenous mouse gene encoding a transmembrane protein of interest. In one embodiment, a genetically-engineered mouse comprising DNA encoding human immunoglobulin heavy and immunoglobulin lambda light chain (Igλ) variable regions. In a particular embodiment, the genetically-engineered mouse comprises DNA encoding human immunoglobulin heavy and immunoglobulin lambda light chain (Igλ) variable regions, and also lacks the endogenous mouse gene encoding a transmembrane protein of interest.

In some embodiments, the antibody-producing cells are obtained from an animal immunized with a transmembrane protein of interest immunogen. In certain embodiments, the animal has been immunized with a nucleic acid encoding at least a portion of the transmembrane protein of interest, or with at least a portion of the transmembrane protein of interest. In some embodiment, the animal has been immunized with a nucleic acid encoding the full-length transmembrane protein of interest. In other embodiments, the animal has been immunized with a nucleic acid encoding a portion of the transmembrane protein of interest. In specific embodiments, the nucleic acid does not encode for the amino-terminus and/or carboxy-terminal portion of the full-length transmembrane protein of interest. In other embodiments, the animal has been immunized with a nucleic acid encoding a transmembrane protein of interest or a portion thereof that is encompassed in a carrier capable of expressing the nucleic acid, such as for example, a plasmid, an expression vector, a virus-like particle (VLP), a cell, an exosome and a liposome. In some embodiments, the animal has been immunized with a transmembrane protein of interest or a portion thereof. In certain embodiments, the animal has been immunized with a full-length transmembrane protein of interest. In specific embodiments, the transmembrane protein of interest immunogen is truncated, and does not include the amino-terminus and/or carboxy-terminal portion of the full-length transmembrane protein of interest. In certain embodiments, the transmembrane protein of interest or nucleic acid immunogen is modified to include one or more detectable elements, such as a label, marker or feature. In some embodiments, the immunogen comprises a detectable label. In specific embodiments, the detectable label is a FLAG-tag, histidine tag (His-tag), Avi-tag, BirA-tag or a combination thereof. In some embodiments, the transmembrane protein of interest immunogen has a FLAG-tag and a His-tag. In particular embodiments, the detectable label or labels are located at the amino-terminus or carboxy-terminus of the immunogen. In specific embodiments, the animal has been immunized with a transmembrane protein of interest or portion thereof that is encompassed in a lipid bilayer-membrane scaffold protein complex.

In certain embodiments, the animal is immunized with a nucleotide sequence encoding a chimeric transmembrane protein of interest comprising a portion of a human transmembrane protein of interest that is operably linked to a portion of a non-human homolog of the transmembrane protein of interest. The non-human homolog can be from, for example, a human, chimpanzee, rhesus monkey, rabbit, horse, sheep, rat, mouse, dog, chicken or goat. In certain embodiments, the nucleotide sequence encoding a chimeric transmembrane protein of interest also includes a nucleotide sequence that encodes a detectable element such as, for example, a His-tag, FLAG-tag, Avi-tag or Bir-A-tag. In other embodiments, the animal is immunized with a chimeric transmembrane protein of interest or a portion thereof, which includes a portion of a human transmembrane protein of interest that is operably linked to a portion of a non-human homolog of the transmembrane protein of interest. In one embodiment, the chimeric transmembrane protein of interest includes a detectable element such as, for example, a His-tag, FLAG-tag, Avi-tag or Bir-A-tag.

In some instances, an animal is immunized with two or more immunogens such as, for example, a protein or peptide, a nucleic acid sequence such as DNA or RNA, a modified protein or encoding DNA, a VLP and a lipid bilayer-membrane scaffold protein complex encompassing a transmembrane protein of interest or portion thereof.

The methods include contacting a population of antibody-producing cells with a lipid bilayer-membrane scaffold protein complex encompassing a transmembrane protein of interest, or a portion thereof to obtain a population of antibody-producing cells that express antibody that binds to the transmembrane protein of interest.

The lipid bilayer-membrane scaffold protein complex includes at least one membrane scaffold protein (MSP) and lipids. In some embodiments, the lipid bilayer-membrane scaffold protein complex includes at least one MSP and a plurality of lipids. In certain embodiments, the lipid bilayer-membrane scaffold protein complex includes at least two or exactly two MSPs. In other embodiments, the lipid bilayer-membrane scaffold protein complex includes three or more MSPs. In some instances, the lipid bilayer-membrane scaffold protein includes at least one membrane scaffold protein such as MSP1E3D1, MSP1D1, MSP2N3 and MSP2N2. In one embodiment, the lipid bilayer-membrane scaffold protein complex comprises two MSP1E3D1 proteins. In some embodiments, the MSPs are the same. In other embodiments, the MSPs in the lipid bilayer-membrane scaffold protein complex are different.

In some embodiments, the lipid bilayer-membrane scaffold protein complex contains at least one labeled MSP that includes a detectable element, such as a label, marker or feature. In specific embodiments, the lipid bilayer-membrane scaffold protein complex contains two labeled MSPs and a lipid bilayer. In some embodiments, the MSP protein comprises a detectable label such as a fluorophore. In specific embodiments, the detectable element is a BirA-tag or Avi-tag located on one or more of the MSPs of the complex. In exemplary embodiments, one or more of the MSPs are biotinylated, by chemically biotinylating the MSP or by genetically introducing an Avi-tag into the MSP coding sequence.

The lipid bilayer-membrane scaffold protein complex also includes a plurality of lipids, such as sphingolipids and/or phospholipids. The lipid bilayer of the complex can be comprised of a single type of lipid or multiple types of lipids. In some embodiments, the lipid bilayer-membrane scaffold protein complex includes lipids that form a disc-shaped "discoidal" phospholipid bilayer around the membrane scaffold protein(s). In certain embodiments, the lipid bilayer is comprised of one or more of the following lipids: sphingomyelin, phosphatidylcholine, and derivatives thereof. In a specific embodiment, the lipid bilayer is comprised of 1-dioleoyl phosphatidylcholine (DOPC), 1-palmitoyl 2-oleoyl phosphatidylcholine (POPC), 1-stearoyl-2-oleoyl-phosphatidylcholine (SOPC), phosphatidylethanolamines (PE), and phosphatidylserine (PS), and phosphatidylinositol (PI) or combinations thereof. In an exemplary embodiment, the lipid bilayer includes a plurality of POPC phospholipids.

The lipid bilayer-membrane scaffold protein complex for use in the methods also includes at least one transmembrane protein of interest or a portion thereof, which is presented to a population of cells by the complex as an antigen capable of binding to antibodies generated by antibody-producing cells. The transmembrane protein of interest presented by the complex can be a naturally occurring protein with at least one extracellular domain and at least one transmembrane domain. In some embodiments, the transmembrane protein of interest presented by the complex is a human protein. In other embodiments, the transmembrane protein of interest is a non-human protein, such as a mouse, rat, primate, hamster, bacterial, viral protein or the like. In certain embodiments, the transmembrane protein of interest is modified from its naturally occurring form. Exemplary modified transmembrane proteins of interest can include one or more of the following alterations to their native amino acid sequence: amino acid substitutions, amino acid deletions, amino acid insertions. In one embodiment, the transmembrane protein of interest is modified to delete, i.e., "truncate", a portion of the transmembrane protein such as, for example, the N-terminal and/or C-terminal domain of the full-length protein. In some embodiments, the transmembrane protein of interest incorporated in the lipid bilayer-membrane scaffold protein complex includes stabilizing mutations in the amino-terminus, one or more extracellular loop domains, one or more of the transmembrane domains, one or more intracellular domains, the C-terminus or a combination thereof. In one embodiment, the transmembrane protein of interest is a ligand-activated protein, whereby the transmembrane protein of interest changes conformation in the presence or absence of ligand (i.e., having an active and inactive state). In another embodiment, the transmembrane protein of interest incorporated in the lipid bilayer-membrane scaffold protein complex is a chimeric protein, which includes a portion of a human transmembrane protein of interest that is operably linked to a portion of a non-human homolog of the transmembrane protein of interest. In certain embodiments, the transmembrane protein of interest includes a detectable element such as, for example, a His-tag, FLAG-tag, Avi-tag, Bir-A tag or a combination thereof. In particular embodiments, the transmembrane protein of interest presented by the complex includes a His-tag and FLAG-tag.

In certain instances, the transmembrane protein of interest is a GPCR protein, tetraspanin protein, or an ion channel protein. In some embodiments, the transmembrane protein of interest is a GPCR protein such as, for example, CCR5, ADORA2A, ADRB3, C3AR1, ADRA2A, GLP1R, CCR4, CCR8 and CXCR4. In some embodiments, the transmembrane protein of interest is CCR5 or a portion thereof. In some embodiments, the transmembrane protein of interest is ADRA2A or a portion thereof. In certain embodiments, the transmembrane protein of interest is ADORA2A or a portion thereof. In some embodiments, the transmembrane protein of interest is C3AR1 or a portion thereof.

In some embodiments, the transmembrane protein of interest is a tetraspanin such as, for example, TSPAN 1 through TSPAN19, TSPAN21, TSPAN23, TSPAN 31, TSPAN 32, TSPAN 33, UPK1B, PRPH2, CD151, CD53, CD37, CD82, CD63, CD81, CD9, CD82, CD63, CLND6 and CLND9. In some embodiments, the transmembrane protein of interest is CD63 or a portion thereof. In other embodiments, the transmembrane protein of interest is an ion channel protein such as, for example, a voltage gated ion channel protein. In specific embodiments, the voltage-gated ion channel protein is a voltage-dependent calcium channel or a voltage gated potassium channel protein. In some embodiments, the ion channel protein is a calcium-activated potassium channel protein, a sodium channel protein, a calcium channel protein or a chloride channel. In particular embodiments of the methods, the transmembrane protein of interest is an ion channel protein such as, for example, BKCa, MaxiK, Sk, NaV1, CACNG1, CAV, CIC, or a transient receptor potential channel protein (TRP). In some embodiments, the transmembrane protein of interest is a NaV1 protein or a portion thereof. In specific embodiments, the transmembrane protein of interest is a NaV1.7 protein or a portion thereof. In some embodiments, the transmembrane protein of interest is a CACNG1 protein or a portion thereof.

In certain embodiments of the methods, the transmembrane protein of interest presented by the complex binds to an antibody on the cell surface of an antibody-producing cell. In some embodiments, the antibody binds to an epitope (binding domain present on a transmembrane protein of interest) located on a particular domain of the transmembrane protein of interest such as, for example, an extracellular domain of the transmembrane protein of interest. In specific embodiments, the antibody binds to an epitope located on an extracellular portion of the N-terminal domain of the transmembrane protein of interest. In some embodiments, the antibody binds to an epitope located on an extracellular loop of the transmembrane protein of interest or an extracellular portion of a C-terminal domain of the transmembrane protein of interest. In certain embodiments, the antibody binds to an epitope located on the C-terminal domain of the transmembrane protein of interest. In some embodiments, the antibody binds to an epitope located on an extracellular loop of the transmembrane protein of interest. In some embodiments, the antibody binds to an epitope located on an intracellular domain of the transmembrane protein of interest.

The methods can also include contacting a population of antibody-producing cells with a detectable element that binds to a cell-surface protein or biomarker of interest. For example, a heterogeneous population of antibody-producing cells obtained from an immunized animal may be contacted with a fluorescently-labeled antibody that binds to a B cell surface protein such as for example, IgG. A subset of antibody-producing cells B cells can then be obtained from the population by detecting binding between the antibody and B cells and isolating the bound cells from the population. In certain embodiments, the population of antibody-producing cells can be contacted with the fluorescently-labeled antibody that binds to a B cell surface protein at the same time the cells are contacted with a lipid bilayer-membrane scaffold protein complex containing a transmembrane protein of interest, or the cells may be contacted at different times.

In certain embodiments, the methods can also include contacting a population of antibody-producing cells with a blocking agent. For example, a population of antibody-producing cells can be contacted with a molecule, such as a peptide or compound that recognizes or binds to a portion of a transmembrane protein of interest, a portion of an MSP protein, or a detectable marker such as a His-tag or FLAG-tag. In such embodiments, the antibody-producing cells are incubated with one or more blocking agents in order to permit binding between the blocking agent(s) and antibody produced by the antibody-producing cells, which bind an epitope located on the blocking agent.

The methods can also include washing a population of cells, such as antibody-producing cells, for a period of time that removes unbound materials or cells from the bound cells.

Binding between antibody generated by antibody-producing cells and binding domains (epitopes) present on a transmembrane protein of interest presented by a lipid bilayer-membrane scaffold protein complex can be detected, and the antibody-producing cells bound to the transmembrane protein can be collected. For example, in some embodiments, binding is detected by a conformational change of the transmembrane protein of interest, activation or deactivation of the transmembrane protein of interest in a cell, or by use of one or more detectable markers. In certain embodiments, antibody-producing cells presenting antibodies bound to a transmembrane protein antigen of interest can be detected and isolated from other antibody-producing cells in a population using high-throughput techniques for single-cell isolation, such as fluorescence-activated cell sorting (FACS). In one embodiment, FACS is used to identify and isolate single antibody-producing cells that have bound to a transmembrane protein of interest lipid presented by a lipid bilayer-membrane scaffold protein complex by detecting a signal emitted by a detectable label affixed to the complex or transmembrane protein of interest encompassed therein. In specific embodiments, the signal is emitted by one or more of the following detectable labels: a biotin/streptavidin-PE complex or a fluorescent molecule.

The methods can also include obtaining or isolating antibodies or antibody-coding nucleic acids from antibody-producing cells.

In certain embodiments, a nucleic acid encoding an antibody (e.g., a gene) or a portion thereof is isolated from antibody-producing cells. In some embodiments, the nucleic acid encodes a variable domain of an antibody. In certain embodiments, the nucleic acid encodes an antibody heavy chain or a fragment thereof. In other embodiments, the nucleic acid encodes an antibody light chain or a fragment thereof. In certain instances, the nucleic acid isolated from antibody-producing cell encodes a full-length antibody. In some embodiments, the method includes isolating from an antibody-producing cell, a nucleic acid comprising a nucleotide sequence encoding the heavy chain variable region of the antibody expressed by the cell, and a nucleic acid comprising a nucleotide sequence encoding the light chain variable region of the antibody expressed by the cell.

In certain embodiments of the methods a nucleic acid encoding an antibody is expressed in a host cell. In some embodiments, host cells comprising the nucleic acid are cultured under conditions that express a full-length antibody, and the antibody can then be produced and isolated for further use. In certain embodiments, the host cell comprises a nucleic acid that encodes a variable domain of an antibody, and the cell is cultured under conditions that express the variable domain. In some embodiments, the host cell comprises a nucleic acid that encodes a variable heavy chain ($V_H$) domain of an antibody, and the cell is cultured under conditions that express the $V_H$ domain. In some embodiments, the host cell comprises a nucleic acid that encodes a variable light chain ($V_L$) domain of an antibody, and the cell is cultured under conditions that express the $V_L$ domain. In specific embodiments, the host cell comprises a nucleic acid that encodes a $V_H$ domain of an antibody and a nucleic acid that encodes a $V_L$ domain of an antibody, and the cell is cultured under conditions that express the $V_H$ domain and the $V_L$ domain.

Therefore, in one aspect of the disclosure, cells that include a nucleic acid molecule encoding an antibody specific to a transmembrane protein of interest isolated using the methods of the present disclosure are provided. In some embodiments, a cell is provided that comprises a nucleic acid that encodes a variable heavy chain ($V_H$) domain of an antibody specific to a transmembrane protein of interest. In some embodiments, a cell is provided that comprises a nucleic acid that encodes a variable light chain ($V_L$) domain of an antibody specific to a transmembrane protein of interest. In some embodiments, a cell is provided that comprises a nucleic acid that encodes a $V_H$ domain of an antibody specific to a transmembrane protein of interest and a nucleic acid that encodes a $V_L$ domain of the antibody. In some embodiments, the cell is a eukaryotic cell. In certain embodiments, the cell is a mammalian cell. In one embodiment, the cell can be any one or more of the following cell types: Chinese hamster ovary (CHO) cell (e.g., CHO K1, DXB-11 CHO, Veggie-CHO), COS (e.g., COS-7), kidney (e.g., HEK293, 293 EBNA, MSR 293, MDCK, HaK, BHK21), HeLa, HepG2, WI38, MRC 5, Colo25, HB 8065, HL-60, Jurkat, Daudi, A431 (epidermal), CV-1, U937, 3T3, L cell, C127 cell, SP2/0, NS-0, and MMT cell and tumor cell. In certain embodiments, the cell is a CHO cell.

These and other objects, features and advantages of the disclosed methods will become apparent from the following detailed description of the various aspects of the method taken in conjunction with the accompanying drawings.

BRIEF DESCRIPTION OF THE DRAWINGS AND TABLES

Figure 1B:
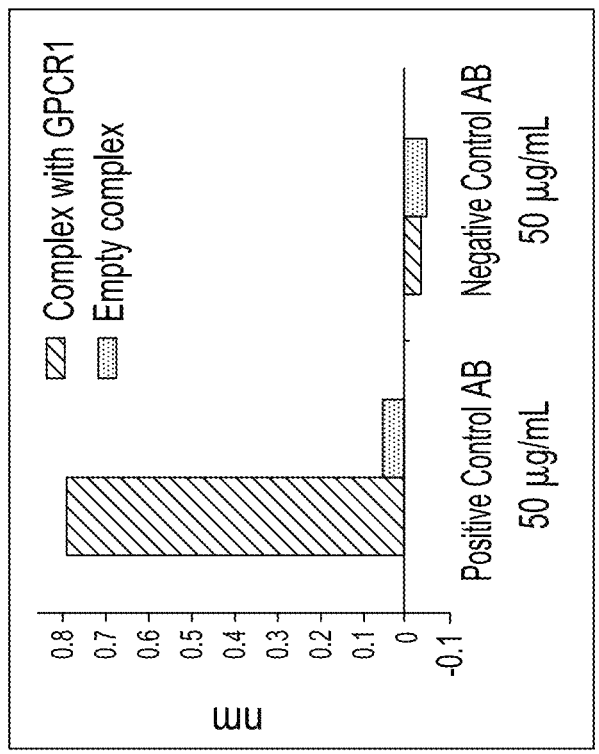

FIGS. 1A-1B demonstrate that a transmembrane protein of interest presented by a lipid bilayer-membrane scaffold protein complex specifically bind antibodies that recognize the transmembrane protein of interest and are detectable in vitro using the disclosed methods. Lipid bilayer-membrane scaffold protein complexes having at least two membrane scaffold proteins, each containing a detectable Bir-A label, and containing a first exemplary transmembrane protein of interest (Complex with GPCR1) were compared to control lipid bilayer-membrane scaffold protein complexes that do not include a transmembrane protein of interest (empty complex) for their ability to bind an exemplary antibody known to bind the GPCR1 (positive control AB) and an isotype control mab (negative control AB) that does not bind the GPCR protein. (A) The histogram shows the results of an octet assay demonstrating that a transmembrane protein of interest presented by a lipid bilayer-membrane scaffold protein complex specifically bind to the positive control antibody (0.6 nm) but not between anti-GPCR1 antibody and empty complex (−0.05 nm), negative control antibody and lipid bilayer-membrane scaffold protein complex including GPCR1 transmembrane protein (−0.06 nm), or between negative control antibody and empty complex (−0.03 nm). (B) The ability to detect and separate biotinylated lipid bilayer-membrane scaffold protein complexes presenting a transmembrane protein of interest (Complex with GPCR1) from biotinylated lipid bilayer-membrane scaffold protein complexes that do not contain a transmembrane protein of interest (empty complex) was analyzed by providing biotinylated lipid bilayer-membrane scaffold protein complex with or without transmembrane protein to plates having streptavidin tethered thereto, and then incubating with antibody known to bind the GPCR1 (positive control AB) or negative control antibody. The histogram shows that transmembrane protein of interest presented by a lipid bilayer-membrane scaffold protein complex specifically bind to the positive control antibody but not negative control antibody.

FIGS. 2A-2F demonstrate the detection and separation of antibody-producing B cells that express antibodies specific to exemplary transmembrane proteins of interest by flow cytometry. Splenocytes were harvested and isolated from control mice that were not immunized (A, C, E) and genetically-engineered mice immunized by injection of DNA encoding a first transmembrane protein of interest (GPCR1, B), a second transmembrane protein of interest (GPCR2, D), or a third transmembrane protein of interest (GPCR3, F). A population of B cells (Surface IgG Positive Cells) that express antibody specific to each of the exemplary transmembrane proteins of interest (Antigen Binding Cells) was detected and collected using FACS by staining the splenocytes with fluorescent labels to B cell markers (i.e., anti-IgG) and contacting the population of cells with a biotinylated lipid bilayer-membrane scaffold protein complex that presents one of the exemplary transmembrane proteins of interest. (A) Only two B cells in one million splenocytes obtained from a control mouse bound non-specifically to the first transmembrane protein of interest presented by a biotinylated lipid bilayer-membrane scaffold protein complex presenting (rectangle). (B) Eleven out of one million B cells expressing an antibody specific to the first exemplary GPCR transmembrane protein of interest (GPCR1) were detected using the present methods (rectangle). (C) Only two B cells in one million splenocytes obtained from a control mouse bound non-specifically to the second transmembrane protein of interest presented by a biotinylated lipid bilayer-membrane scaffold protein complex presenting (rectangle). (D) Seventy-eight out of one million B cells expressing antibody specific to the second exemplary GPCR transmembrane protein of interest (GPCR2) were detected using the present methods (rectangle). (E) Only eleven B cells that bound non-specifically to the third transmembrane protein of interest presented by a biotinylated lipid bilayer-membrane scaffold protein complex presenting (rectangle) were obtained from one million splenocytes from a control mouse. (F) Sixty-five out of one million B cells expressing an antibody specific to the third exemplary GPCR transmembrane protein of interest (GPCR3) were detected using the present methods (rectangle).

Figure 3:
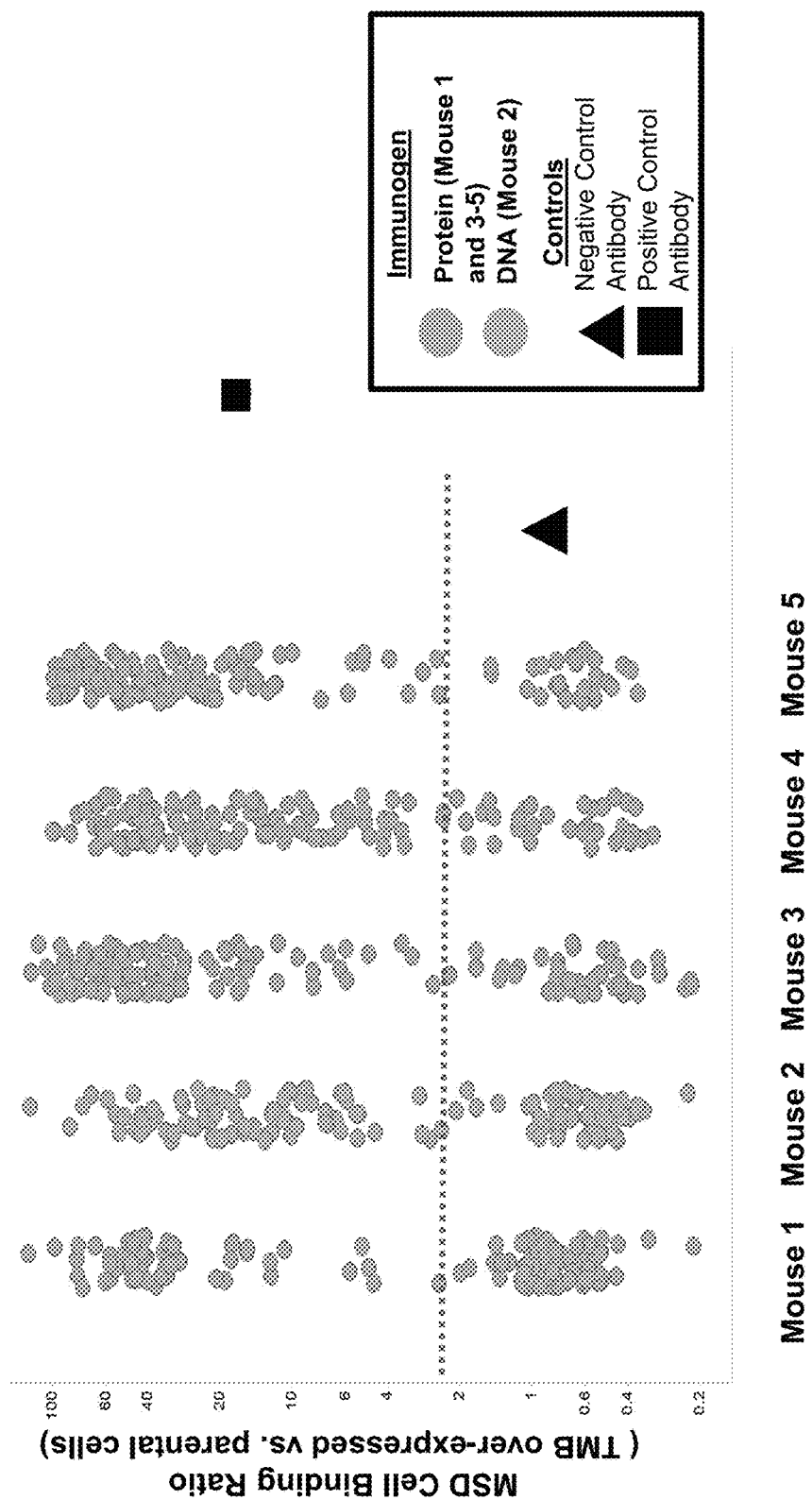

FIG. 3 shows that antibodies isolated from antibody-producing cells using a biotinylated lipid bilayer-membrane scaffold protein complex to present a transmembrane protein antigen specifically bind to a second exemplary GPCR transmembrane protein of interest independent of the type of immunogen used. Antibody-producing cells were obtained from genetically engineered mice immunized with either DNA encoding the transmembrane protein (DNA) or a purified transmembrane protein of interest (Protein) using a biotinylated lipid bilayer-membrane scaffold protein complex presenting the transmembrane protein of interest and antibodies were generated for screening. A full-length transmembrane protein of interest antigen was expressed in cells (TMB over-expressed) and antigen expressing cells were compared to control cells that were not transfected with DNA encoding either the TMB (parental cells). Cells were then incubated with antibodies to identify antibodies that specifically bind the exemplary transmembrane protein of interest. Antibodies above the dashed line were capable of binding the transmembrane protein of interest. In contrast, antibodies below the dashed line were weak binders or unable to bind the transmembrane protein of interest, as indicated by comparison to the positive (square) and negative (triangle) control antibodies.

Figure 4:
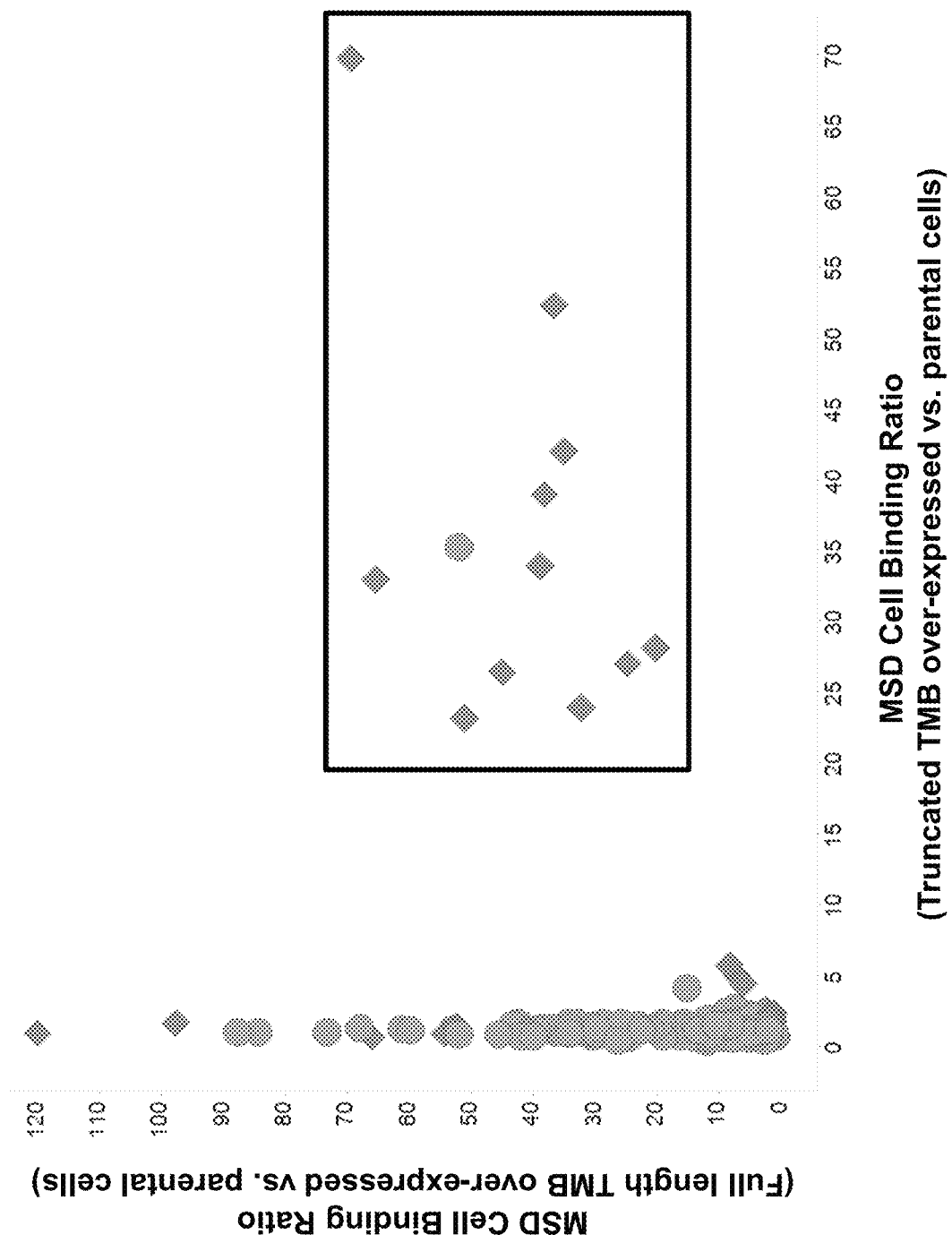

FIG. 4 shows antibodies isolated from antibody-producing cells using the disclosed methods, which were expressed for screening bind to a transmembrane protein of interest antigen expressed on the surface of cells. Antibody-producing cells were obtained from immunized genetically engineered mice using a biotinylated lipid bilayer-membrane scaffold protein complex presenting an n-terminally truncated form of the transmembrane protein of interest antigen and antibodies were generated for screening. A truncated form of a transmembrane protein of interest antigen was expressed in cells (Truncated TMB over-expressed) or a full-length form of a transmembrane protein of interest antigen was expressed in cells (Full-length TMB over-expressed) and antigen expressing cells were compared to control cells that were not transfected with DNA encoding either a truncated TMB antigen or full-length TMB (parental cells) when cells were incubated with antibodies to identify antibodies that specifically bind an epitope located in an extracellular loop domain of the exemplary transmembrane protein of interest (box).

Table 1: The isolation of antibody from cells that express cell-surface antibodies to various transmembrane proteins from immunized mice. Mice that have been genetically-engineered to prevent expression of a transmembrane protein of interest from an endogenous gene (genetically modified mouse w/out antigen) or genetically-engineered mice that express transmembrane protein of interest from an endogenous gene (genetically modified mouse), were immunized with DNA encoding a transmembrane protein of interest (DNA), DNA encoding a modified form of the transmembrane protein (modified DNA), purified transmembrane protein (protein), a lipid bilayer-membrane scaffold protein complex encompassing a transmembrane protein of interest (complex w/antigen) or a combination thereof. Antibody-producing cells collected using the sorting methods disclosed herein (cell sorting and complex w/antigen) and antibodies were isolated from the cells and compared to antibodies isolated from cells obtained using standard hybridoma techniques (hybridoma). For each of the transmembrane proteins analyzed, a higher percentage of antibodies that bound the transmembrane protein of interest were obtained from antibody-producing by sorting cells with lipid bilayer-membrane scaffold protein complex presenting a transmembrane protein of interest than standard hybridoma techniques.

Table 2: Comparison of cell-sorting strategies ability to obtain antibody-producing cells that express antibody that specifically binds to a transmembrane protein of interest. Genetically engineered mice with (VI) or without (VI—KO) the endogenous mouse gene encoding the exemplary transmembrane protein of interest analyzed, i.e, GPCR1 or Ion Channel 2, were immunized by injection of one or more of the following immunogens: DNA encoding a transmembrane protein of interest (DNA), purified transmembrane protein (Protein), a viral-like particle capable of expressing the transmembrane protein of interest (VLP) or a combination thereof (VLP and DNA). B cells obtained from the immunized mice were then sorted using one of the following sorting agents: biotinylated lipid bilayer-membrane scaffold protein complex that present the transmembrane protein (Complex w/TMB), a VLP or a purified transmembrane protein (Protein). Cells that produced antibody which bound to the sorting agent were then collected, and antibodies were generated from each cell for comparison.

Table 3: A comparison of antibody generated from antibody-producing cells obtained from genetically-engineered mice that were immunized with either DNA encoding a human transmembrane protein of interest (DNA) or the purified human transmembrane protein (Protein), where cells obtained from each mouse were sorted using biotinylated lipid bilayer-membrane scaffold protein complex that presented the transmembrane protein of interest (Complex w/TMB). The data provided the result of 5 representative immunization campaigns.

Table 4: The isolation of antibody-producing cells and generation of antibodies from genetically modified mice that do not express the mouse homolog of two different exemplary transmembrane proteins of interest (VI—KO), comparing different immunization strategies to demonstrate the biotinylated lipid bilayer-membrane scaffold protein complex can be used to obtain cross-reactive antibody that binds to the mouse homolog of a transmembrane protein of interest (mouse TMB) and human homolog of the transmembrane protein of interest (human TMB). The data provided are a combination of four representative immunization campaigns for TMB1, and the four representative immunization campaigns for TMB2.

Table 5: The isolation of antibody-producing cells and generation of antibodies from genetically modified mice that do not express the mouse homolog of an exemplary transmembrane protein of interest (VI—KO), demonstrate that immunization of genetically modified mice with lipid bilayer-membrane scaffold protein complex encompassing A human TMB2 protein (human TMB2) and sorting of antibody-producing B cells with a lipid bilayer-membrane scaffold protein complex presenting human TMB2 protein (Complex w/human TMB2) and/or with a lipid bilayer-membrane scaffold protein complex presenting mouse TMB2 protein (Complex w/mouse TMB2), identified antibody-producing B cells that express cross-reactive antibody capable of binding the mouse TMB2 and the human TMB2 protein homologs, as well as antibody specific to the human TMB2 protein. The data provided are a combination of two representative immunization campaigns.

DETAILED DESCRIPTION

Disclosed herein are methods that utilize lipid bilayer-membrane scaffold protein complexes to present transmembrane protein antigens to antibodies produced by cells. The lipid bilayer-membrane scaffold protein complexes include a transmembrane protein of interest or a portion thereof, as well as lipids and membrane scaffold proteins commonly found in the membranes of naturally occurring cells, and thus present the transmembrane protein antigen to an antibody in its natural conformation. As such, lipid bilayer-membrane scaffold protein complexes are used in the present methods to identify and collect a particular subset of antibodies (or cells that express antibody) in a population that bind to an epitope on a transmembrane protein that is accessible in nature, such as, for example, an extracellular domain.

Without being limited to any one theory, the methods disclosed herein reveal that immunizing animals, and isolating antibody-producing cells from the immunized animals using lipid bilayer-membrane scaffold protein complexes that present a transmembrane protein of interest antigen, can identify cells that produce antibody specific to an epitope on conformationally accurate transmembrane proteins.

Furthermore, antibodies and antibody-encoding nucleic acids can be isolated directly from antibody-producing cells by, for example, single-cell isolation and collection techniques, such as FACS. Therefore, the disclosure also provides an effective and efficient method for obtaining antibodies with an affinity for transmembrane proteins directly from a population of antibody-producing cells. The methods bypass the need for time-consuming screening, identification and selection of epitope-specific antibodies by site-directed mutagenesis, and other known techniques, in order to ascertain whether or not a particular antibody recognizes a desired portion of a transmembrane protein of interest.

In one aspect of the disclosure, a method for obtaining antibodies, or a population of cells that express antibody to a transmembrane protein of interest, is provided that includes contacting a population of antibody-producing cells with a lipid bilayer-membrane scaffold protein complex that presents a transmembrane protein of interest or a portion thereof. In one embodiment, the method includes contacting a population of antibody-producing cells obtained from an animal with a lipid bilayer-membrane scaffold protein complex encompassing a transmembrane protein of interest or portion thereof to permit binding between the transmembrane protein (i.e., antigen) and an antibody on the surface of a cell, and collecting the bound antibody-producing cells within the cell population.

In the description that follows, certain conventions will be followed as regards the usage of terminology. Generally, terms used herein are intended to be interpreted consistently with the meaning of those terms as they are known to those of skill in the art. In practicing the present disclosure, many conventional techniques in molecular biology, microbiology, cell biology, biochemistry, and immunology are used, which are within the skill of the art. These techniques are described in greater detail in, for example, Molecular Cloning: a Laboratory Manual 4th edition, J. F. Sambrook and D. W. Russell, ed. Cold Spring Harbor Laboratory Press 2012; Recombinant Antibodies for Immunotherapy, Melvyn Little, ed. Cambridge University Press 2009; "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001). The contents of these references and other references containing standard protocols, widely known to and relied upon by those of skill in the art, including manufacturers' instructions are hereby incorporated by reference as part of the disclosure.

Immunization to Generate Antibody-Producing Cells

Immunization of animals can be accomplished by any methods known in the art. See, for example, E. Harlow and D. Lane "Antibodies A Laboratory Manual, Cold Spring Harbor" (1988); Malik and Lillehoj, Antibody techniques: Academic Press, 1994, CA. For example, an immunogen may be administered directly to an animal such as a mammal via various routes including, but not limited to, intravenous or intraperitoneal injection, with or without adjuvant, where adjuvant can aid in stimulation of the immune response. Adjuvants known in the art include, but are not limited to, complete and incomplete Freund's adjuvant, MPL+TDM adjuvant system (Sigma), or RIBI (muramyl dipeptides). See O'Hagan, Vaccine Adjuvant, by Human Press, (2000) NJ. The term "immunogen" refers to a composition comprising an antigen (such as, for example, a transmembrane protein of interest or a nucleic acid encoding the same) against which antigen-specific antibodies are generated by a host's immune response. The term "antigen" refers to a molecule or a portion of a molecule capable of being bound by a binding agent, such as an antibody or fragment thereof. An antigen is also capable of being used produce antibodies capable of binding to an epitope of each antigen.

Immunogen can be administered to the host animal as a protein, a nucleic acid sequence encoding a protein or fragment thereof, a peptide fragment, a protein-fusion or by carrier that contains the immunogen-encoding gene of interest or the protein immunogen or a peptide fragment thereof. The immunization process can induce an immune response from the host and expresses an antigen (such as, a transmembrane protein of interest) using the host's cellular expression machinery in vivo.

Various immunization techniques are known in the art, and can be used in carrying out the methods. For example, an animal can be been immunized by injection with an immunogen, such as a nucleic acid encoding at least a portion of a transmembrane protein of interest, at least a portion of the transmembrane protein of interest, a carrier that includes such a nucleic acid, transmembrane protein of interest or portion thereof.

In some instances, an animal is immunized with a nucleic acid encoding a transmembrane protein of interest or a portion thereof. In certain embodiments, the animal is immunized with a nucleic acid encoding the full-length transmembrane protein of interest. In particular embodiments, the animal is immunized with a nucleic acid encoding a full-length human transmembrane protein of interest. In other embodiments, the animal is immunized with a nucleic acid encoding a full-length non-human transmembrane protein of interest. In particular embodiments, the animal is immunized with a nucleic acid encoding a full-length mouse transmembrane protein of interest.

The term "nucleic acid" or "nucleic acid sequence" or "nucleotide sequence" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. The term "nucleic acid encoding" or "nucleic acid that encodes" refers to DNA or RNA sequence that encodes for a sequence of amino acids, such as a peptide, protein, detectable element or label, and/or a regulatory element. A "gene" refers to a DNA nucleic acid sequence that encodes a sequence of amino acids which comprise all or part of one or more polypeptides, proteins or enzymes, and may or may not include introns, and regulatory DNA sequences, such as promoter or enhancer sequences, 5'-untranslated region, or 3'-untranslated region which affect, for example, the conditions under which the gene or gene product is expressed.

The terms "polypeptide," "peptide" and "protein" are used herein to refer to a polymer of amino acid residues linked via peptide bonds. The terms include amino acid polymers in which one or more amino acid residue is an artificial chemical mimetic of a corresponding naturally occurring amino acid, as well as to naturally occurring amino acid polymers and non-naturally occurring amino acid polymers. The term "protein" refers to large polypeptides. For example, in the present disclosure a protein can be a full-length or an endogenous protein. The term "peptide" typically refers to short polypeptides such as, for example, a fragment or portion of a protein or polypeptide. As used herein a "fragment" or "portion" of a polypeptide or protein refers to any portion of the polypeptide smaller than the full-length polypeptide or protein expression product. Fragments or portions can be "truncated" or deletion analogs of the full-length protein wherein one or more amino acid residues have been removed from the full-length protein. For example, in the present disclosure, a peptide can be described as a "truncated protein" or "a portion of a protein" or "fragment of a protein". In certain instances, "a portion" of a transmembrane protein of interest includes at least an entire transmembrane portion of the transmembrane protein of interest. A "truncated protein" may be a portion of a transmembrane protein of interest that does not include the amino-terminus and/or carboxy-terminal portion of the full-length protein. Synthetic polypeptides, peptides and proteins can be synthesized, for example, using an automated polypeptide synthesizer or by recombinant techniques known to those in the art.

The terms "transmembrane protein" and "transmembrane protein of interest" are used interchangeably herein to mean a protein or polypeptide portion thereof that is attached to and embedded in a membrane of a cell or organelle. Therefore, a transmembrane protein is a protein that traverses a membrane, and thus is composed of at least one membrane spanning domain. In some instances, the trandmembrane protein also includes at least one cytoplasmic domain and/or at least one extracellular domain. The cytoplasmic domain(s) can be one or more of an amino-terminal domain, a carboxy-terminal domain, and an intracellular loop domain. The extracellular domain(s) can be one or more of an amino-terminal domain, a carboxy-terminal domain and an extracellular loop domain. In some instances, the extracellular domain of a transmembrane protein of interest includes an N-terminal extracellular domain, a C-terminal extracellular domain, and/or an extracellular loop domain between one or more membrane spanning domains of the transmembrane protein of interest. The transmembrane protein can be a naturally-occurring protein derived from any organism including, but not limited to, prokaryotes, eukaryotes and viruses. In certain embodiments, the transmembrane protein can be a human, chimpanzee, rhesus monkey, rabbit, horse, sheep, rat, mouse, dog, chicken or goat protein. In some instances, the transmembrane protein is a mammalian protein, such as a human, mouse, rat or primate transmembrane protein. In specific embodiments, the transmembrane protein of interest is a human protein. In particular embodiments, the transmembrane protein of interest is a non-human protein. In one embodiment, the transmembrane protein of interest is a mouse protein.

In some embodiments, the transmembrane protein of interest is modified as described herein. Exemplary modified transmembrane proteins of interest can include one or more of the following alterations to their native amino acid sequence: amino acid substitutions, amino acid deletions, amino acid insertions. In some embodiments, the transmembrane protein of interest is modified to delete, i.e., "truncate", a portion of the transmembrane protein such as, for example, the n-terminal and/or c-terminal domain of the full-length protein. In some embodiments, the transmembrane protein of interest includes stabilizing mutations in the amino-terminus, one or more extracellular loop domains, one or more of the transmembrane domains, one or more intracellular domains, the c-terminus or a combination thereof. In certain embodiments, the transmembrane protein is a chimeric transmembrane protein. In certain embodiments, the modified transmembrane protein of interest includes one or more detectable elements such as, for example, a His-tag, FLAG-tag, Avi-tag or Bir-A tag. In particular embodiment, the transmembrane protein of interest includes a His-tag and a FLAG-tag.

In some embodiments, the transmembrane protein is a ligand-activated protein, whereby the transmembrane protein changes conformation in the presence or absence of ligand (i.e., having an active and inactive state). For example, a ligand-activated transmembrane protein that can bind a ligand on an intracellular or extracellular domain, whereby binding induces a conformational change in one or more domains of the transmembrane protein which modulates signal transmission in a cell. In some instances, the transmembrane protein of interest is a solute carrier transporter (SLC), a receptor, a receptor with kinase activity, a class I growth factor receptor, a G-protein coupled receptor (GPCR), an ion channel protein or a tetraspanin. In certain instances, the transmembrane protein of interest is a GPCR protein, tetraspanin protein, or an ion channel protein. In one embodiment, the transmembrane protein of interest is an SLC protein.

In one embodiment, the transmembrane protein of interest is a GPCR protein. GPCRs for use in the present methods are well known in the art. See, for example, Foord et al., *Pharmacol. Rev.* (2005) 57:279-288, the entire contents of which is incorporated herein by reference. Thus, the GPCR may be any of an adenosine receptor, a β-adrenergic receptor, a neurotensin receptor, a muscarinic acid receptor, a 5-hydroxytryptamine receptor, an adrenoceptor, an anaphylatoxin receptor, an angiotensin receptor, an apelin receptor, a bombesin receptor, a bradykinin receptor, a cannabinoid receptor, a chemokine receptor, a cholecystokinin receptor, a dopamine receptor, an endothelin receptor a free fatty acid receptor, a bile acid receptor, a galanin receptor, a motilin receptor, a ghrelin receptor, a glycoprotein hormone receptor, a GnRH receptor, a histamine receptor, a KiSS1-derived peptide receptor, a leukotriene and lipoxin receptor, a lysophospholipid receptor, a melanin-concentrating hormone receptor, a melanocortin receptor, a melatonin receptor, a neuromedin U receptor, a neuropeptide receptor, a N-formylpeptide family receptor, a nicotinic acid receptor, an opioid receptor, an opsin-like receptor, an orexin receptor, a P2Y receptor, a peptide P518 receptor, a platelet-activating factor receptor, a prokineticin receptor, a prolactin-releasing peptide receptor, a prostanoid receptor, a protease-activated receptor, a relaxin receptor, a somatostatin receptor, a SPC/LPC receptor, a tachykinin receptor, a trace amino receptor, a thyrotropin-releasing hormone receptor, an urotensin receptor, a vasopressin/oxytocin receptor, an orphan GPCR, a calcitonin receptor, a corticotropin releasing factor receptor, a glucagon receptor, a parathyroid receptor, a VIP/PACAP receptor, a LNB7TM receptor, a GABA receptor, a metabotropic glutamate receptor, and a calcium sensor receptor In certain embodiments, the transmembrane protein of interest is a GPCR protein such as, for example, CCR5, ADORA2A, ADRB3, C3AR1, ADRA2A, GLP1R, CCR4, CCR8 and CXCR4. In a specific embodiment, the transmembrane protein is a GPCR protein selected from the following GPCR proteins: CCR5, ADORA2A, ADRB3, C3AR1, ADRA2A, GLP1R, CCR4, CCR8 or CXCR4. In one embodiment, the transmembrane protein is CCR5. In another embodiment, the transmembrane protein is ADORA2A. In other embodiments, the transmembrane protein is C3AR1. In yet another embodiment, the transmembrane protein is ADRA2A. In other embodiments, the transmembrane protein is GLP1R.

In some instances, the transmembrane protein is a tetraspanin. In certain instances, the transmembrane protein of interest is a tetraspanin such as, for example, TSPAN 1 through TSPAN19, TSPAN21, TSPAN23, TSPAN 31, TSPAN 32, TSPAN 33, UPK1B, PRPH2, CD151, CD53, CD37, CD82, CD81, CD9, CD63, TCD63, CLND6 and CLND9. In some embodiments, the transmembrane protein is CD63. In another embodiment, CLDN6. In other embodiments, the transmembrane protein is CLDN9.

In other embodiments, the transmembrane protein of interest is an ion channel protein. In one embodiment, the ion channel protein is a voltage-gated ion channel protein. In a specific embodiment, the voltage-gated ion channel protein is a voltage-dependent calcium channel gamma-1 subunit (CACNG1) or a voltage gated potassium channel protein such as, for example, KVS or KIRS. In other embodiments, the ion channel protein is a calcium-activated potassium channel protein (e.g., BKCa, MaxiK or Sk), a voltage-gated sodium channel protein such as, for example, a NaV1 protein (e.g., voltage-gated channel alpha subunit 9 (NaV1.7), voltage-gated channel alpha subunit 2 (NaV1.2)), a calcium channel protein (e.g., CAV) or a chloride channel protein (e.g., CIC). In some embodiments, the ion channel protein is a transient receptor potential channel (TRP) protein. In specific embodiments, the TRP is a canonical transmembrane protein (TRPC), a vanilloid receptor (TRPV), meliastatin (TRPM), a polycystin (TRPP), a mucolipin (TRPML) or anankyrin transmembrane protein 1 (TRPA1), such as canonical TRP (TRPC), vanilloid receptors (TRPV), meliastatin (TRPM), polycystins (TRPP), mucolipins (TRPML), ankyrin transmembrane protein 1 (TRPA1). In a particular embodiment, the transmembrane protein of interest is BKCa, MaxiK, Sk, NAV 1.7, CACNG1, CAV, CIC, or a TRP.

In certain embodiments, the transmembrane protein of interest is a voltage-gated sodium channel protein. The family of voltage-gated sodium channels has nine known members, with amino acid identity >50% in the transmembrane segments and extracellular loop regions. The proteins of these channels are named NaV1.1 through NaV1.9 referred to generally as "NaV1 proteins", and the gene names that encode NaV1.1-NaV1.9 are referred to as Scn1a through Scn11a. Each of the NaV1 proteins has four repeat domains, each containing six membrane-spanning segments. The fourth segment is highly conserved and acts as the channel's voltage sensor. The voltage sensitivity of this channel is due to positive amino acids located at every third position in the fourth segment (Nicholls et al., (2012) "From Neuron to Brain," 5th ed. pg. 86, which is herein incorporated by reference in its entirety). When stimulated by a change in transmembrane voltage, this segment moves toward the extracellular side of the cell membrane, allowing the channel to become permeable to ions. The ions are conducted through a pore, which can be broken into two regions. The more external (i.e., more extracellular) portion of the pore is formed by the region between the fifth and sixth transmembrane segments (also known as "P-loop") of each of the four domains. This region is the narrower part of the pore and is responsible for its ion selectivity. The inner portion (i.e., more cytoplasmic) of the pore is formed by the combined fifth and sixth transmembrane segments of the four domains. More specifically, the human NaV1.1 protein corresponds to the amino acid sequence set forth in Accession No. P35498.2; the human NaV1.2 protein corresponds to the amino acid sequence set forth in Accession No. Q99250.3; the human NaV1.3 protein corresponds to the amino acid sequence set forth in Accession No. Q9NY46.2; the human NaV1.4 protein corresponds to the amino acid sequence set forth in Accession No. P35499.4; the human NaV1.5 protein corresponds to the amino acid sequence set forth in Accession No. Q14524.2; the human NaV1.6 protein corresponds to the amino acid sequence set forth in Accession No Q9UQD0.1; the human NaV1.7 protein corresponds to the amino acid sequence set forth in Accession No. Q15858.3; the human NaV1.8 protein corresponds to the amino acid sequence set forth in Accession No. Q9Y5Y9.2; and the human NaV1.9 protein corresponds to the amino acid sequence set forth in Accession No. Q9UI33.2.

In one such embodiment, the transmembrane protein of interest is a NaV1 protein. In specific embodiments, the transmembrane protein of interest is NAV1.7. NaV1.7 is expressed in nociceptive (pain) neurons at dorsal root ganglion, sympathetic neurons, Schwann cells and neuroendocrine cells. NaV1.7 is a critical component of membrane excitability and important for sensation of pain. Gain-of-function mutations in the human SCN9A gene have been associated with pain syndromes, while loss-of-function mutations are associated with profound insensitivity to pain. NaV1.7 is highly conserved across species, as evident from an alignment of exemplary homolog sequences of NaV1.7 proteins from the following 14 animal species. The human NaV1.7 protein corresponds to the amino acid sequence set forth in Accession No. Q15858.3; the chimpanzee NaV1.7 homolog corresponds to the amino acid sequence set forth in Accession No. XP_016804947.1; the Rhesus monkey NaV1.7 protein corresponds to the amino acid sequence set forth in Accession No. XP_014965766.1; the Sunda flying lemur NaV1.7 protein corresponds to the amino acid sequence set forth in Accession No. XP_008588371.1; the cattle NaV1.7 protein corresponds to the amino acid sequence set forth in Accession No. NP_001104257.2; the sheep NaV1.7 protein corresponds to the amino acid sequence set forth in Accession No. XP_004004679.1; the Arabian camel NaV1.7 protein corresponds to the amino acid sequence set forth in Accession No. XP_010980767.1; the killer whale NaV1.7 protein corresponds to the amino acid sequence set forth in Accession No. XP_004267302.1; the horse NaV1.7 protein corresponds to the amino acid sequence set forth in Accession No. XP_001496473.1; the dog NaV1.7 protein corresponds to the amino acid sequence set forth in Accession No. XP_022270547.1; the mouse NaV1.7 protein corresponds to the amino acid sequence set forth in Accession No. Q62205.2; the rat NaV1.7 protein corresponds to the amino acid sequence set forth in Accession No. O08562.1; the rabbit NaV1.7 protein corresponds to the amino acid sequence set forth in Accession No. Q28644.1; and the chicken NaV1.7 protein corresponds to the amino acid sequence set forth in Accession No. NP_001280211.1.

In a particular embodiment, the transmembrane protein of interest is human NaV1.7. In another embodiment, the transmembrane protein of interest is mouse NaV1.7.

In other embodiments, the transmembrane of protein of interest is NaV1.2. NaV1.2 is expressed in central neurons and peripheral neurons. Mutations in the human SCN2A gene (encoding NaV1.2) have been linked to several seizure disorders and autism spectrum disorder. NaV1.2 is highly conserved across species, as evident from an alignment of exemplary sequences of NaV1.2 proteins from 14 animal species. The accession numbers for the exemplary sequences included in the alignment are: the human NaV1.2 homolog corresponds to the amino acid sequence set forth in Accession No. Q99250.3; the chimpanzee NaV1.2 homolog corresponds to the amino acid sequence set forth in Accession No. XP_003820970.1; the Rhesus monkey NaV1.2 protein corresponds to the amino acid sequence set forth in Accession No. XP_001100368.1; the Sunda flying lemur NaV1.2 protein corresponds to the amino acid sequence set forth in Accession No. XP_008582720.1; the cattle NaV1.2 protein corresponds to the amino acid sequence set forth in Accession No. NP_001137581.1; the sheep NaV1.2 protein corresponds to the amino acid sequence set forth in Accession No. XP_014948870.1; the Arabian camel NaV1.2 protein corresponds to the amino acid sequence set forth in Accession No. XP_010980763.1; the killer whale NaV1.2 protein corresponds to the amino acid sequence set forth in Accession No XP_004283641.1; the horse NaV1.2 protein corresponds to the amino acid sequence set forth in Accession No. XP_014588001.1; the mouse NaV1.2 protein corresponds to the amino acid sequence set forth in Accession No. NP_001092768.1; the rat NaV1.2 protein corresponds to the amino acid sequence set forth in Accession No. P04775.1; the rabbit NaV1.2 protein corresponds to the amino acid sequence set forth in Accession No. XP_008256915.1; the chicken NaV1.2 protein corresponds to the amino acid sequence set forth in Accession No. NP_001280210.1; and the green sea turtle NaV1.2 protein corresponds to the amino acid sequence set forth in Accession No. XP_007056690.1.

In a particular embodiment, the transmembrane protein of interest is the human NaV1.2 homolog. In another embodiment, the transmembrane protein of interest is the mouse NaV1.2 homolog.

In some embodiments, transmembrane protein of interest is a CACNG1 protein. In one embodiment, the transmembrane protein of interest is a human CACNG1 protein. In another embodiment, the transmembrane protein of interest is a non-human CACNG1 protein.

In certain instances, the transmembrane protein of interest is an SLC protein. SLC proteins have been characterized and are well-known to those of ordinary skill in the art. For example, hundreds of human membrane-spanning SLC proteins have been identified, which are organized into numerous families of SLC proteins, as described, for example, in Lin, L. et al. *Nat. Rev. Drug Disc.* (2015) 14:8 pp. 543-560, the entire contents of which is expressly incorporated herein by reference. Accordingly, in certain embodiments the transmembrane protein of interest is an SLC protein such as, for example, SLCO1A2, SLCO1B1, SLCO1B3, SLCO1B7, SLCO1C1, SLCO2A1, SLCO2B1, SLCO3A1, SLCO4A1, SLCO4C1, SLCO5A1, SLCO6A1, SLC1A1, SLC1A2, SLC1A3, SLC1A4, SLC1A5, SLC1A6, SLC1A7, SLC2A1, SLC2A2, SLC2A3, SLC2A4, SLC2A5, SLC2A6, SLC2A7, SLC2A8, SLC2A9, SLC2A10, SLC2A11, SLC2A12, SLC2A13, SLC2A14, SLC3A1, SLC3A2, SLC4A1, SLC4A2, SLC4A3, SLC4A4, SLC4A5, SLC4A7, SLC4A8, SLC4A9, SLC4A10, SLC4A11, SLC5A1, SLC5A2, SLC5A3, SLC5A4, SLC5A5, SLC5A6, SLC5A7, SLC5A8, SLC5A9, SLC5A10, SLC5A11, SLC5A12, SLC6A1, SLC6A2, SLC6A3, SLC6A4, SLC6A5, SLC6A6, SLC6A7, SLC6A8, SLC6A9, SLC6A10P, SLC6A11, SLC6A12, SLC6A13, SLC6A14, SLC6A15, SLC6A16, SLC6A17, SLC6A18, SLC6A19, SLC6A20, SLC6A21P, SLC7A1, SLC7A2, SLC7A3, SLC7A4, SLC7A5, SLC7A6, SLC7A7, SLC7A8, SLC7A9, SLC7A10, SLC7A11, SLC7A13, SLC7A14, SLC7A15P, SLC8A1, SLC8A2, SLC8A3, SLC8B1, SLC9A1, SLC9A2, SLC9A3, SLC9A4, SLC9A5, SLC9A6, SLC9A7, SLC9A8, SLC9A9, SLC9B1, SLC9B2, SLC9C1, SLC9C2, SLC10A1, SLC10A2, SLC10A3, SLC10A4, SLC10A5, SLC10A6, SLC10A7, SLC11A1, SLC11A2, SLC12A1, SLC12A2, SLC12A3, SLC12A4, SLC12A5, SLC12A6, SLC12A7, SLC12A8, SLC12A9, SLC13A1, SLC13A2, SLC13A3, SLC13A4, SLC13A5, SLC14A1, SLC14A2, SLC15A1, SLC15A2, SLC15A3, SLC15A4, SLC15A5, SLC16A1, SLC16A2, SLC16A3, SLC16A4, SLC16A5, SLC16A6, SLC16A7, SLC16A8, SLC16A9, SLC16A10, SLC16A11, SLC16A12, SLC16A13, SLC16A14, SLC17A1, SLC17A2, SLC17A3, SLC17A4, SLC17A5, SLC17A6, SLC17A7, SLC17A8, SLC17A9, SLC18A1, SLC18A2, 5LC18A3, SLC18B1, SLC19A1, SLC19A2, SLC19A3, SLC20A1, SLC20A2, SLC22A1, SLC22A2, SLC22A3, SLC22A4, SLC22A5, SLC22A6, SLC22A7, SLC22A8, SLC22A9, SLC22A10, SLC22A11, SLC22A12, SLC22A13, SLC22A14, SLC22A15, SLC22A16, SLC22A17, SLC22A18, SLC22A20P, SLC22A23, SLC22A24, SLC22A25, SLC22A31, SLC23A1, SLC23A2, SLC23A3, SLC23A4P, SLC24A1, SLC24A2, SLC24A3, SLC24A4, SLC24A5, SLC25A1, SLC25A2, SLC25A3, SLC25A4, SLC25A5, SLC25A6, UCP1, UCP2, UCP3, SLC25A10, SLC25A11, SLC25A12, SLC25A13, SLC25A14, SLC25A15, SLC25A16, SLC25A17, SLC25A18, SLC25A19, SLC25A20, SLC25A21, SLC25A22, SLC25A23, SLC25A24, SLC25A25, SLC25A26, SLC25A27, SLC25A28, SLC25A29, SLC25A30, SLC25A31, SLC25A32, SLC25A33, SLC25A34, SLC25A35, SLC25A36, SLC25A37, SLC25A38, SLC25A39, SLC25A40, SLC25A41, SLC25A42, SLC25A43, SLC25A44, SLC25A45, SLC25A46, SLC25A47, SLC25A48, MTCH1, MTCH2, SLC25A51, SLC25A52, SLC25A53, SLC26A1, SLC26A2, SLC26A3, SLC26A4, SLC26A5, SLC26A6, SLC26A7, SLC26A8, SLC26A9, SLC26A10, SLC26A11, SLC27A1, SLC27A2, SLC27A3, SLC27A4, SLC27A5, SLC27A6, SLC28A1, SLC28A2, SLC28A3, SLC29A1, SLC29A2, SLC29A3, SLC29A4, SLC30A1, SLC30A2, SLC30A3, SLC30A4, SLC30A5, SLC30A6, SLC30A7, SLC30A8, SLC30A9, SLC30A10, SLC31A1, SLC31A2, SLC32A1, SLC33A1, SLC34A1, SLC34A2, SLC34A3, SLC35A1, SLC35A2, SLC35A3, SLC35A4, SLC35A5, SLC35B1, SLC35B2, SLC35B3, SLC35B4, SLC35C1, SLC35C2, SLC35D1, SLC35D2, SLC35D3, SLC35E1, SLC35E2A, SLC35E2B, SLC35E3, SLC35E4, SLC35F1, SLC35F2, SLC35F3, SLC35F4, SLC35F5, SLC35F6, SLC35G1, SLC35G2, SLC35G3, SLC35G4, SLC35G5, SLC35G6, SLC36A1, SLC36A2, SLC36A3, SLC36A4, SLC37A1, SLC37A2, SLC37A3, SLC37A4, SLC38A1, SLC38A2, SLC38A3, SLC38A4, SLC38A5, SLC38A6, SLC38A7, SLC38A8, SLC38A9, SLC38A10, SLC38A11, SLC39A1, SLC39A2, SLC39A3, SLC39A4, SLC39A5, SLC39A6, SLC39A7, SLC39A8, SLC39A9, SLC39A10, SLC39A11, SLC39A12, SLC39A13, SLC39A14, SLC40A1, SLC41A1, SLC41A2, SLC41A3, RHAG, RHBG, RHCG, SLC43A1, SLC43A2, SLC43A3, SLC44A1, SLC44A2, SLC44A3, SLC44A4, SLC44A5, SLC45A1, SLC45A2, SLC45A3, SLC45A4, SLC46A1, SLC46A2, SLC46A3, SLC47A1, SLC47A2, SLC48A1, FLVCR1, FLVCR2, SLC49A3, SLC49A4, SLC50A1, SLC51A, SLC51B, SLC52A1, SLC52A2, SLC52A3, XPR1, MPC1, MPC2, MPC1L, LETM1, LETM2, LETMD1, SFXN1, SFXN2, SFXN3, SFXN4, SFXN5, NIPA1, NIPA2, NIPAL1, NIPAL2, NIPAL3, NIPAL4, MAGT1, TUSC3, MFSD2A, MFSD2B, MFSD4A, MFSD4B, MFSD5, ANKH, SPNS1, SPNS2, SPNS3, TMEM165, NPC1, NPC1L1, SLC66A1, SLC66A2, SLC66A3, CTNS, and MPDU1.

The term "endogenous" refers to a polypeptide or polynucleotide or other composition that is expressed naturally in a host organism, or originates within a cell, tissue or organism. "Exogenous" refers to a polypeptide, polynucleotide or other composition that originates outside a cell, tissue or organism, or is foreign to a particular host organism.

In some embodiments of the methods, an animal is immunized with a nucleic acid encoding a portion of a transmembrane protein of interest. In certain embodiments, the nucleic acid encodes for a truncated version of the full-length transmembrane protein of interest. In some embodiments, the truncated transmembrane protein of interest does not include, one or more extracellular loop domains, an amino-terminal and/or carboxy-terminal portion of the full-length transmembrane protein of interest. In particular embodiments, the truncated transmembrane protein does not include the amino-terminal portion of the full-length transmembrane protein of interest. In other embodiments, the truncated transmembrane protein does not include the carboxy-terminal portion of the full-length transmembrane protein of interest. In some embodiments, the truncated transmembrane protein does not include an extracellular loop domain of the full-length transmembrane protein of interest.

In some embodiments, an animal is immunized with a nucleic acid encoding a transmembrane protein of interest or a portion thereof that is encompassed in a carrier capable of expressing the nucleic acid. Non-limiting examples of carriers for use in immunization include vectors, such as plasmids, expression vectors, as well as virus-like particles (VLP), cells such as irradiated cells, exosomes and liposomes. The term "vector" is used to refer to any molecule (e.g., nucleic acid, plasmid or virus) used to transfer coding information to a host cell. An example of a vector is an "expression vector", which is a nucleic acid construct, generated recombinantly or synthetically, with a series of specified nucleic acid elements that permit transcription of a particular nucleic acid in a host cell. An expression vector can be part of a plasmid, virus, or nucleic acid fragment. In certain instances, an expression vector includes a nucleic acid to be transcribed operably linked to a promoter. The term "operably linked" refers to a functional linkage between a nucleic acid expression control sequence (such as, for example, a promoter, or array of transcription factor binding sites) and a second nucleic acid sequence, wherein the expression control sequence directs transcription of the nucleic acid corresponding to the second sequence.

In some embodiments, the animal is immunized with a vector comprising a nucleic acid encoding a transmembrane protein of interest or a portion thereof. In specific embodiments, the animal is immunized with an expression vector comprising a nucleic acid encoding a transmembrane protein of interest or a portion thereof. In one embodiment, the animal is immunized with a plasmid comprising a nucleic acid encoding a transmembrane protein of interest or a portion thereof.

In some instances, an immunogen is administered to a host animal by one or more injections over time, such as by intravenous injection or by intraperitoneal injection. In certain embodiments, the immunogen is administered to a host mammal by 1, 2, 3, 4 or more injections. In particular embodiments, the immunogen is administered by 3 separate injections.

The amount of immunogen administered to an animal can be readily determined by one of ordinary skill in the art using known methods.

In some instances, a nucleic acid immunogen is injected into an animal at a concentration of at least 0.1 mg/mL, at least 0.5 mg/mL, at least 1.0 mg/mL, at least 1.5 mg/mL, at least 2.0 mg/mL, at least 3.0 mg/mL, at least 4.0 mg/mL, at least 5.0 mg/mL, at least 6.0 mg/mL, at least 7.0 mg/mL, at least 8.0 mg/mL, at least 9.0 mg/mL, at least 9.5 mg/mL, at least 10.0 mg/mL, at least 10.5 mg/mL or greater. In certain embodiments, the nucleic acid immunogen is injected into an animal at a concentration of 0.5 mg/mL to 20 mg/mL, 0.5 mg/mL to 15 mg/mL, 0.5 mg/mL to 12 mg/mL, 0.5 mg/mL to 11 mg/mL, 1.0 mg/mL to 15 mg/mL, 1.0 mg/mL to 5 mg/mL, 1.0 mg/mL to 4 mg/mL, 1.0 mg/mL to 3 mg/mL, 1.0 mg/mL to 2 mg/mL, 2.0 mg/mL to 12 mg/mL, 5.0 mg/mL to 12 mg/mL, 7.0 mg/mL to 12 mg/mL, 8.0 mg/mL to 12 mg/mL, 8.0 mg/mL to 11 mg/mL, 9.0 mg/mL to 11 mg/mL, or 9.5 mg/mL to 10.5 mg/mL. In specific embodiments, the nucleic acid immunogen is injected into an animal at a concentration of 0.5 mg/mL, 0.7 mg/mL, 0.9 mg/mL, 1.0 mg/mL, 1.5 mg/mL, 1.6 mg/mL, 1.8 mg/mL, 2.0 mg/mL, 2.5 mg/mL, 3.0 mg/mL, 3.5 mg/mL, 4.0 mg/mL, 4.5 mg/mL, 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10.0 mg/mL, 10.5 mg/mL, 11.0 mg/mL, 11.5 mg/mL, 12.0 mg/mL, 12.5 mg/mL, 13.0 mg/mL, 13.5 mg/mL, 14.0 mg/mL, 14.5 mg/mL, 15.0 mg/mL, 15.5 mg/mL, or greater. In a particular embodiment, the nucleic acid immunogen is injected into an animal at a concentration of 1.6 mg/mL. In one embodiment, the nucleic acid immunogen is injected into an animal at a concentration of 10 mg/mL.

In some embodiments, the animal is immunized with a transmembrane protein of interest or a portion thereof. In certain embodiments, the transmembrane protein of interest or portion thereof is of human origin. In other embodiments, the animal is immunized with a non-human transmembrane protein of interest. In some embodiments, the animal is immunized with a nucleic acid encoding a full-length mouse transmembrane protein of interest. In some embodiments, the animal is immunized with a full-length transmembrane protein of interest. In specific embodiments, the transmembrane protein of interest is truncated. In some embodiments, the truncated transmembrane protein of interest does not include, one or more extracellular loop domains, an amino-terminal and/or carboxy-terminal portion of the full-length transmembrane protein of interest. In particular embodiments, the truncated transmembrane protein does not include the amino-terminal portion of the full-length transmembrane protein of interest. In other embodiments, the truncated transmembrane protein does not include the carboxy-terminal portion of the full-length transmembrane protein of interest. In one embodiment, the truncated transmembrane protein does not include an extracellular loop domain of the full-length transmembrane protein of interest.

In certain instances, a protein or peptide immunogen is administered to an animal at a concentration of at least 0.1 mg/mL, at least 0.2 mg/mL, at least 0.3 mg/mL, at least 0.4 mg/mL, at least 0.5 mg/mL, at least 0.6 mg/mL, at least 0.7 mg/mL, at least 0.8 mg/mL, at least 0.9 mg/mL, at least 1.0 mg/mL, at least 2.0 mg/mL, at least 3.0 mg/mL, at least 4.0 mg/mL, at least 5.0 mg/mL, at least 10.0 mg/mL or greater. In certain embodiments, the protein or peptide immunogen is injected into an animal at a concentration of 0.1 mg/mL to 20 mg/mL, 0.1 mg/mL to 15 mg/mL, 0.1 mg/mL to 10 mg/mL, 0.1 mg/mL to 8.0 mg/mL, 0.1 mg/mL to 7.0 mg/mL, 0.1 mg/mL to 6.0 mg/mL, 0.1 mg/mL to 5.0 mg/mL, 0.1 mg/mL to 3.0 mg/mL, 0.1 mg/mL to 2.0 mg/mL, 0.1 mg/mL to 1.0 mg/mL, 0.2 mg/mL to 10.0 mg/mL, 0.2 mg/mL to 7.0 mg/mL, 0.2 mg/mL to 6.0 mg/mL, 0.2 mg/mL to 5.0 mg/mL, 0.2 mg/mL to 3 mg/mL, 0.2 mg/mL to 2 mg/mL, 0.2 mg/mL to 1 mg/mL, 0.5 mg/mL to 10.0 mg/mL, 0.5 mg/mL to 7.0 mg/mL, 0.5 mg/mL to 5.0 mg/mL, 0.5 mg/mL to 3.0 mg/mL, 0.5 mg/mL to 2.0 mg/mL, 0.5 mg/mL to 1.0 mg/mL, 1.0 mg/mL to 5.0 mg/mL, 1.0 mg/mL to 3.0 mg/mL, 1.0 mg/mL to 2.0 mg/mL, 2.0 mg/mL to 10.0 mg/mL, 5.0 mg/mL to 10.0 mg/mL, inclusive. In specific embodiments, the protein or peptide immunogen is injected into an animal at a concentration of 0.1 mg/mL, 0.2 mg/mL, 0.25 mg/mL, 0.3 mg/mL, 0.35 mg/mL, 0.4 mg/mL, 0.45 mg/mL, 0.5 mg/mL, 0.55 mg/mL, 0.6 mg/mL, 0.65 mg/mL, 0.7 mg/mL, 0.75 mg/mL, 0.8 mg/mL, 0.85 mg/mL, 0.9 mg/mL, 0.95 mg/mL, 1.0 mg/mL, 1.5 mg/mL, 1.6 mg/mL, 1.8 mg/mL, 2.0 mg/mL, 2.5 mg/mL, 3.0 mg/mL, 3.5 mg/mL, 4.0 mg/mL, 4.5 mg/mL, 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10.0 mg/mL, 12.0 mg/mL, 15.0 mg/mL, 20.0 mg/mL, or greater. In a particular embodiment, the protein or peptide immunogen is injected into an animal at a concentration of 0.9 mg/mL. In one embodiment, the protein or peptide immunogen is injected into an animal at a concentration of 0.5 mg/mL. In another embodiment, the protein or peptide immunogen is injected into an animal at a concentration of 1.9 mg/mL. In a specific embodiment, the protein or peptide immunogen is injected into an animal at a concentration of 2.5 mg/mL.

In certain embodiments, the animal is immunized with a nucleotide sequence encoding a chimeric transmembrane protein of interest or a chimeric transmembrane protein of interest. The term "chimeric" as used herein refers to a protein, or nucleic acid that encodes a protein, having portions thereof derived from different species. For example, a chimeric protein can have one or more human domains and at least one non-human domain or vice-versa. A nucleic acid that encodes a chimeric protein can have, for example, a human gene encoding one or more domains of a protein operatively linked to a non-human gene encoding at least one domain of the protein.

In one non-limiting example, a chimeric nucleic acid includes a portion of a human gene encoding a first portion of a transmembrane protein that is operably linked to a portion of a mouse gene encoding a different portion of the transmembrane protein. In some embodiments, the animal is immunized with DNA encoding a chimeric transmembrane protein of interest that includes a human gene sequence encoding one or more extracellular loop domains of the human transmembrane protein and a mouse gene sequence encoding an amino-terminal domain and/or carboxy-terminal domain from the mouse homolog of the transmembrane protein. In other embodiments, the animal is immunized with DNA encoding a chimeric transmembrane protein of interest that includes DNA encoding the amino-terminal domain and/or carboxy-terminal domain from a human transmembrane protein and DNA encoding one or more extracellular loop domains of the mouse homolog of the transmembrane protein. In one embodiment, the animal is immunized with DNA encoding a chimeric transmembrane protein of interest that includes a gene sequence encoding one or more extracellular loop domains from a human transmembrane protein and a sequence encoding amino-terminal domain from the mouse homolog of the transmembrane protein. In specific embodiments, the animal is immunized with DNA encoding a chimeric transmembrane protein of interest that includes a gene sequence encoding amino-terminal domain from a human transmembrane protein and a gene sequence encoding one or more extracellular loop domains from the mouse homolog of the transmembrane protein. In certain embodiments, the nucleotide sequence encoding a chimeric transmembrane protein of interest is also modified to include a nucleotide sequence that encodes a detectable element such as, for example, a His-tag, FLAG-tag, Avi-tag or Bir-A-tag.

In some embodiments, the animal is immunized with a chimeric transmembrane protein of interest, which includes a portion of a human transmembrane protein of interest operably linked to a portion of a non-human homolog of the transmembrane protein of interest. In some embodiments, the animal is immunized with a chimeric transmembrane protein of interest that includes one or more extracellular loop domains from a human transmembrane protein of interest and an amino-terminal domain and/or carboxy-terminal domain from the mouse homolog of the transmembrane protein. In some embodiments, the animal is immunized with a chimeric transmembrane protein of interest that includes one or more extracellular loop domains from a human transmembrane protein and an amino-terminal domain from the mouse homolog of the transmembrane protein. In some embodiments, the animal is immunized with a chimeric transmembrane protein of interest that includes an amino-terminal domain and/or carboxy-terminal domain from a human transmembrane protein and one or more extracellular loop domains from a mouse homolog of the transmembrane protein. In some embodiments, the animal is immunized with a chimeric transmembrane protein of interest that includes an amino-terminal domain from a human transmembrane protein and one or more extracellular loop domains from the mouse homolog of the transmembrane protein. In certain embodiments, the chimeric transmembrane protein of interest also includes a detectable element such as, for example, a His-tag, FLAG-tag, Avi-tag or Bir-A tag. In one embodiment, the chimeric transmembrane protein of interest includes a His-tag and FLAG-tag.

In certain embodiments, the transmembrane protein of interest or nucleic acid immunogen is modified. In some embodiments, the immunogen is a modified transmembrane protein of interest or DNA encoding the same that includes one or more of stabilizing amino acid substitutions. In some embodiments, the modified transmembrane protein or nucleic acid encoding the same include one or more detectable element, such as a label, marker or feature. In one embodiment, the modified immunogen is a transmembrane protein of interest comprising a detectable label. In a specific embodiment, the detectable label is a FLAG-tag, Avi-tag, histidine tag (His-tag), Bir-A-tag or a combination thereof. In particulars embodiment, the detectable label or labels are located at the amino-terminus or carboxy-terminus of the transmembrane protein immunogen. In one embodiment, the transmembrane protein immunogen has a FLAG-tag, and His-tag affixed to the carboxy-terminus.

Proteins for use in the methods can be made by methods known in the art. For instance, a transmembrane protein of interest or portion thereof can be encoded by a suitable nucleic acid and expressed in a cell. Suitable nucleic acid molecules encoding the transmembrane protein of interest may be made using standard cloning techniques, site-directed mutagenesis and PCR, as is well known in the art. Suitable expression systems include, for example, constitutive or inducible expression systems in bacteria or yeasts, virus expression systems such as baculovirus, semliki forest virus and lentiviruses, or transient transfection in insect or mammalian cells. Suitable host cells include *E. coli, Lactococcus lactis, Saccharomyces cerevisiae, Schizosaccharomyces pombe, Pichia pastoris, Spodoptera frugiperda* and Trichoplusiani cells. Suitable mammalian host cells include HEK 293, COS, CHO, NS0, DT40. Suitable insect host cells include Sf9 and S2 cells.

In certain embodiments, a protein immunogen comprising a transmembrane protein of interest or portion thereof is expressed in cells, the immunogen protein is produced by the cells and purified to provide a purified protein immunogen for immunization.

In specific embodiments, an animal can be immunized with a transmembrane protein of interest or portion thereof that is encompassed in a carrier such as, for example, a lipid bilayer-membrane scaffold protein complex, a VLP, a cell, an exosome and a liposome.

A "lipid bilayer-membrane scaffold protein complex" means a composition that includes a lipid bilayer in complex with, i.e., bound by, at least one membrane scaffold protein (MSP). Lipid bilayer-membrane scaffold protein complexes have been described. See, e.g., Inagaki, S. et al., Biophysical Characterization of Membrane Proteins in Nanodiscs. *Methods* (2013) 59(3):287-300, the entire content of which is expressly incorporated herein by reference. A lipid bilayer-membrane scaffold protein complex can be formed, for example, as a discoidal phospholipid bilayer surrounded and stabilized by two membrane scaffold proteins. Without being bound by any one theory, complex formation and function are regulated by the MSP to lipid ratio and the length of the MSP. For example, the lipid to MSP ratio can be adjusted to generate homogenous or heterogonous populations of lipid bilayer-membrane scaffold protein complex. Furthermore, in order to provide a native-like environment, the MSP protein should be large enough to form a complex that provides space for both a transmembrane protein or proteins of interest and lipid bilayer formation.

The term "membrane scaffold protein" or "MSP" as used herein refers to a class of amphipathic helical proteins derived from amphipathic apolipoprotein A-I (Apo-AI) as described, for example, in Schuler, M., et al., *Methods Mol Biol.* 2013; 974: 415-433, the entire contents of which is incorporated herein by reference. Membrane scaffold proteins include amphipathic helices comprising hydrophobic residues on the interior side of the helices that contact a lipid hydrophobic tail, and hydrophilic residues that are oriented outwardly (away from the lipid). Membrane scaffold proteins may be of different sizes through a deletion or insertion of one or more helice domains in a portion of an MSP amino acid sequence, which permits formation of lipid bilayer-MSP complex of varying sizes. The structure and function of MSPs are understood to be distinct from the saposin family of lipid binding proteins.

In some instances, lipid bilayer-membrane scaffold protein complexes include at least one membrane scaffold protein selected from the following exemplary MSPs: MSP1, MSP2, MSP1E1, MSP1E2, MSP1E3, MSP1E3D1, MSP1D1, MSP1D2, MSP2N1, MSP2N3 and MSP2N2.

In some embodiments, a membrane scaffold protein is MSP1 comprising the structure FX-H1-H2-H3-H4-H5-H6-H7-H8-H9-H10 [SEQ ID NO: 12], wherein FX is the N-terminal domain of the membrane scaffold protein having the amino acid sequence MGHHHHHHIEGR [SEQ ID NO: 1], H1 is Helix 1 having the amino acid sequence LKLL-DNWDSVTSTFSKLREQLG [SEQ ID NO: 2], H2 is Helix 2 having the amino acid sequence PVTQEFWDN-LEKETEGLRQEMS [SEQ ID NO: 3], H3 is Helix 3 having the amino acid sequence KDLEEVKAKVQ [SEQ ID NO:

4], H4 is Helix 4 having the amino acid sequence PYLDDFQKKWQEEMELYRQKVE [SEQ ID NO: 5], H5 is Helix 5 having the amino acid sequence PLRAELQEGARQKLHELQEKLS [SEQ ID NO: 6], H6 is Helix 6 having the amino acid sequence PLGEEMRDRARAHVDALRTHLA [SEQ ID NO: 7], H7 is Helix 7 having the amino acid sequence PYSDELRQRLAARLEALKENGG [SEQ ID NO: 8], H8 is Helix 8 having the amino acid sequence ARLAEYHAKATEHLSTLSEKAK [SEQ ID NO: 9], H9 is Helix 9 having the amino acid sequence PALEDLRQGLL [SEQ ID NO: 10], and H10 is Helix 10 having the amino acid sequence PVLESFKVSFLSALEEYTKKLNTQ [SEQ ID NO: 11]. In some embodiments, the membrane scaffold protein is MSP2 comprising the structure FX—H1-H2-H3-H4-H5-H6-H7-H8-H9-H10-GT-H1-H2-H3-H4-H5-H6-H7-H8-H9-H10 [SEQ ID NO: 13]. In some embodiments, the membrane scaffold protein is an extended membrane scaffold protein that includes one or more 22 amino acid amphipathic helices inserted into the MSP1 amino acid sequence. In one such embodiment, the extended membrane scaffold protein is MSP1E1 comprising the structure FX—H1-H2-H3-H4-H4-H5-H6-H7-H8-H9-H10 [SEQ ID NO: 14], whereby the amino acid sequence of MSP1 is extended by having a duplicate "H4". In another embodiment, the extended membrane scaffold protein is MSP1E2 comprising the structure FX—H1-H2-H3-H4-H5-H4-H5-H6-H7-H8-H9-H10 [SEQ ID NO: 15], whereby the amino acid sequence of MSP1 is extended by having a duplicate "H4-H5". In yet another embodiment, the extended membrane scaffold protein is MSP1E3 comprising the structure FX—H1-H2-H3-H4-H5-H6-H4-H5-H6-H7-H8-H9-H10 [SEQ ID NO: 16], whereby the amino acid sequence of MSP1 is extended by having a duplicate "H4-H5-H6".

In certain embodiments, the membrane scaffold protein is MSP1D1 comprising the structure TEV-H1Δ(1-11)-H2-H3-H4-H5-H6-H7-H8-H9-H10 [SEQ ID NO: 17], whereby TEV is a modified N-terminal domain having the amino acid sequence MGHHHHHH DYDIPTTENLYFQG [SEQ ID NO: 18], and H1Δ(1-11) is a truncated H1 helical domain having the amino acid sequence STFSKLREQLG [SEQ ID NO: 19]. In some embodiments, the membrane scaffold protein is MSP1D2 comprising the structure TEV-H2-H3-H4-H5-H6-H7-H8-H9-H10 [SEQ ID NO: 20]. In other embodiments, the membrane scaffold protein is MSP2N1 having the structure TEV-H1Δ(1-11)-H2-H3-H4-H5-H6-H7-H8-H9-H10-GT-H1Δ(1-11)—H2-H3-H4-H5-H6-H7-H8-H9-H10 [SEQ ID NO: 21]. In another embodiment, the membrane scaffold protein is MSP2N2 having the structure TEV-H1Δ(1-11)-H2-H3-H4-H5-H6-H7-H8-H9-H10-GT-H2-H3-H4-H5-H6-H7-H8-H9-H10 [SEQ ID NO: 22]. In yet another embodiment, the membrane scaffold protein is MSP2N3 having the structure TEV-H1Δ(1-11)-H2-H3-H4-H5-H6-H7-H8-H9-H10-GT-H1Δ(1-17)-H2-H3-H4-H5-H6-H7-H8-H9-H10 [SEQ ID NO: 24], whereby H1Δ(1-17) is a truncated H1 helical domain having the amino acid sequence REQLG [SEQ ID NO: 23].

In certain embodiments, the lipid bilayer-membrane scaffold protein complex includes two MSPs. In one embodiment, the lipid bilayer-membrane scaffold protein complex is a discoidal phospholipid bilayer surrounded by two MSPs (e.g., two molecules of an MSP) in a belt-like manner. In one embodiment, the lipid bilayer-membrane scaffold protein complex is a discoidal phospholipid bilayer surrounded by two molecules of MSP1E3D1.

In some embodiments, the lipid bilayer-membrane scaffold protein complex includes a detectable label. In certain embodiment, the lipid bilayer-membrane scaffold protein complex contains at least two labeled membrane scaffold proteins and a plurality of lipids. In specific embodiments, the lipid bilayer-membrane scaffold protein complex contains two labeled membrane scaffold proteins and a lipid bilayer. In some embodiments, the labeled membrane scaffold proteins are the same or different. The detectable label can be any detectable label known in the art. For example, a detectable label includes a fluorescent molecule, a His-Tag and a FLAG-Tag. In exemplary embodiments, one or more of the membrane scaffold protein(s) are labeled with a detectable marker such as a Bir-A tag or Avi-tag for biotinylation. In a specific embodiment, all MSPs in the lipid bilayer-membrane scaffold protein complex are biotinylated. Biotinylation can be carried out by, for example, chemically biotinylating the membrane scaffold protein(s) or by genetically introducing an Avi-tag or Bir-A tag into the MSP nucleic acid coding sequence and producing the modified protein using known techniques.

The lipid bilayer portion of the lipid bilayer-membrane scaffold protein complex is reconstructed. The lipids can form a bilayer of lipids such as, for example, sphingolipids and/or phospholipids. The lipid composition of a complex can vary, for example, based on the native cell type of a particular transmembrane protein or proteins of interest to be included in the complex. For instance, the *E. coli* membrane contains 70-80% phosphatidyl ethanolamine, 15-20% phosphatidyl glycerol and 5% cardiolipin, whereas rat hepatocyte membranes are composed of 14-20% phosphatidyl ethanolamine, 32-47% phosphatidyl choline, 8% phosphatidyl inositol, 4-8% phosphatidyl serine, and 13-14% sphingomyelin. See Inagaki, S. et al., *Methods* (2013) 59(3):287-300. Therefore, the lipid composition of the lipid bilayer-membrane scaffold protein complex can include a single type of lipid or more than a single type of lipid. In certain embodiments, the lipids that form the lipid bilayer-membrane scaffold protein complex are synthetic or recombinantly produced lipids.

In some embodiments, the lipid bilayer is comprised of one or more of the following lipids: sphingomyelin, phosphatidylcholine, and derivatives thereof. In a specific embodiment, the lipid bilayer is comprised of 1-dioleoyl phosphatidylcholine (DOPC), 1-palmitoyl 2-oleoyl phosphatidylcholine (POPC), 1-stearoyl-2-oleoyl-phosphatidylcholine (SOPC), phosphatidylethanolamines (PE), and phosphatidylserine (PS), palmitoyl-2-oleoyl-sn-glycero-3-phospho-(1'-rac-glycerol) (POPG), 1-palmitoyl-2-oleoyl-sn-glycero-3-phospho-L-serine (POPS), and phosphatidylinositol (PI) or combinations thereof. In certain embodiments, the lipid bilayer includes a plurality of POPC phospholipids.

In some embodiments, the lipid bilayer-membrane scaffold protein complex includes lipids that form a discoidal phospholipid bilayer around the membrane scaffold protein (s) comprising a plurality of one or more of the following lipids: POPC, POPG and POPS. In specific embodiments, the lipid bilayer-membrane scaffold protein complex includes a plurality of POPC lipids that form a discoidal phospholipid bilayer around two membrane scaffold proteins. In one such embodiment, the ratio of MSP to lipid is from between 1:100 and 1:150, 1:110 and 1:140, 1:120 and 1:140, 1:120 and 1:140, 1:120-1:130, and 1:125 and 1:135, inclusive. In other embodiments, the ratio of MSP to lipid is 1:100, 1:110, 1:111, 1:112, 1:113, 1:114, 1:115, 1:116, 1:117, 1:118, 1:119, 1:120, 1:121, 1:122, 1:123, 1:124, 1:125, 1:126, 1:127, 1:128, 1:129, 1:130, 1:131, 1:132, 1:133, 1:134, 1:135, 1:136, 1:137, 1:138, 1:139, 1:140, 1:141. 1:142, 1:143, 1:144, 1:145, 1:146, 1:147, 1:148, 1:149 or 1:150, inclusive.

In certain instances, a lipid bilayer-membrane scaffold protein complex also includes at least one antigen. In specific embodiments, the antigen is a transmembrane protein of interest, or a portion thereof. In some embodiments, the transmembrane protein of interest is a full-length transmembrane protein of interest, a truncated transmembrane protein of interest, a chimeric transmembrane protein of interest. In some embodiments, the truncated transmembrane protein of interest does not include, one or more extracellular loop domains, an amino-terminal and/or carboxy-terminal portion of the full-length transmembrane protein of interest. In particular embodiments, the truncated transmembrane protein does not include the amino-terminal portion of the full-length transmembrane protein of interest. In certain embodiments, the truncated transmembrane protein of interest includes at least an entire transmembrane portion of the transmembrane protein of interest. In other embodiments, the truncated transmembrane protein does not include the carboxy-terminal portion of the full-length transmembrane protein of interest. In one embodiment, the truncated transmembrane protein does not include an extracellular loop domain of the full-length transmembrane protein of interest. In some embodiments, the truncated protein includes an extracellular domain of a transmembrane protein of interest such as an N-terminal extracellular domain, a C-terminal extracellular domain, and/or an extracellular loop domain between one or more membrane spanning domains of the transmembrane protein of interest. In other embodiments, the antigen is a chimeric transmembrane protein of interest, or a portion thereof as described herein.

In some embodiments, a lipid bilayer-membrane scaffold protein complex that comprises an antigen, such as a transmembrane protein of interest or a portion thereof, includes a single molecule of the antigen (e.g., one copy of a transmembrane protein or a portion thereof per lipid bilayer-MSP complex or per nanodisc). In some embodiments, a lipid bilayer-membrane scaffold protein complex that comprises an antigen includes multiple molecules of the antigen (e.g., multiple copies of a transmembrane protein or a portion thereof per lipid bilayer-MSP complex or per nanodisc).

The formation of lipid bilayer-membrane scaffold protein complexes, including those that encompass a transmembrane protein of interest or portion thereof, can be carried out using methods known in the art. See, for example, Bayburt T H, et al., *Arch Biochem Biophys.* (2006) 450:215-222, the entire contents of which is incorporated herein by reference. Generally, the formation of lipid bilayer-membrane scaffold protein complexes includes the self-assembly of complexes by mixing lipid, MSP and, where applicable, a transmembrane protein. Typically, a transmembrane protein is purified by using one or more detergents. In some embodiments, a purified transmembrane protein is mixed with lipid and MSP to form a lipid bilayer-membrane scaffold protein complex comprising the transmembrane protein. In some embodiments, a purified transmembrane protein is provided in the presence of one or more detergents (e.g., in a detergent solubilized fraction), and mixed with lipid and MSP, and then the one or more detergents are removed to induce formation of the complex structure.

In some instances, a purification step can be used to separate complexes that include the protein of interest from those that do not (i.e., empty complexes). Purification can be achieved by incorporating one or more detectable labels on the transmembrane protein of interest included in the complex, such as an affinity tag, and selecting for the one or more labels. Exemplary detectable labels for use as affinity tags include, but are not limited to, a His-tag that can be recognized by immobilized metal affinity chromatography (IMAC), a FLAG-tag for FLAG M1 anti-FLAG immunoaffinity chromatography, and a 1D4 tag using 1D4 resin. Size-exclusion chromatography can also be utilized by conducting, for example, SDS page and Western Blotting analysis to identify and/or confirm the presence of lipid bilayer-membrane scaffold protein complexes that include a transmembrane protein of interest or portion thereof. In embodiments where the transmembrane protein of interest and the MSP both include a detectable label, at least one label on the MSP and one label on the transmembrane protein of interest can be different.

In specific embodiments, a lipid bilayer-membrane scaffold protein complex containing a transmembrane protein of interest or portion thereof can been formed by first solubilizing the transmembrane protein of interest in a detergent (such as, for example, N-Dodecyl-β-D-maltoside (DDM)) and then mixing with cholate-solubilized phospholipid and membrane scaffold protein, followed by removal of the detergents. In some examples, the detergent can be extracted from the mixture using biobeads, which permits the assembly of discoidal lipid-bilayer membrane scaffold protein complexes that integrate the purified transmembrane protein of interest. Discoidal lipid-bilayer membrane scaffold protein complexes that incorporate the transmembrane protein of interest can then be isolated from discoidal lipid-bilayer membrane scaffold protein complexes that do not include a transmembrane protein using affinity purification beads. For example, beads with an anti-"tag" antibody (e.g., FLAG-tag, His-tag, HA-tag and the like, such tags being well-known in the art) when the transmembrane protein of interest contains the corresponding "tag" sequence at its c-terminus or n-terminus. Further purification could be achieved by size exclusion chromatography.

In certain instances, an immunogen embedded in a lipid bilayer-membrane scaffold protein complex is administered to an animal at a concentration of at least 0.1 mg/mL, at least 0.2 mg/mL, at least 0.3 mg/mL, at least 0.4 mg/mL, at least 0.5 mg/mL, at least 0.6 mg/mL, at least 0.7 mg/mL, at least 0.8 mg/mL, at least 0.9 mg/mL, at least 1.0 mg/mL, at least 2.0 mg/mL, at least 3.0 mg/mL, at least 4.0 mg/mL, at least 5.0 mg/mL, at least 10.0 mg/mL or greater. In certain embodiments, the immunogen is injected into an animal at a concentration of 0.2 mg/mL to 20 mg/mL, 0.5 mg/mL to 15 mg/mL, 0.5 mg/mL to 10 mg/mL, 0.5 mg/mL to 7.0 mg/mL, 0.5 mg/mL to 5.0 mg/mL, 1.0 mg/mL to 10 mg/mL, 1.0 mg/mL to 5.0 mg/mL, 1.0 mg/mL to 4.0 mg/mL, 1.0 mg/mL to 3.0 mg/mL, 1.0 mg/mL to 2.0 mg/mL, or 2.0 mg/mL to 5.0 mg/mL, inclusive. In specific embodiments, the immunogen is injected into an animal at a concentration of 0.5 mg/mL, 0.55 mg/mL, 0.6 mg/mL, 0.65 mg/mL, 0.7 mg/mL, 0.75 mg/mL, 0.8 mg/mL, 0.85 mg/mL, 0.9 mg/mL, 0.95 mg/mL, 1.0 mg/mL, 1.5 mg/mL, 1.6 mg/mL, 1.8 mg/mL, 2.0 mg/mL, 2.5 mg/mL, 3.0 mg/mL, 3.5 mg/mL, 4.0 mg/mL, 4.5 mg/mL, 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10.0 mg/mL, 12.0 mg/mL, 15.0 mg/mL, 20.0 mg/mL, or greater. In one embodiment, the transmembrane protein of interest immunogen embedded in a lipid bilayer-membrane scaffold protein complex is injected into an animal at a concentration of 0.5 mg/mL.

In certain embodiments, an animal can be immunized with cells expressing the immunogen, such as irradiated cells. In one particular embodiment, the animal can be immunized with cells that express a transmembrane protein of interest immunogen, a modified version thereof, or a portion thereof as described herein.

In some embodiments, an animal can be immunized with a VLP or exosome that expresses a transmembrane protein of interest in the animal. In specific embodiments, the animal can be immunized with a VLP that includes a nucleic acid that encodes for a transmembrane protein of interest, modified version thereof, or a portion thereof.

In some instances, an animal is immunized with two or more immunogens such as, for example, a protein or peptide, a modified protein or peptide, a nucleic acid, a modified nucleic acid, a VLP and a lipid bilayer-membrane scaffold protein complex encompassing a transmembrane protein of interest or portion thereof as described herein.

The animal to be immunized can be any animal. In certain embodiments, the animal is a mammal. In some embodiments, the mammal is a mouse, rat, goat, human, hamster, pig, monkey or guinea pig. In some embodiments, the mammal is not a human. In particular embodiments, the non-human mammal is a mouse, rat or goat. In a specific embodiment, the mammal is a mouse. In another embodiment the mammal is a human such as, for example, a human that has been exposed to an immunogen.

In some instances, the immunized animal is genetically-engineered. Genetic modification can be carried out by known methods, such as those used to delete or interrupt the gene that encodes protein. For example, the animal can be genetically-engineered such that the animal does not express the transmembrane protein of interest (i.e., antigen) from an endogenous gene locus (e.g., a knock-out). By way of example, a genetically-engineered non-human mammal is a mouse that is mouse incapable of expressing an endogenous mouse transmembrane protein of interest, e.g., as a result of the genetic modification to the endogenous mouse transmembrane protein's gene locus or an inactivation (e.g., deletion in full or in part) of the endogenous gene.

In certain embodiments, the genetically-engineered animal is non-human mammal such as, for example, a mouse, goat or rat, that includes in their genome (e.g., via cross-breeding or multiple gene targeting strategies): (i) a humanized immunoglobulin heavy chain locus comprising one or more human variable heavy chain gene segments; (ii) a humanized immunoglobulin heavy chain locus comprising one or more human variable light chain gene segments; and/or (iii) a humanized immunoglobulin light chain locus (e.g., κ and/or λ) comprising one or more human variable light chain gene segments. The term "humanized", as used herein, includes modified to include human sequences. For example, a humanized locus is a locus (e.g., an endogenous locus) that has been modified to include human sequences (e.g., gene segments or genes).

In some embodiments, the genetically-engineered animal is a non-human mammal such as, for example, a mouse, goat or rat, that includes in their genome a humanized immunoglobulin heavy chain locus comprising one or more human variable heavy chain gene segments.

In some embodiments, the genetically-engineered animal is a non-human mammal such as, for example, a mouse, goat or rat, that includes in their genome a humanized immunoglobulin light chain locus comprising one or more human variable light chain gene segments.

In some embodiments, the genetically-engineered animal is a non-human mammal such as, for example, a mouse, goat or rat, that includes in their genome a humanized immunoglobulin light chain locus (e.g., κ and/or λ) comprising one or more human variable light chain gene segments. In one embodiment, the genetically-engineered animal comprises a humanized immunoglobulin light chain locus comprising one or more human kappa variable (Vκ) gene segments. In another embodiment, the genetically-engineered animal comprises a humanized immunoglobulin light chain locus comprising one or more human lambda variable (Vλ) gene segments.

In some embodiments, the genetically-engineered animal that comprises a nucleic acid sequence encoding a human immunoglobulin heavy chain variable region ($V_H$) and/or a nucleic acid sequence encoding a human immunoglobulin light chain variable region ($V_L$), can also lack the endogenous gene encoding the transmembrane protein of interest.

In other instances, the animal is a "wild-type" animal, which expresses an endogenous homolog of the transmembrane protein of interest.

In some embodiments, a genetically-engineered animal (e.g., rat or mouse), produces an antibody comprising, inter alia, heavy chains, where each heavy chain comprises a human heavy chain variable domain operably linked to a rodent (e.g., rat or mouse) heavy chain constant domain. In some embodiments, a genetically-engineered animal (e.g., rat or mouse), produces an antibody comprising, inter alia, where each immunoglobulin chain comprises a human light chain variable domain operably linked to a rodent (e.g., rat or mouse) heavy chain constant domain. In some embodiments, a genetically-engineered animal (e.g., rat or mouse), produces an antibody comprising, inter alia, κ light chains, where each κ light chain comprises a human κ light chain variable domain operably linked to a rodent (e.g., rat or mouse) κ light chain constant domain. In some embodiments, a genetically-engineered animal (e.g., rat or mouse), produces an antibody comprising, inter alia, λ light chains, where each λ light chain comprises a human λ light chain variable domain operably linked to a human λ light chain constant domain. In some embodiments, a genetically-engineered animal (e.g., rat or mouse), produces an antibody comprising, inter alia, light chains, where each light chain comprises a human λ light chain variable domain operably linked to a rodent (e.g., rat or mouse) κ light chain constant domain. In some embodiments, a genetically-engineered animal (e.g., rat or mouse), produces an antibody comprising, inter alia, λ light chains, where each λ light chain comprises a human λ light chain variable domain operably linked to a rodent (e.g., rat or mouse) λ light chain constant domain.

In some embodiments, a non-human mammal (e.g., rat or mouse) described herein is as described in e.g., U.S. Pat. Nos. 8,502,018, 8,642,835, 8,697,940, 8,791,323, 9,226,484, and WO2019/113065; all of which are incorporated herein by reference in their entireties. Breeding (or "cross", or "cross-breeding") can be done following protocols readily available in the art; see, e.g., JoVE Science Education Database. *Lab Animal Research, Fundamentals of Breeding and Weaning*, JoVE, Cambridge, MA, (2018) (video article); *Breeding Strategies for Maintaining Colonies of Laboratory Mice, A Jackson Laboratory Resource Manual*, ©2007 The Jackson Laboratory; all incorporated herein by reference. Alternatively, an engineered Igλ light chain locus can be engineered into an ES cell comprising a humanized IgH locus and/or a humanized Igκ locus, and the resulting ES cell is used to generate a genetically-engineered animal, or a genetically-engineered animal comprising a humanized Igλ light chain locus may be bred with another genetically-engineered animal comprising a humanized IgH locus and/or a humanized Igκ locus. Various genetically-engineered animals comprising a humanized IgH locus and/or a humanized Igκ locus are known, e.g., a VELOCIMMUNE® strain (see, e.g., U.S. Pat. Nos. 8,502,018, 8,642,835; incorporated herein by reference in their entireties), a XENOMOUSE™ strain (see, e.g., Mendez, M. J. et al., 1997, Nat. Genetics 15(2):146-56 and Jakobovits, A. et al., 1995, Ann. NY Acad. Sci. 764:525-35, incorporated by reference in their entireties).

In some embodiments, genetically-engineered animals described herein comprise a limited immunoglobulin light chain locus as described in U.S. Pat. Nos. 9,796,788; 9,969,814; U.S. Patent Application Publication Nos. 2011/0195454 A1, 2012/0021409 A1, 2012/0192300 A1, 2013/0045492 A1, 2013/0185821 A1, 2013/0302836 A1; International Patent Application Publication Nos. WO 2011/097603, WO 2012/148873, WO 2013/134263, WO 2013/184761, WO 2014/160179, WO 2014/160202; all of which are hereby incorporated by reference in their entireties. In some embodiments, rodent animals described herein comprise an immunoglobulin light chain locus as described in WO2019/113065, WO2017214089, US20180125043 and U.S. Pat. Nos. 9,035,128; 9,066,502; 9,163,092; 9,150,662; 9,334,333; 9,006,511; 9,029,628; 9,206,261; 9,012,717; 9,394,373; 9,206,262; 9,206,263; 9,226,484; 9,540,452; and 9,399,683, all of which are hereby incorporated by reference in their entireties.

Once an animal has been immunized the animal's immune response to the immunogen is monitored using an antigen-specific immunoassay. A humoral immune response in an animal can be determined based on titers of antibodies in the serum specific for the transmembrane protein of interest (antigen). A variety of assays can be employed to determined antibody titers, including ELISA and flow cytometry based assays (see, e.g., David H. Margulies, *Induction of Immune Responses, Current Protocols in Immunology*, 89, 1, (2.0.1-2.0.3) (2010); Henri V. van der Heyde et al., "Analysis of antigen-specific antibodies and their isotypes in experimental malaria," *Cytometry*, Vol. 71A (4): 242-250 (2007); both incorporated herein by reference. In some embodiments, an assay utilizes cells that express or engineered to express the transmembrane protein of interest on the cell surface, and antibody titers can be determined by measuring antibody binding to the cells.

When an appropriate immune response has been achieved, a population of cells is collected from the immunized animal. The cells can be collected from a number of sources, including, but not limited to, spleen, lymph node, bone marrow and peripheral blood of the immunized animal. In one embodiment, the cells are a population of cells obtained from the spleen of an immunized animal, i.e., a population of splenocytes. In some embodiments, the population of cells is a heterogeneous population of cells, which contains cells from different tissues, organs or areas of the immunized animal. In specific embodiments, the population of cells is a homogenous population of cells, which are obtained from one organ such as the spleen of the immunized animal. In one embodiment, the population of cells includes tissue-derived cells from one or more of the spleen, lymph node and bone marrow. In other embodiments, the population of cells is obtained from the blood of immunized animals.

The cells collected from the immunized animal include "antibody-producing cells", which refers to cells that express antibody either naturally (as the result of B cell activation), or as the result of recombinant technology and genetic engineering (such as hybridoma cells). The term "antibody-producing cells", therefore, encompasses immune cells, such as lymphocytes. In certain, non-limiting, examples the lymphocytes can be of antigen-dependent B cell lineage, including memory B-cells, plasmablasts and terminally differentiated plasma cells that express antibody, as well as recombinant cells such as hybridomas and non-lymphoid cells engineered to express antibodies. Furthermore, "antibody-producing cells" encompass cells in which the antibody expressed is bound to or anchored in the cell membrane, i.e., cell surface antibodies, as well as cells that secrete antibody.

In certain embodiments, a population of antibody-producing cells is from spleen, lymph node, bone marrow or peripheral blood of an immunized animal. In specific embodiments, a population of antibody-producing cells includes peripheral blood cells, B cells, plasma cells, plasma cell myelomas, or a combination thereof. In some embodiments, the population of antibody-producing cells includes recombinant cells such as, for example, hybridomas. In specific embodiments, the population of antibody-producing cells is a population of lymphocytes such as, for example, B cells. In one embodiment, the population of antibody-producing cells is composed of memory B cells.

Also, in some instances, further antibody-producing cells may be derived from a starting population of antibody-producing cells obtained by the methods of the disclosure. As such, cell lines, plasma cells, memory B cells, hybridomas, plasma cell myelomas and recombinant antibody-expressing cells may be derived or obtained from antibody-producing cells. For example, antibody-producing cells may be fused to myeloma cells to make hybridomas, or otherwise immortalized, such as infected with a virus (e.g., EBV), or may be differentiated by cell sorting techniques based on protein markers expressed by particular B cell types.

In specific embodiments, the term "antibody-producing cells" means cells that express antibody that binds to a transmembrane protein of interest. In some embodiments, the antibody that binds to the transmembrane protein of interest is located on the cell surface. In certain instances, the population of antibody-producing cells is a heterogeneous population of antibody-producing cells, which contains antibody-producing cells that express antibody to more than one antigen. In one particular embodiment, the population of antibody-producing cells is a heterogeneous population of antibody-producing cells, which contains antibody-producing cells that express antibody that binds to a transmembrane protein of interest and at least one other antigen. In other embodiments, the population of antibody-producing cells can be a homogenous population of antibody-producing cells, which contains antibody-producing cells that express antibody that bind to only one antigen. In a specific embodiment, the population of antibody-producing cells is a homogenous population of antibody-producing cells, which contains antibody-producing cells that express antibody that binds to a transmembrane protein of interest.

As shown in Tables 1-5, immunization of animals with various different immunogens and combinations of immunogens resulted in the generation of antibody-producing cells, including populations of antibody-producing cells that express antibody that binds to a transmembrane protein of interest. Tables 1-5 also show that immunization of genetically-engineered animals that do not express an endogenous gene encoding the transmembrane protein of interest generated antibody-producing cells that express antibody that binds to a transmembrane protein of interest.

Collecting Antibody Producing Cells that Express Antibody to a Transmembrane Protein of Interest.

As described herein, obstacles to the generation of antibodies to transmembrane proteins include the inability to provide sufficient amounts of conformationally accurate transmembrane protein antigens to antibodies or cells that produce antibodies to a transmembrane protein of interest. For example, purified endogenous transmembrane proteins become conformationally compromised when isolated from their natural membrane environment and current lipid-based and cell-based membrane preparations result in high levels of non-specific binding, are difficult to formulate, and often provide a subset of unfolded or improperly folded transmembrane protein antigen.

The disclosure overcomes such obstacles by utilizing lipid bilayer-membrane scaffold protein complexes to present transmembrane protein antigens to antibodies produced by antibody-producing cells. More specifically, the disclosure employs complexes that include a transmembrane protein of interest, as well as lipids and membrane scaffold proteins commonly found in the membranes of naturally occurring cells, to present the transmembrane protein in its natural conformation to an antibody. As such, lipid bilayer-membrane scaffold protein complexes are used in the present methods to identify and collect a particular subset of antibodies (or cells that express antibody) in a population that bind to an epitope on a transmembrane protein that is accessible in nature.

Once a lipid bilayer-membrane scaffold protein complex including a transmembrane protein of interest has been formed, the complex can be used as a sorting agent to detect and isolate a population of antibody-producing cells that express antibody that binds to the transmembrane protein of interest. For example, a heterogeneous population of antibody-producing cells can be obtained from a mammal immunized as described herein, and then the population of antibody-producing cells can be contacted with a lipid bilayer-membrane scaffold protein complex that presents a transmembrane protein of interest antigen to the antibody produced by the cells. The complex and population of antibody-producing cells can then be incubated to permit binding between the transmembrane protein of interest presented by the complex and an antibody produced by the cells. Binding between the antibody and transmembrane protein of interest can then be detected and bound cells can be collected for further use.

In some instances, a population of antibody-producing cells obtained from an immunized animal can be a heterogeneous population of antibody-producing cells, which contains antibody-producing cells that express antibody to more than one antigen. In particular embodiments, the population of antibody-producing cells is a heterogeneous population of antibody-producing cells, which contains certain antibody-producing cells that express antibody that binds to a transmembrane protein of interest and certain antibody-producing cells that express antibody that binds to at least one other antigen. In certain embodiments, the heterogeneous population of antibody-producing cells is comprised of at least 0.01%, at least 0.1%, at least 0.5%, at least 1.0%, at least 1.5%, at least 2.0%, at least 3.0%, at least 4.0%, at least 5.0%, at least 10%, at least 20%, at least 30%, at least 40%, at least 50%, at least 60%, at least 70%, at least 80, at least 90% or greater antibody-producing cells that express antibody that binds to a transmembrane protein of interest.

In other embodiments, the population of antibody-producing cells can be a homogenous population of antibody-producing cells, which contains antibody-producing cells that express antibody that bind to only one antigen. In a specific embodiment, the population of antibody-producing cells is a homogenous population of antibody-producing cells, which contains antibody-producing cells that express antibody that binds to a transmembrane protein of interest. In certain embodiments, the homogenous population of antibody-producing cells is comprised of at least 70%, at least 80, at least 90%, at least 91%, at least 92%, at least 93%, at least 94%, at least 95%, at least 96%, at least 97%, at least 98%, at least 99% or greater antibody-producing cells that express antibody that binds to a transmembrane protein of interest.

In certain embodiments, B cells can be detected and collected from a heterogeneous population of cells obtained from an immunized animal at the same time as antibody-producing cells are obtained, to provide a population of antibody-producing B cells. In some embodiments, B cells can be obtained from a heterogeneous population of cells obtained from an immunized animal prior to obtaining antibody-producing cells from the heterogeneous population of cells. In yet another embodiment, B cells can be detected in a population of antibody-producing cells obtained from an immunized animal to obtain a population of antibody-producing B cells.

In one particular embodiment, antibody-producing B cells expressing antibodies to a transmembrane protein of interest can be detected in a heterogonous population of cells obtained from immunized animals and isolated by FACS based on cell-surface B cell markers.

B cell markers are known in the art. For example, applicable B cell markers that can be detected through the use of FACS include, but are not limited to, IgG, IgM, IgE, IgA, IgD, CD1, CDS, CD19, CD20, CD21, CD22, CD23, CD24, CD25, CD27, CD30, CD38, CD40, CD78, CD80, CD138, CD319, TLR4, IL-6, PDL-2, CXCR3, CXCR4, CXCR5, CXCR6, IL-10 and TGFβ. In a specific embodiment, B cells can be detected using labels specific to IgG, IgM or a combination thereof. In one embodiment, antibody-producing B cells are detected using antibodies specific to IgG.

In a specific embodiment, following immunization, splenocytes are harvested from an immunized animal. Following removal of red blood cells, a population of IgG$^+$-antigen-positive B cells from the immunized animals is isolated from a heterogeneous population of cells using the methods described herein. For example, splenocytes are contacted with anti-IgG antibody and washed to remove excess unbound cells and antibody. Cells are then stained with a fluorescent antibody (i.e., secondary antibody) that binds to a labeled B cell marker (such as, anti-IgG antibody). The stained cells can then be analyzed by flow cytometry and isolated for further use, as set forth herein.

In some embodiments of the methods, peripheral blood mononuclear cells (PBMCs) are harvested from a mammal known to have humoral immunity to an antigen of interest. IgG$^+$, antigen-positive B cells expressing antibodies that recognize an antigen of interest can then be isolated for further processing in accordance with the methods of the disclosure.

In some embodiment of the methods, a population of antibody-producing cells includes antibody-producing B cells. In one such embodiment, a population of antibody-producing includes antibody-producing B cells that express antibodies to a transmembrane protein of interest, which can be detected in a heterogeneous population of cells obtained from immunized animals and isolated by contacting the heterogeneous population of cells with a lipid bilayer-membrane scaffold protein complex presenting the transmembrane protein of interest and a molecule that binds to a B cell marker, such as for example an antibody that binds to a B cell surface marker. For example, following immunization, splenocytes are harvested from an immunized animal. Following removal of red blood cells, a heterogeneous population of cells is incubated with a labeled anti-IgG antibody in order to permit binding between the anti-IgG antibody and IgG$^+$-positive B cells in the heterogeneous population of cells. At the same time, or subsequent to, or prior to incubation with the labeled anti-IgG antibody the heterogeneous population of cells are incubated with labeled lipid bilayer-membrane scaffold protein complex presenting the transmembrane protein of interest in order to permit binding of the transmembrane protein to antibody produced by the cells. A population of antibody-producing B cells that express antibody to the transmembrane protein of interest can then be obtained by, for example, flow cytometry to detect and isolate (collect) cells bound to both the labeled anti-IgG antibody (B cells) and labeled lipid bilayer-membrane scaffold protein complex.

In some instances, the methods include immunizing an animal as described herein.

In instances that include contacting or incubating a population of cells such as, for example, a population of antibody-producing cells with a lipid bilayer-membrane scaffold protein complex the a lipid bilayer-membrane scaffold protein complex is provided to the cell media at a concentration of at least 0.1 mg/mL, at least 0.2 mg/mL, at least 0.3 mg/mL, at least 0.4 mg/mL, at least 0.5 mg/mL, at least 0.6 mg/mL, at least 0.7 mg/mL, at least 0.8 mg/mL, at least 0.9 mg/mL, at least 1.0 mg/mL, at least 2.0 mg/mL, at least 3.0 mg/mL, at least 4.0 mg/mL, at least 5.0 mg/mL, at least 10.0 mg/mL or greater. In certain embodiments, the complex is provide to the cells at a concentration of 0.2 mg/mL to 20.0 mg/mL, 0.2 mg/mL to 15.0 mg/mL, 0.2 mg/mL to 10 mg/mL, 0.2 mg/mL to 7.0 mg/mL, 0.2 mg/mL to 5.0 mg/mL, 0.5 mg/mL to 10.0 mg/mL, 0.5 mg/mL to 7.0 mg/mL, 0.5 mg/mL to 5.0 mg/mL, 1.0 mg/mL to 10.0 mg/mL, 1.0 mg/mL to 7.0 mg/mL, or 1.0 mg/mL to 5.0 mg/mL, inclusive. In specific embodiments, the complex is provide to the cells at a concentration of 0.1 mg/mL, 0.2 mg/mL, 0.3 mg/mL, 0.4 mg/mL, 0.5 mg/mL, 0.55 mg/mL, 0.6 mg/mL, 0.65 mg/mL, 0.7 mg/mL, 0.75 mg/mL, 0.8 mg/mL, 0.85 mg/mL, 0.9 mg/mL, 0.95 mg/mL, 1.0 mg/mL, 1.5 mg/mL, 1.6 mg/mL, 1.8 mg/mL, 2.0 mg/mL, 2.5 mg/mL, 3.0 mg/mL, 3.5 mg/mL, 4.0 mg/mL, 4.5 mg/mL, 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, 10.0 mg/mL, 12.0 mg/mL, 15.0 mg/mL, 20.0 mg/mL, or greater.

In one aspect of the methods, the immunized animal is a non-human animal or a genetically-engineered non-human animal such as, for example, a mouse or a rat, that is immunized with a human transmembrane protein of interest or a portion thereof, a nucleic acid sequence encoding the same or a combination thereof.

In certain embodiments of the methods, a non-human animal or a genetically-engineered non-human animal such as, for example, a mouse or a rat, is immunized with a full-length human transmembrane protein of interest, a nucleic acid sequence encoding the same or a combination thereof, and splenocytes are isolated from the immunized non-human animal (e.g., rat or mouse) and are incubated with labeled antibodies to a B cell marker (e.g., fluorochrome-labeled anti-IgG antibody) to identify a population of B cells. The cells are also incubated with biotinylated lipid bilayer-membrane scaffold protein complex that encompasses the full-length human transmembrane protein to permit binding between the human transmembrane protein of interest (antigen) presented by the complex and antibody produced by the cells. Subsequently, the cells are incubated with PE-streptavidin to enable streptavidin binding to each of the biotin-labeled (e.g., Bir-A) membrane scaffold proteins in the lipid-bilayer-membrane scaffold protein complex. Cells can then be washed. PE fluorescence and signals from bound B cells (e.g., fluorochrome-labeled anti-IgG signals) can be detected by FACS to identify and collect a homogeneous population of antibody-producing B cells that express antibody that binds an epitope on the full-length human transmembrane protein of interest.

In some embodiments of the methods, a non-human animal or a genetically-engineered non-human animal such as, for example, a mouse or a rat, is immunized with a full-length human transmembrane protein of interest, a nucleic acid sequence encoding the same or a combination thereof, and splenocytes are isolated from the immunized non-human animal (e.g., rat or mouse) and are incubated with labeled antibodies to a B cell marker (e.g., fluorochrome-labeled anti-IgG antibody) to identify a population of B cells. The cells are also incubated with biotinylated lipid bilayer-membrane scaffold protein complex that encompasses a portion of the human transmembrane protein, such as a truncated human transmembrane protein, to permit binding between an epitope on the portion of the human transmembrane protein of interest (antigen) presented by the complex and antibody produced by the cells. Subsequently, the cells are incubated with PE-streptavidin to enable streptavidin binding to each of the biotin (Bir-A) labeled membrane scaffold proteins in the lipid-bilayer-membrane scaffold protein complex Cells can then be washed. PE fluorescence and signals from bound B cells (e.g., fluorochrome-labeled anti-IgG signals) can be detected by FACS to identify and collect a homogeneous population of antibody-producing B cells that express antibody that binds an epitope on the antigen presented by the complex.

In embodiments of the methods that include a lipid-bilayer-membrane scaffold protein complex comprising a portion of the transmembrane protein of interest, the transmembrane protein presented by the complex does not include the full-length transmembrane protein of interest. In some embodiments, the transmembrane protein of interest is a truncated transmembrane protein as described herein. In certain embodiments, the truncated transmembrane protein of interest includes at least an entire transmembrane portion of the transmembrane protein of interest. In certain embodiments, the truncated transmembrane protein does not include, one or more extracellular loop domains, an amino-terminal and/or carboxy-terminal portion of the full-length transmembrane protein of interest. In some embodiments, the truncated protein includes an extracellular domain of a transmembrane protein of interest such as an N-terminal extracellular domain, a C-terminal extracellular domain, and/or an extracellular loop domain between one or more membrane spanning domains of the transmembrane protein of interest. In a particular embodiment, the truncated transmembrane protein does not include the amino-terminal portion of the full-length transmembrane protein of interest. In another embodiment, the truncated transmembrane protein does not include the carboxy-terminal portion of the full-length transmembrane protein of interest. In some embodiments, the truncated transmembrane protein does not include an extracellular loop domain of the full-length transmembrane protein of interest.

In other embodiments of the methods, a non-human animal or a genetically-engineered non-human animal such as, for example, a mouse or a rat, is immunized with a full-length human transmembrane protein of interest, a nucleic acid sequence encoding the same or a combination thereof. Splenocytes are isolated from the immunized non-human animal (e.g., rat or mouse) and are incubated with labeled antibodies to a B cell marker (e.g., fluorochrome-labeled anti-IgG antibody) to identify a population of B cells. The cells are also incubated with biotinylated lipid bilayer-membrane scaffold protein complex that encompasses a chimeric transmembrane protein that includes a portion of the human transmembrane protein of interest and a portion of a non-human homolog of the transmembrane protein of interest to permit binding between a human portion of the chimeric transmembrane protein of interest (antigen) presented by the complex and antibody produced by the cells. Cells can then be washed. PE fluorescence and signals from bound B cells (e.g., fluorochrome-labeled anti-IgG signals) can be detected by FACS to identify and collect a homogeneous population of antibody-producing B cells that express antibody that binds an epitope on a human portion of the chimeric transmembrane protein of interest.

In embodiments of the methods that include the use of a chimeric transmembrane protein of interest, the chimeric protein can include portions of a transmembrane protein of interest from two different species as described herein. For example, a chimeric transmembrane protein can include one or more portions of a human transmembrane protein operably linked to one or more portions of a non-human homolog of the transmembrane protein of interest. In some instances, the chimeric transmembrane protein includes an extracellular domain of a transmembrane protein of interest such as an N-terminal extracellular domain, a C-terminal extracellular domain, and/or an extracellular loop domain between one or more membrane spanning domains of the transmembrane protein of interest. The non-human homolog can be any non-human animal such as, for example, a mouse, rat, goat, hamster, pig, chimpanzee, horse, sheep, monkey and guinea pig. In a particular embodiment, the non-human mammal is a mouse, rat or goat. In a specific embodiment, the non-human mammal is a mouse.

In exemplary embodiments of the present methods, the chimeric transmembrane protein of interest includes one or more extracellular loop domains from a human transmembrane protein of interest and an amino-terminal domain and/or carboxy-terminal domain from a non-human homolog of the transmembrane protein. In one embodiment, the chimeric transmembrane protein of interest includes one or more extracellular loop domains and a carboxy-terminal domain from a human transmembrane protein and an amino-terminal domain from a non-human homolog of the transmembrane protein. In another embodiment, the chimeric transmembrane protein of interest includes one or more extracellular loop domains and an amino-terminal domain from a human transmembrane protein and a caboxy-terminal domain from a non-human homolog of the transmembrane protein. In another embodiment, the chimeric transmembrane protein of interest includes an amino-terminal domain and carboxy-terminal domain from a human transmembrane protein and one or more extracellular loop domains from a non-human homolog of the transmembrane protein. In one embodiment, the chimeric transmembrane protein of interest includes an amino-terminal domain from a human transmembrane protein and one or more extracellular loop domains and a carboxyl-terminal domain from a non-human homolog of the transmembrane protein. In yet another embodiment, the chimeric transmembrane protein of interest includes one or more extracellular loop domains from a non-human homolog and an amino-terminal domain from the non-human homolog of the transmembrane protein.

In other embodiments of the methods, a non-human animal or a genetically-engineered non-human animal such as, for example, a mouse or a rat, is immunized with a full-length human transmembrane protein of interest, a nucleic acid sequence encoding the same or a combination thereof. Splenocytes are isolated from the immunized non-human animal and are incubated with labeled antibodies to a B cell marker (e.g., fluorochrome-labeled anti-IgG antibody) to identify a population of B cells. The cells are also incubated with biotinylated lipid bilayer-membrane scaffold protein complex that encompasses a non-human homolog of the transmembrane protein to permit binding between the non-human transmembrane protein of interest (antigen) presented by the complex and cross-reactive antibody produced by the cells. Cells can then be washed. PE fluorescence and signals from bound B cells (e.g., fluorochrome-labeled anti-IgG signals) can be detected by FACS to identify and collect a homogeneous population of antibody-producing B cells that express cross-reactive antibody that binds an epitope present on the non-human transmembrane protein of interest and the human transmembrane protein of interest.

In embodiments of the present methods that include the use of a non-human homolog of the transmembrane protein of interest or a portion thereof, the non-human homolog can be any non-human organism. Certain examples of non-human organisms include, but are not limited to, non-human mammals, reptiles, fish, bacteria, insects, and viruses. In some embodiments, the non-human protein can be from a mouse, rat, goat, hamster, pig, chimpanzee, horse, sheep, monkey and guinea pig. In particular embodiments, the non-human protein homolog is from a mouse, rat or goat. In a specific embodiment, the non-human homolog is a mouse homolog of the transmembrane protein of interest.

In some embodiments of the methods, a non-human animal or a genetically-engineered non-human animal such as, for example, a mouse or a rat, is immunized with a full-length human transmembrane protein of interest, a nucleic acid sequence encoding the same or a combination thereof, splenocytes are isolated from the immunized non-human animal (e.g., rat or mouse) and are incubated a portion of the full-length human transmembrane of interest (peptide blocking agent) to permit binding between the peptide blocking agent and antibody produced by the cells that specifically bind to an epitope located on the blocking agent. The cells are also incubated with labeled antibodies to a B cell marker (e.g., fluorochrome-labeled anti-IgG antibody) to identify a population of B cells and with biotinylated lipid bilayer-membrane scaffold protein complex that encompasses the full-length transmembrane protein to permit binding between the full-length transmembrane protein of interest (antigen) presented by the complex and antibody produced by the remaining unbound cells in the population. Subsequently, the cells are incubated with PE-streptavidin to enable streptavidin binding to each of the biotin (Bir-A) labeled membrane scaffold proteins in the lipid-bilayer-membrane scaffold protein complex. Cells can then be washed to remove all cells bound to the peptide blocking agent, unbound and excess PE-streptavidin and labeled antibodies to a B cell marker from the sort. PE fluorescence and signals from bound B cells (e.g., fluorochrome-labeled anti-IgG signals) can be detected by FACS to identify and collect a homogeneous population of antibody-producing B cells that express antibody that binds an epitope on the full-length human transmembrane protein of interest that is not present on the portion corresponding to the peptide blocking agent.

In embodiments of the methods that include the use of a blocking agent, the blocking agent can be any molecule such as, for example, a peptide, polypeptide, chemical compound. In such embodiments, the blocking agent can be a polypeptide or peptide that corresponds to a portion of a transmembrane protein of interest, a polypeptide or polypeptide that corresponds to a portion of an MSP protein, or a detectable marker such as a His-tag or Flag-tag. In some embodiments, the blocking agent includes a detectable label. In other embodiments, the blocking agent does not include a detectable label. In one embodiment, the blocking agent is a peptide or polypeptide portion of the transmembrane protein of interest, which can be incubated with a population of antibody-producing cells to permit binding between the blocking agent and antibody produced by the antibody-producing cells that specifically bind an epitope located on the blocking agent. In one embodiment, blocking agent is a truncated transmembrane protein of interest. In a particular embodiment, the blocking agent is a polypeptide that corresponds to one or more extracellular loop domains, an amino-terminal and carboxy-terminal portion of the full-length transmembrane protein of interest. In a particular embodiment, the blocking agent can be a polypeptide comprising the amino-terminal portion of the full-length transmembrane protein of interest. In another embodiment, the blocking agent can be a polypeptide comprising the carboxy-terminal portion of the full-length transmembrane protein of interest. In one embodiment, the blocking agent can be a polypeptide comprising an extracellular loop domain of the full-length transmembrane protein of interest. In some embodiments, the blocking agent includes an extracellular domain of a transmembrane protein of interest such as an N-terminal extracellular domain, a C-terminal extracellular domain, and/or an extracellular loop domain between one or more membrane spanning domains of the full-length transmembrane protein of interest. In another embodiment, the blocking agent is a peptide or polypeptide portion of an MSP protein, which can be incubated with a population of antibody-producing cells to permit binding between the blocking agent and antibody produced by the antibody-producing cells that specifically bind an epitope located on the blocking agent. In yet another embodiment, the blocking agent is a peptide or polypeptide detectable marker located on an MSP or transmembrane protein of interest, which can be incubated with a population of antibody-producing cells to permit binding between the blocking agent and antibody produced by the antibody-producing cells that specifically bind an epitope located on the blocking agent.

In other embodiments of the methods, a non-human animal or a genetically-engineered non-human animal such as, for example, a mouse or a rat, is immunized with a portion of a full-length human transmembrane protein of interest, a nucleic acid sequence encoding the same or a combination thereof (immunogen).

In some embodiments, splenocytes are isolated from the immunized non-human animal (e.g., rat or mouse) and incubated with labeled antibodies to a B cell marker (e.g., fluorochrome-labeled anti-IgG antibody) to identify a population of B cells. The cells are also incubated with biotinylated lipid bilayer-membrane scaffold protein complex that encompasses the full-length human transmembrane protein of interest (antigen) presented by the complex and antibody produced by the cells. Cells can then be washed. PE fluorescence and signals from bound B cells (e.g., fluorochrome-labeled anti-IgG signals) can be detected by FACS to identify and collect a homogeneous population of antibody-producing B cells that express antibody that binds an epitope located on a portion of the full-length human transmembrane protein of interest antigen that also corresponds to an amino-acid sequence or domain present on or encoded by the immunogen.

In other embodiments of the methods, a non-human animal or a genetically-engineered non-human animal such as, for example, a mouse or a rat, is immunized with a portion of a full-length human transmembrane protein of interest (immunogen), a nucleic acid sequence encoding the same or a combination thereof, splenocytes are isolated from the immunized non-human animal (e.g., rat or mouse) and are incubated with labeled antibodies to a B cell marker (e.g., fluorochrome-labeled anti-IgG antibody) to identify a population of B cells. The cells are also incubated with biotinylated lipid bilayer-membrane scaffold protein complex that encompasses the portion of the human transmembrane protein used as the immunogen to permit binding between an epitope on the portion of the human transmembrane protein of interest (antigen) presented by the complex and antibody produced by the cells. Subsequently, the cells are incubated with PE-streptavidin to enable streptavidin binding to each of the biotin (Bir-A) labeled membrane scaffold proteins in the lipid-bilayer-membrane scaffold protein complex Cells can then be washed. PE fluorescence and signals from bound B cells (e.g., fluorochrome-labeled anti-IgG signals) can be detected by FACS to identify and collect a homogeneous population of antibody-producing B cells that express antibody that binds an epitope on the antigen presented by the complex.

In embodiments of the instant methods, that include the use of a portion of the transmembrane protein of interest, the portion of the transmembrane protein is a peptide or polypeptide does not include the full-length transmembrane protein of interest. In one embodiment, the portion of a transmembrane protein of interest can be a modified transmembrane protein that does not include one or more extracellular loop domains, an amino-terminal and/or carboxy-terminal portion of the full-length transmembrane protein of interest. In a particular embodiment, modified transmembrane protein of interest can be a truncated transmembrane protein. In some embodiments, the portion of the transmembrane protein of interest includes a detectable label. In other embodiments, the portion of the transmembrane protein of interest does not include a detectable label. In certain embodiments, the truncated transmembrane protein of interest includes at least an entire transmembrane portion of the transmembrane protein of interest. In certain embodiments, the truncated transmembrane protein does not include the amino-terminal portion of the full-length transmembrane protein of interest. In another embodiment, the truncated transmembrane protein does not include the carboxy-terminal portion of the full-length transmembrane protein of interest. In some embodiments, the truncated protein includes an extracellular domain of a transmembrane protein of interest such as an N-terminal extracellular domain, a C-terminal extracellular domain, and/or an extracellular loop domain between one or more membrane spanning domains of the transmembrane protein of interest. In one embodiment, the truncated transmembrane protein does not include an extracellular loop domain of the full-length transmembrane protein of interest.

In another aspect of the methods, a genetically-engineered animal, which does not express the transmembrane protein of interest from an endogenous gene, is immunized with a non-human transmembrane protein of interest or a portion thereof, a nucleic acid sequence encoding the same or a combination thereof.

The non-human transmembrane protein of interest and the genetically-engineered animal can be from the same or different animal. The non-human transmembrane protein of interest can be from any non-human organism. Non-limiting examples of non-human organisms include, but are not limited to, non-human mammals, reptiles, fish, bacteria, insects, and viruses. In some embodiments, the non-human transmembrane protein is from an animal such as, for example, a mouse, rat, goat, hamster, pig, chimpanzee, horse, sheep, monkey and guinea pig. In a particular embodiment, the non-human is a mammal. In other embodiments, the non-human transmembrane protein is from a mouse, rat or goat. In a specific embodiment, the non-human mammal is a mouse.

In particular embodiments of the methods, a genetically-engineered animal is a non-human animal such as, for example, a mouse or a rat, that is immunized with a full-length non-human transmembrane protein of interest, a nucleic acid sequence encoding the same or a combination thereof (immunogen). Splenocytes are isolated from the immunized genetically-engineered animal (e.g., rat or mouse) and are incubated with labeled antibodies to a B cell marker (e.g., fluorochrome-labeled anti-IgG antibody) to identify a population of B cells. The cells are also incubated with biotinylated lipid bilayer-membrane scaffold protein complex that encompasses the full-length non-human transmembrane protein to permit binding between the transmembrane protein of interest (antigen) presented by the complex and antibody produced by the cells. Subsequently, the cells are incubated with PE-streptavidin to enable streptavidin binding to each of the biotin-labeled (e.g., Bir-A) membrane scaffold proteins in the lipid-bilayer-membrane scaffold protein complex. Cells can then be washed. PE fluorescence and signals from bound B cells (e.g., fluorochrome-labeled anti-IgG signals) can be detected by FACS to identify and collect a homogeneous population of antibody-producing B cells that express antibody that binds an epitope on the full-length non-human transmembrane protein of interest.

In other embodiments of the methods, a genetically-engineered non-human animal such as, for example, a mouse or a rat, is immunized with a full-length non-human transmembrane protein of interest, a nucleic acid sequence encoding the same or a combination thereof (immunogen), and splenocytes are isolated from the immunized non-human animal (e.g., rat or mouse) and are incubated with labeled antibodies to a B cell marker (e.g., fluorochrome-labeled anti-IgG antibody) to identify a population of B cells. The cells are also incubated with biotinylated lipid bilayer-membrane scaffold protein complex that encompasses a full-length human transmembrane protein of interest to permit binding between the human transmembrane protein of interest (antigen) presented by the complex and antibody produced by the cells. Subsequently, the cells are incubated with PE-streptavidin to enable streptavidin binding to each of the biotin-labeled (e.g., Bir-A) membrane scaffold proteins in the lipid-bilayer-membrane scaffold protein complex. Cells can then be washed. PE fluorescence and signals from bound B cells (e.g., fluorochrome-labeled anti-IgG signals) can be detected by FACS to identify and collect a homogeneous population of antibody-producing B cells that express cross-reactive antibody that binds an epitope on the full-length non-human transmembrane protein of interest and the non-human transmembrane protein of interest.

In some embodiments of the methods, a genetically-engineered non-human animal such as, for example, a mouse or a rat, is immunized with a full-length non-human transmembrane protein of interest, a nucleic acid sequence encoding the same or a combination thereof (immunogen), and splenocytes are isolated from the immunized non-human animal (e.g., rat or mouse) and are incubated with labeled antibodies to a B cell marker (e.g., fluorochrome-labeled anti-IgG antibody) to identify a population of B cells. The cells are also incubated with biotinylated lipid bilayer-membrane scaffold protein complex that encompasses a portion of the full-length non-human transmembrane protein, such as a truncated transmembrane protein, to permit binding between an epitope on the portion of the transmembrane protein of interest (antigen) presented by the complex and antibody produced by the cells. Subsequently, the cells are incubated with PE-streptavidin to enable streptavidin binding to each of the biotin (Bir-A) labeled membrane scaffold proteins in the lipid-bilayer-membrane scaffold protein complex Cells can then be washed. PE fluorescence and signals from bound B cells (e.g., fluorochrome-labeled anti-IgG signals) can be detected by FACS to identify and collect a homogeneous population of antibody-producing B cells that express antibody that binds an epitope on the antigen presented by the complex.

In embodiments of the methods that include a lipid-bilayer-membrane scaffold protein complex comprising a portion of the transmembrane protein of interest, the transmembrane protein presented by the complex does not include the full-length transmembrane protein of interest. In one embodiment, the transmembrane protein of interest is a truncated transmembrane protein that does not include, one or more extracellular loop domains, an amino-terminal and/or carboxy-terminal portion of the full-length transmembrane protein of interest. In certain embodiments, the truncated transmembrane protein of interest includes at least an entire transmembrane portion of the transmembrane protein of interest. In some embodiments, the truncated protein includes an extracellular domain of a transmembrane protein of interest such as an N-terminal extracellular domain, a C-terminal extracellular domain, and/or an extracellular loop domain between one or more membrane spanning domains of the transmembrane protein of interest. In a particular embodiment, the truncated transmembrane protein does not include the amino-terminal portion of the full-length transmembrane protein of interest. In another embodiment, the truncated transmembrane protein does not include the carboxy-terminal portion of the full-length transmembrane protein of interest. In one embodiment, the truncated transmembrane protein does not include an extracellular loop domain of the full-length transmembrane protein of interest.

In certain embodiments of the methods, a genetically-engineered non-human animal such as, for example, a mouse or a rat, is immunized with a full-length non-human transmembrane protein of interest, a nucleic acid sequence encoding the same or a combination thereof, splenocytes are isolated from the immunized animal and are incubated with labeled antibodies to a B cell marker (e.g., fluorochrome-labeled anti-IgG antibody) to identify a population of B cells. The cells are also incubated with biotinylated lipid bilayer-membrane scaffold protein complex that encompasses a chimeric transmembrane protein that includes a portion of the non-human homolog of the transmembrane protein of interest and a portion of the human transmembrane protein of interest to permit binding between a non-human portion of the chimeric transmembrane protein of interest (antigen) presented by the complex and antibody produced by the cells. Cells can then be washed. PE fluorescence and signals from bound B cells (e.g., fluorochrome-labeled anti-IgG signals) can be detected by FACS to identify and collect a homogeneous population of antibody-producing B cells that express antibody that binds an epitope on a non-human portion of the chimeric transmembrane protein of interest.

In embodiments of the methods that include the use of a chimeric transmembrane protein of interest, the chimeric protein can include portions of a transmembrane protein of interest from two different species as described herein. For example, the chimeric transmembrane protein can include one or more portions of a human transmembrane protein operably linked to one or more portions of a non-human homolog of the transmembrane protein. In some instances, the chimeric transmembrane protein includes an extracellular domain of a transmembrane protein of interest such as an N-terminal extracellular domain, a C-terminal extracellular domain, and/or an extracellular loop domain between one or more membrane spanning domains of the transmembrane protein of interest. The non-human homolog can be any non-human animal such as, for example, a mouse, rat, goat, hamster, pig, chimpanzee, horse, sheep, monkey and guinea pig. In a particular embodiment, the non-human mammal is a mouse, rat or goat. In a specific embodiment, the non-human mammal is a mouse.

In exemplary embodiments of the present methods, the chimeric transmembrane protein of interest includes one or more extracellular loop domains from the human transmembrane protein and an amino-terminal domain and/or carboxy-terminal domain from a non-human homolog of the transmembrane protein. In one embodiment, the chimeric transmembrane protein of interest includes one or more extracellular loop domains and a carboxy-terminal domain from the human transmembrane protein and an amino-terminal domain from a non-human homolog of the transmembrane protein. In another embodiment, the chimeric transmembrane protein of interest includes one or more extracellular loop domains and an amino-terminal domain from the human transmembrane protein and a caboxy-terminal domain from a non-human homolog of the transmembrane protein. In another embodiment, the chimeric transmembrane protein of interest includes an amino-terminal domain and carboxy-terminal domain from a human transmembrane protein and one or more extracellular loop domains from a non-human homolog of the transmembrane protein. In one embodiment, the chimeric transmembrane protein of interest includes an amino-terminal domain from a human transmembrane protein and one or more extracellular loop domains and a carboxyl-terminal domain from a non-human homolog of the transmembrane protein. In yet another embodiment, the chimeric transmembrane protein of interest includes one or more extracellular loop domains from a non-human homolog and an amino-terminal domain from the non-human homolog of the transmembrane protein.

In other embodiments of the methods, the genetically-engineered non-human animal such as, for example, a mouse or a rat, is immunized with a portion of a full-length non-human transmembrane protein of interest, a nucleic acid sequence encoding the same or a combination thereof (immunogen).

In one such exemplary embodiment, splenocytes are isolated from the immunized genetically engineered animal and incubated with labeled antibodies to a B cell marker (e.g., fluorochrome-labeled anti-IgG antibody) to identify a population of B cells. The cells are also incubated with biotinylated lipid bilayer-membrane scaffold protein complex that encompasses the full-length non-human transmembrane protein to permit binding between the full-length transmembrane protein of interest (antigen) presented by the complex and antibody produced by the cells. Cells can then be washed. PE fluorescence and signals from bound B cells (e.g., fluorochrome-labeled anti-IgG signals) can be detected by FACS to identify and collect a homogeneous population of antibody-producing B cells that express antibody that binds an epitope located on a portion of the full-length non-human transmembrane protein of interest antigen that also corresponds to an amino-acid sequence or domain present on or encoded by the immunogen.

In other embodiments of the methods, a genetically-engineered non-human animal such as, for example, a mouse or a rat, is immunized with a portion of a full-length non-human transmembrane protein of interest (immunogen), a nucleic acid sequence encoding the same or a combination thereof, splenocytes are isolated from the immunized non-human animal (e.g., rat or mouse) and are incubated with labeled antibodies to a B cell marker (e.g., fluorochrome-labeled anti-IgG antibody) to identify a population of B cells. The cells are also incubated with biotinylated lipid bilayer-membrane scaffold protein complex that encompasses the portion of the non-human transmembrane protein used as the immunogen to permit binding between an epitope on the portion of the human transmembrane protein of interest (antigen) presented by the complex and antibody produced by the cells. Subsequently, the cells are incubated with PE-streptavidin to enable streptavidin binding to each of the biotin (Bir-A) labeled membrane scaffold proteins in the lipid-bilayer-membrane scaffold protein complex. Cells can then be washed. PE fluorescence and signals from bound B cells (e.g., fluorochrome-labeled anti-IgG signals) can be detected by FACS to identify and collect a homogeneous population of antibody-producing B cells that express antibody that binds an epitope on the antigen presented by the complex.

In another aspect of the methods, a genetically-engineered animal, which does not express the transmembrane protein of interest from an endogenous gene, is immunized with a chimeric transmembrane protein of interest, or a nucleic acid encoding the same.

In instances that include the use of a chimeric transmembrane protein of interest, the chimeric protein can include portions of a transmembrane protein of interest from two different species as described herein. For example, the chimeric transmembrane protein can include one or more portions of a human transmembrane protein operably linked to one or more portions of a non-human homolog of the transmembrane protein. In some instances, the chimeric transmembrane protein of interest includes an extracellular domain of a human transmembrane protein of interest such as an N-terminal extracellular domain, a C-terminal extracellular domain, and/or an extracellular loop domain operably linked to one or more membrane spanning domains of the transmembrane protein of interest. The non-human homolog can be any non-human animal such as, for example, a mouse, rat, goat, hamster, pig, chimpanzee, horse, sheep, monkey and guinea pig. In a particular embodiment, the non-human mammal is a mouse, rat or goat. In a specific embodiment, the non-human mammal is a mouse.

In exemplary embodiments of the present methods, the chimeric transmembrane protein of interest includes one or more extracellular loop domains from a human transmembrane protein of interest and an amino-terminal domain and/or carboxy-terminal domain from a non-human homolog of the transmembrane protein. In one embodiment, the chimeric transmembrane protein of interest includes one or more extracellular loop domains and a carboxy-terminal domain from a human transmembrane protein and an amino-terminal domain from a non-human homolog of the transmembrane protein. In another embodiment, the chimeric transmembrane protein of interest includes one or more extracellular loop domains and an amino-terminal domain from the human transmembrane protein and a caboxy-terminal domain from a non-human homolog of the transmembrane protein. In another embodiment, the chimeric transmembrane protein of interest includes an amino-terminal domain and carboxy-terminal domain from a human transmembrane protein and one or more extracellular loop domains from a non-human homolog of the transmembrane protein. In one embodiment, the chimeric transmembrane protein of interest includes an amino-terminal domain from a human transmembrane protein and one or more extracellular loop domains and a carboxyl-terminal domain from a non-human homolog of the transmembrane protein. In yet another embodiment, the chimeric transmembrane protein of interest includes one or more extracellular loop domains from a non-human homolog operatively linked to a transmembrane domain and an amino-terminal domain from the non-human homolog of the transmembrane protein.

In one particular embodiment of the methods, a genetically-engineered non-human animal such as, for example, a mouse or a rat, is immunized with a chimeric transmembrane protein that includes a portion of a human transmembrane protein and a portion of a non-human homolog of the transmembrane protein, a nucleic acid sequence encoding the same or a combination thereof, splenocytes are isolated from the immunized non-human animal (e.g., rat or mouse) and are incubated with labeled antibodies to a B cell marker (e.g., fluorochrome-labeled anti-IgG antibody) to identify a population of B cells. The cells are also incubated with biotinylated lipid bilayer-membrane scaffold protein complex that encompasses the full-length human transmembrane protein of interest (antigen) to permit binding between the human antigen presented by the complex and antibody produced by the cells specific to a human portion of the chimeric transmembrane protein of interest. Cells can then be washed. PE fluorescence and signals from bound B cells (e.g., fluorochrome-labeled anti-IgG signals) can be detected by FACS to identify and collect a homogeneous population of antibody-producing B cells that express antibody that binds an epitope on a human portion of the chimeric transmembrane protein of interest.

In another embodiment of the methods, a genetically-engineered non-human animal such as, for example, a mouse or a rat, is immunized with a chimeric transmembrane protein that includes a portion of a human transmembrane protein and a portion of a non-human homolog of the transmembrane protein of interest, a nucleic acid sequence encoding the same or a combination thereof, splenocytes are isolated from the immunized non-human animal (e.g., rat or mouse) and are incubated with labeled antibodies to a B cell marker (e.g., fluorochrome-labeled anti-IgG antibody) to identify a population of B cells. The cells are also incubated with biotinylated lipid bilayer-membrane scaffold protein complex that encompasses a portion of the full-length human transmembrane protein of interest (antigen) to permit binding between the human antigen presented by the complex and antibody produced by the cells specific to a human portion of the chimeric transmembrane protein of interest. Cells can then be washed. PE fluorescence and signals from bound B cells (e.g., fluorochrome-labeled anti-IgG signals) can be detected by FACS to identify and collect a homogeneous population of antibody-producing B cells that express antibody that binds an epitope on a human portion of the chimeric transmembrane protein of interest.

In yet another embodiment, the methods, a genetically-engineered non-human animal such as, for example, a mouse or a rat, is immunized with a chimeric transmembrane protein that includes a portion of a human transmembrane protein of interest and a portion of a non-human homolog of the transmembrane protein of interest, a nucleic acid sequence encoding the same or a combination thereof, splenocytes are isolated from the immunized non-human animal (e.g., rat or mouse) and are incubated with labeled antibodies to a B cell marker (e.g., fluorochrome-labeled anti-IgG antibody) to identify a population of B cells. The cells are also incubated with biotinylated lipid bilayer-membrane scaffold protein complex that encompasses the full-length non-human transmembrane protein of interest (antigen) to permit binding between the non-human antigen presented by the complex and antibody produced by the cells specific to a non-human portion of the chimeric transmembrane protein of interest. Cells can then be washed. PE fluorescence and signals from bound B cells (e.g., fluorochrome-labeled anti-IgG signals) can be detected by FACS to identify and collect a homogeneous population of antibody-producing B cells that express antibody that binds an epitope on a non-human portion of the chimeric transmembrane protein of interest.

In another embodiment of the methods, a genetically-engineered non-human animal such as, for example, a mouse or a rat, is immunized with a chimeric transmembrane protein that includes a portion of a human transmembrane protein of interest and a portion of a non-human homolog of the transmembrane protein of interest, a nucleic acid sequence encoding the same or a combination thereof, splenocytes are isolated from the immunized non-human animal (e.g., rat or mouse) and are incubated with labeled antibodies to a B cell marker (e.g., fluorochrome-labeled anti-IgG antibody) to identify a population of B cells. The cells are also incubated with biotinylated lipid bilayer-membrane scaffold protein complex that encompasses a portion of the full-length non-human transmembrane protein of interest (antigen) to permit binding between the non-human antigen presented by the complex and antibody produced by the cells specific to a non-human portion of the chimeric transmembrane protein of interest. Cells can then be washed. PE fluorescence and signals from bound B cells (e.g., fluorochrome-labeled anti-IgG signals) can be detected by FACS to identify and collect a homogeneous population of antibody-producing B cells that express antibody that binds an epitope on a non-human human portion of the chimeric transmembrane protein of interest.

In another aspect of the methods, a non-human animal or a genetically-engineered non-human animal such as, for example, a mouse or a rat, is immunized with a lipid bilayer-membrane scaffold protein complex that encompasses a full-length transmembrane protein of interest or a portion thereof.

In some embodiments of the methods, a non-human animal or a genetically-engineered non-human animal such as, for example, a mouse or a rat, is immunized with a lipid bilayer-membrane scaffold protein complex that encompasses a full-length human transmembrane protein of interest. Splenocytes are isolated from the immunized non-human animal (e.g., rat or mouse) and are incubated with a or a plurality of blocking agents that correspond to each of the MSP proteins included in the complex and each detectable marker included in the complex or affixed to the transmembrane protein of interest, such as a His-tag or Flag-tag, to permit binding between the blocking agents and antibody produced by the cells that specifically bind to an epitope located on the blocking agent. The cells are also incubated with labeled antibodies to a B cell marker (e.g., fluorochrome-labeled anti-IgG antibody) to identify a population of B cells. Cells are then incubated with biotinylated lipid bilayer-membrane scaffold protein complex that encompasses the full-length human transmembrane protein to permit binding between the full-length transmembrane protein of interest (antigen) presented by the complex and antibody produced by the remaining unbound cells in the population. Subsequently, the cells are incubated with PE-streptavidin to enable streptavidin binding to each of the biotin (Bir-A) labeled membrane scaffold proteins in the lipid-bilayer-membrane scaffold protein complex. Cells can then be washed to remove all cells bound to the blocking agent(s), as well as unbound and excess PE-streptavidin and labeled antibodies to a B cell marker from the sort. PE fluorescence and signals from bound B cells (e.g., fluorochrome-labeled anti-IgG signals) can be detected by FACS to identify and collect a homogeneous population of antibody-producing B cells that express antibody that binds an epitope on the full-length human transmembrane protein of interest.

In one embodiment of the methods, a non-human animal or a genetically-engineered non-human animal such as, for example, a mouse or a rat, is immunized with a lipid bilayer-membrane scaffold protein complex that encompasses a full-length human transmembrane protein of interest. Splenocytes are isolated from the immunized non-human animal (e.g., rat or mouse) and are incubated with a or a plurality of blocking agents that correspond to each of the MSP proteins included in the complex and each detectable marker included in the complex or affixed to the transmembrane protein of interest, such as a His-tag or Flag-tag, to permit binding between the blocking agents and antibody produced by the cells that specifically bind to an epitope located on the blocking agent. The cells are also incubated with labeled antibodies to a B cell marker (e.g., fluorochrome-labeled anti-IgG antibody) to identify a population of B cells. Cells are then incubated with biotinylated lipid bilayer-membrane scaffold protein complex that encompasses a portion of the human transmembrane protein to permit binding between the portion of the transmembrane protein of interest (antigen) presented by the complex and antibody produced by the remaining unbound cells in the population. Subsequently, the cells are incubated with PE-streptavidin to enable streptavidin binding to each of the biotin (Bir-A) labeled membrane scaffold proteins in the lipid-bilayer-membrane scaffold protein complex. Cells can then be washed to remove all cells bound to the blocking agent(s), as well as unbound and excess PE-streptavidin and labeled antibodies to a B cell marker from the sort. PE fluorescence and signals from bound B cells (e.g., fluorochrome-labeled anti-IgG signals) can be detected by FACS to identify and collect a homogeneous population of antibody-producing B cells that express antibody that binds an epitope on the portion of the full-length human transmembrane protein of interest presented by the complex.

In other embodiments of the methods, a genetically-engineered non-human animal such as, for example, a mouse or a rat, that does not express the transmembrane protein of interest from an endogenous gene, is immunized with a lipid bilayer-membrane scaffold protein complex that encompasses a full-length non-human transmembrane protein of interest. Splenocytes are isolated from the immunized non-human animal (e.g., rat or mouse) and are incubated with a or a plurality of blocking agents that correspond to each of the MSP proteins included in the complex and each detectable marker included in the complex or affixed to the transmembrane protein of interest, such as a His-tag or FLAG-tag, to permit binding between the blocking agents and antibody produced by the cells that specifically bind to an epitope located on the blocking agent. The cells are also incubated with labeled antibodies to a B cell marker (e.g., fluorochrome-labeled anti-IgG antibody) to identify a population of B cells. Cells are then incubated with biotinylated lipid bilayer-membrane scaffold protein complex that encompasses the full-length non-human transmembrane protein to permit binding between the full-length transmembrane protein of interest (antigen) presented by the complex and antibody produced by the remaining unbound cells in the population. Subsequently, the cells are incubated with PE-streptavidin to enable streptavidin binding to each of the biotin (Bir-A) labeled membrane scaffold proteins in the lipid-bilayer-membrane scaffold protein complex. Cells can then be washed to remove all cells bound to the blocking agent(s), as well as unbound and excess PE-streptavidin and labeled antibodies to a B cell marker from the sort. PE fluorescence and signals from bound B cells (e.g., fluorochrome-labeled anti-IgG signals) can be detected by FACS to identify and collect a homogeneous population of antibody-producing B cells that express antibody that binds an epitope on the full-length non-human transmembrane protein of interest.

In some embodiments of the methods, a genetically-engineered non-human animal such as, for example, a mouse or a rat, that does not express the transmembrane protein of interest from an endogenous gene, is immunized with a lipid bilayer-membrane scaffold protein complex that encompasses a encompasses a portion of a full-length non-human transmembrane protein of interest. Splenocytes are isolated from the immunized animal and are incubated with a or a plurality of blocking agents that correspond to each of the MSP proteins included in the complex and each detectable marker included in the complex or affixed to the portion of the non-human transmembrane protein of interest, such as a His-tag or FLAG-tag, to permit binding between the blocking agents and antibody produced by the cells that specifically bind to an epitope located on the blocking agent. The cells are also incubated with labeled antibodies to a B cell marker (e.g., fluorochrome-labeled anti-IgG antibody) to identify a population of B cells. Cells are then incubated with biotinylated lipid bilayer-membrane scaffold protein complex that encompasses a portion of the full-length non-human transmembrane protein or a full-length non-human transmembrane protein of interest (antigen) to permit binding between the transmembrane protein of interest presented by the complex and antibody produced by the remaining unbound cells in the population. Subsequently, the cells are incubated with PE-streptavidin to enable streptavidin binding to each of the biotin (Bir-A) labeled membrane scaffold proteins in the lipid-bilayer-membrane scaffold protein complex. Cells can then be washed to remove all cells bound to the blocking agent(s), as well as unbound and excess PE-streptavidin and labeled antibodies to a B cell marker from the sort. PE fluorescence and signals from bound B cells (e.g., fluorochrome-labeled anti-IgG signals) can be detected by FACS to identify and collect a homogeneous population of antibody-producing B cells that express antibody that binds an epitope on a portion of the full-length non-human transmembrane protein of interest.

In embodiments of the methods that include the use of a blocking agent, the blocking agent can comprise any molecule such as, for example, a peptide, polypeptide, chemical compound. In such embodiments, the blocking agent can be a polypeptide or peptide that corresponds to a portion of a transmembrane protein of interest, a polypeptide or polypeptide that corresponds to a portion of an MSP protein, or a detectable marker such as a His-tag or FLAG-tag. In some embodiments, the blocking agent includes a detectable label. In other embodiments, blocking agent does not include a detectable label. In one embodiment, the blocking agent is a peptide or polypeptide portion of the transmembrane protein of interest, which can be incubated with a population of antibody-producing cells to permit binding between the blocking agent and antibody produced by the antibody-producing cells that specifically bind an epitope located on the blocking agent. In one embodiment, blocking agent is a truncated transmembrane protein of interest. In a particular embodiment, the blocking agent is a polypeptide that corresponds to one or more extracellular loop domains, an amino-terminal and carboxy-terminal portion of the full-length transmembrane protein of interest. In a particular embodiment, the blocking agent can be a polypeptide comprising the amino-terminal portion of the full-length transmembrane protein of interest. In another embodiment, the blocking agent can be a polypeptide comprising the carboxy-terminal portion of the full-length transmembrane protein of interest. In one embodiment, the blocking agent can be a polypeptide comprising an extracellular loop domain of the full-length transmembrane protein of interest. In some embodiments, the blocking agent is a truncated protein that includes an extracellular domain of a transmembrane protein of interest such as an N-terminal extracellular domain, a C-terminal extracellular domain, and/or an extracellular loop domain between one or more membrane spanning domains of the transmembrane protein of interest. In another embodiment, the blocking agent is a peptide or polypeptide portion of an MSP protein, which can be incubated with a population of antibody-producing cells to permit binding between the blocking agent and antibody produced by the antibody-producing cells that specifically bind an epitope located on the blocking agent. In yet another embodiment, the blocking agent is a peptide or polypeptide detectable marker located on an MSP or transmembrane protein of interest, which can be incubated with a population of anti-body-producing cells to permit binding between the blocking agent and antibody produced by the antibody-producing cells that specifically bind an epitope located on the blocking agent.

The disclosed methods include detecting, sorting and collecting antibody-producing cells that are bound to an antigen presented by a lipid bilayer-membrane scaffold protein complex encompassing a transmembrane protein of interest. Detecting, sorting and collecting may be combined or carried out as distinct steps. The detecting, sorting and/or collecting may include identifying cells bound by the transmembrane protein of interest presented by a complex through detection of one or more a detectable labels on the complex. The bound cells can then be separated from unbound cells (i.e., sorted) and selected for further use.

In some embodiments, interaction between antibody-producing cells and the lipid bilayer-membrane scaffold protein complex presenting a transmembrane protein of interest is detected a by a conformational change of the transmembrane protein of interest, activation or deactivation of the transmembrane protein of interest in a cell, or by the use of detectable labels (e.g., fluorescent molecules, FLAG tag, His-tag) to identify and capture cells bound to a lipid bilayer-membrane scaffold protein complex containing a transmembrane protein of interest. Detection can be carried out by immuno-staining with an antibody specific for the label or direct staining with a reagent that binds to the label. Numerous detection kits and techniques are well-known in the art.

In certain embodiments of the methods, cells are washed with buffer for a period of time from about 5 minutes to about 60 minutes to remove unbound antigen; multiple washes that total from 10 to 120 minutes may be used, e.g., 3 washes of 10 minutes or one 30-minute wash; 2-4 washes of 10-15 minutes each. In one embodiment, washing the cells for a period of time comprising one (1) wash about 10 minutes, or about 15 minutes or about 20 minutes, or about 25 minutes, or about 30 minutes, or about 35 minutes, or about 40 minutes, or about 45 minutes, or about 50 minutes, or about 55 minutes, or about 60 minutes total, may be used. In some embodiments, washing the cells for a period of time comprising two (2) washes each about 5 minutes, or about 10 minutes, or about 15 minutes or about 20 minutes, or about 25 minutes, or about 30 minutes per wash, may be used. Additional washing intervals are contemplated, essentially equivalent to those described herein.

In some embodiments, detecting, sorting and collecting can be carried out using fluorescence-activated cell sorting (FACS) to detect, sort and select single antibody-producing cells that express a transmembrane protein-specific antibody. Protocols for single cell isolation by flow cytometry are well-known (Huang, J. et al, 2013, supra). For example, cells that bind antigen presented by a labeled (e.g., fluorescent label) lipid bilayer-membrane scaffold protein complex (or fluorescently-labeled streptavidin/biotinylated antigen) can be detected and identified as cells that express antibodies that specifically bind the antigen (i.e., transmembrane protein of interest), and then collected in individual wells on 96-well, or 384-well plates.

Once collected, single antibody-producing cells may be propagated by common cell culture techniques for subsequent DNA preparation. Alternatively, antibody genes may be amplified from single antibody-producing cells directly and subsequently cloned into DNA vectors.

Single antibody-producing cells may be sorted and collected by alternative methods known in the art, including but not limited to manual single cell picking, limited dilution and B cell panning of adsorbed antigen, which are all well-known in the art. See, for example, Rolink et al., J Exp Med (1996)183:187-194; Lightwood, D. et al, J. Immunol. Methods (2006) 316(1-2):133-43.

Generating Antibodies from Nucleic Acids Obtained from Antibody Producing Cells that Express an Antibody to a Transmembrane Protein of Interest.

A nucleic acid encoding an antibody or a fragment thereof can be isolated from the antibody-producing cells generated and obtained using the methods described herein.

In some embodiments, the nucleic acid encodes a fragment of an antibody, such as a variable domain, constant domain or combination thereof. In certain embodiments, the nucleic acid isolated from an antibody-producing cell encodes a variable domain of an antibody. In some embodiments, the nucleic acid encodes an antibody heavy chain or a fragment thereof. In other embodiments, the nucleic acid encodes an antibody light chain or a fragment thereof.

In certain instances, the nucleic acid isolated from antibody-producing cell is expressed in host cells. For example, a nucleic acid isolated from antibody-producing cells can be expressed (e.g., cloned and reproduced recombinantly) in host cells, such as mammalian cells, bacterial cells or insect cells. In some embodiments, the host cells are cultured under conditions that express the nucleic acid, and the antibody or portion thereof can then be produced and isolated for further use. Methods for producing antibodies from isolated nucleic acids are well known in the art and any such method can be used in conjunction with the present disclosure.

In some embodiments, host cells comprising one or more of the above nucleic acids are cultured under conditions that express a full-length antibody, and the antibody can then be produced and isolated for further use. In certain embodiments, the host cell comprises a nucleic acid that encodes a variable domain of an antibody, and the cell is cultured under conditions that express the variable domain. In other embodiments, the host cell comprises a nucleic acid that encodes a variable heavy chain ($V_H$) domain of an antibody, and the cell is cultured under conditions that express the $V_H$ domain. In another embodiment, the host cell comprises a nucleic acid that encodes a variable light chain ($V_L$) domain of an antibody, and the cell is cultured under conditions that express the $V_L$ domain. In specific embodiments, the host cell comprises a nucleic acid that encodes a $V_H$ domain of an antibody and nucleic acid that encodes a $V_L$ domain of an antibody, and the cell is cultured under conditions that express the $V_H$ domain and the $V_L$ domain.

In some embodiments, DNA can be isolated from the host to recombinantly produce the antibodies. Generally, genes or nucleic acids encoding immunoglobulin variable heavy and variable light chains (i.e., $V_H$, $V_L$, Vκ and Vλ) can be recovered using RT-PCR protocols with nucleic acids isolated from antibody-producing cells. These RT-PCR protocols are well known and conventional techniques, as described for example, by Wang et al., *J. Immunol. Methods* (2000) 244:217-225 and described herein.

Once recovered, antibody-encoding genes or nucleic acids can be cloned into IgG heavy- and light-chain expression vectors and expressed via transfection of host cells. For example, antibody-encoding genes or nucleic acids can be inserted into a replicable vector for further cloning (amplification of the DNA) or for expression (stably or transiently) in cells. Many vectors, particularly expression vectors, are available or can be engineered to comprise appropriate regulatory elements required to modulate expression of an antibody encoding gene or nucleic acid.

An expression vector in the context of the present disclosure can be any suitable vector, including chromosomal, non-chromosomal, and synthetic nucleic acid vectors (a nucleic acid sequence comprising a suitable set of expression control elements) as described herein. Examples of such vectors include derivatives of SV40, bacterial plasmids, phage DNA, baculovirus, yeast plasmids, vectors derived from combinations of plasmids and phage DNA, and viral nucleic acid (RNA or DNA) vectors.

In some embodiments, a nucleic acid molecule is included in a naked DNA or RNA vector, including, for example, a linear expression element (as described in, for instance, Sykes and Johnston, *Nat Biotech* (1997) 12:355-59), a compacted nucleic acid vector (as described in for instance U.S. Pat. No. 6,077,835), or a plasmid vector such as pBR322 or pUC 19/18. Such nucleic acid vectors and the usage thereof are well known in the art. See, for example, U.S. Pat. Nos. 5,589,466 and 5,973,972.

In certain embodiments, the expression vector can be a vector suitable for expression in a yeast system. Any vector suitable for expression in a yeast system may be employed. Suitable vectors include, for example, vectors comprising constitutive or inducible promoters such as yeast alpha factor, alcohol oxidase and PGH. See, F. Ausubel et al., ed. Current Protocols in Molecular Biology, Greene Publishing and Wiley InterScience New York (1987); and Grant et al., *Methods in Enzymol* 153, 516-544 (1987).

In certain embodiments, the vector comprises a nucleic acid molecule (or gene) encoding a heavy chain of the antibody and a nucleic acid molecule (or gene) encoding a light chain of the antibody, wherein the antibody is produced by an antibody-producing cell that has been obtained by a method of the present disclosure. Generally, the vector utilized includes an expression vector comprising the nucleic acid molecules (or genes) described wherein the nucleic acid molecule (or gene) is operably linked to an expression control sequence suitable for expression in the host cell.

The choice of vector depends in part on the host cell to be used. Host cells include, but are not limited to, cells of either prokaryotic or eukaryotic (generally mammalian) origin.

It will be appreciated that the full-length antibody nucleic acid sequence or gene may be subsequently cloned into an appropriate vector or vectors. Alternatively, the Fab region of an isolated antibody may be cloned into a vector or vectors in line with constant regions of any isotype. Therefore, any constant region may be utilized in the construction of isolated antibodies, including IgG1, IgG2, IgG3, IgG4, IgM, IgA, IgD, and IgE heavy chain constant regions, or chimeric heavy chain constant regions. Such constant regions can be obtained from any human or animal species depending on the intended use of the antibodies. Also, antibody variable regions or Fab region may be cloned in an appropriate vector(s) for the expression of the protein in other formats, such as ScFv, diabody, etc.

As such, the disclosure also provides a mammalian host cell encoding a nucleic acid molecule comprising a full-length antibody specific for a transmembrane protein of interest, wherein the antibody-encoding nucleic acid or gene was isolated from a antibody-producing cell obtained in accordance with the present methods. In one embodiment, the primary antibody-producing cell was a B-cell isolated from a heterogeneous population of cells obtained from an immunized mammal.

In some embodiments, the host cell is a bacterial or yeast cell. In some embodiments, the host cell is a mammalian cell. In other embodiments, the host cell can be, for example, a Chinese hamster ovarian cells (CHO) such as, CHO K1, DXB-11 CHO, Veggie-CHO cells; a COS (e.g., COS-7); a stem cell; retinal cells; a Vero cell; a CV1cell; a kidney cell such as, for example, a HEK293, a 293 EBNA, an MSR 293, an MDCK, aHaK, a BHK21 cell; a HeLa cell; a HepG2 cell; WI38; MRC 5; Colo25; HB 8065; HL-60; a Jurkat or Daudi cell; an A431 (epidermal) cell; a CV-1, U937, 3T3 or L-cell; a C127 cell, SP2/0, NS-0 or MMT cell, a tumor cell, and a cell line derived from any of the aforementioned cells. In a particular embodiment, the host cell is a CHO cell. In a specific embodiment, the host cell is a CHO K1 cell.

Antibody and antibodies as those terms are known in the art refer to antigen binding proteins of the immune system. The term "antibody" as referred to herein includes whole, full-length antibodies having an antigen-binding region, and any fragment thereof in which the "antigen-binding portion" or "antigen-binding region" is retained, or single chains, for example, single chain variable fragment (scFv), thereof. A "full-length antibody" is a glycoprotein comprising at least two heavy (H) chains and two light (L) chains inter-connected by disulfide bonds. Each heavy chain is comprised of a heavy chain variable region ($V_H$) and a heavy chain constant (CH) region. The heavy chain constant region is comprised of three domains, CH1 CH2 and CH3. Each light chain is comprised of a light chain variable region ($V_L$) and a light chain constant CL region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is comprised of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen.

As shown herein, the present disclosure can be used to obtain antibodies that bind to a transmembrane protein of interest. The antibodies obtained from antibody-producing cells as described herein can be characterized using known methods in the art. For example, the binding affinity, specific epitope recognized or functional ability of any of the antibodies generated herein can be determined.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule for its binding partner can generally be represented by the dissociation equilibrium constant (KD or $K_D$). There is an inverse relationship between $K_D$ (molar, M) value and binding affinity, therefore the smaller the $K_D$ value (M), the higher the binding affinity of the molecule to its binding epitope.

The terms "higher affinity" or "high affinity" refer to an antibody that generally binds antigen stronger and/or faster and/or remains bound longer. Generally, a high affinity antibody requires a lower concentration (M) of antigen to achieve a desired effect due to the strong binding interaction. Conversely, the terms "low affinity" and "lower affinity" are terms used to reflect weaker binding, such as a reduced ability to form an interaction between a molecule and its binding partner when compared to other binding molecules (e.g., antibodies). Low affinity binding molecules, therefore will have a larger $K_D$ value when compared to other binding molecules and/or will bind antigen slowly and tend to dissociate readily.

The term "kd" (sec −1 or 1/s) refers to the dissociation rate constant of a particular antibody-antigen interaction, or the dissociation rate constant of an antibody, Ig, antibody-binding fragment, or molecular interaction. This value is also referred to as the k-off value.

The term "ka" (M−1×sec-1 or 1/M) refers to the association rate constant of a particular antibody-antigen interaction, or the association rate constant of an antibody, Ig, antibody-binding fragment, or molecular interaction.

The term "KD" or "$K_D$" (M) refers to the equilibrium dissociation constant of a particular antibody-antigen interaction, or the equilibrium dissociation constant of an antibody, Ig, antibody-binding fragment, or molecular interaction. The equilibrium dissociation constant is obtained by dividing the ka with the kd.

A variety of methods of measuring binding affinity are known in the art, any of which can be used for purposes of the present disclosure. For example, binding affinity of an antibody to an antigen can be measured by surface plasmon resonance, e.g., BIACORE™ or solution-affinity ELISA.

In some embodiments, the binding of antibody to a transmembrane protein of interest imparts a functional activity within the cell (in vitro, ex vivo or in vivo) on which the transmembrane protein is expressed, or the binding of antibody with the transmembrane protein of interest modulates the normal functional activity of the transmembrane protein of interest in the presence or in the absence of the transmembrane protein of interest's endogenous ligand.

In certain embodiments, the antibody to the transmembrane protein of interest is an antagonist of transmembrane protein function. An antagonist antibody means an antibody directed against the active site of the antigen (i.e., the transmembrane protein of interest) and that is able to inhibit the activity of the transmembrane protein or that of a natural ligand to the transmembrane protein itself. For instance, binding of the antibody to an antigen will reduce or prohibit the endogenous function of the transmembrane protein of interest. In one non-limiting example, an antagonist antibody can bind to a transmembrane protein of interest, and modulate transmembrane protein function by interfering with ligand binding to the transmembrane protein, receptor activation or the like.

In yet another embodiment, the antibody to the transmembrane protein of interest is a transmembrane protein agonist. An agonist antibody means an antibody able to activate the transmembrane protein of interest (i.e., antigen) in the absence of the native ligand itself where the agonist antibody can induce functional activity of the transmembrane protein of interest. For instance, binding of the antibody to an antigen can induce or increase the endogenous function of the transmembrane protein of interest. In one non-limiting example, an agonist antibody can bind to a transmembrane protein of interest, and can modulate transmembrane protein function by activating the protein or receptor, by for example changing the protein's conformation.

Assays for measuring antibody binding and transmembrane protein function are well known by those of ordinary skill in the art. For example, assays for measuring transmembrane protein internalization, conformation changes, phosphorylation, ligand binding and the like are well known in the art.

The present description is further illustrated by the following examples, which should not be construed as limiting in any way. The contents of all cited references (including literature references, issued patents, and published patent applications as cited throughout this application) are hereby expressly incorporated by reference in their entireties.

EXAMPLES

Example 1. Generating and Collecting Antibody Producing Cells

As shown in Table 1, for comparison several immunization campaigns were initiated to generate an immune response in the mice and generate cells that produced antibody to the antigen of interest (antibody-producing cells). Antibody-producing cells were then collected in accordance with the methods described herein.

Generally, mice were immunized by injection of an immunogen such as, for example, DNA encoding a transmembrane protein of interest or a portion thereof, a purified transmembrane protein of interest or a portion thereof, a lipid-bilayer membrane scaffold protein complex containing a transmembrane protein of interest or a portion thereof, a virus-like particle (VLP) containing the transmembrane protein of interest or cable of expressing DNA encoding the transmembrane protein of interest, or a combination thereof. In some instances, the immunogen was a human transmembrane protein or DNA encoding the same. In other instances, mice were immunized with a chimeric transmembrane protein of interest, a truncated form of a transmembrane protein, a modified transmembrane protein of interest or DNA encoding the same.

Transmembrane proteins for use in the methods described herein were generated as follows. Generally, the nucleotide sequence encoding the transmembrane protein was modified to include a FLAG-tag and histidine-tag (10×-His tag) affixed to the carboxy-terminal of the transmembrane protein. The modified nucleotide sequence was expressed in Sf9 or Expi293 cells (Thermo Fisher Scientific). The cells were then solubilized using N-Dodecyl-β-D-maltoside (DDM) detergent and centrifuged to obtain the detergent soluble fraction containing the modified transmembrane proteins. The modified proteins were then isolated from the detergent soluble fraction by affinity purification with anti-FLAG affinity beads, which bound the modified transmembrane proteins. The affinity beads and proteins were then washed and the bound transmembrane proteins were eluted from and collected. Isolation of purified transmembrane protein was verified by SDS-PAGE gel electrophoresis and Western blotting.

Lipid bilayer-membrane scaffold protein complexes were formed that incorporate a purified transmembrane protein. A purified transmembrane protein was included in a detergent mixture composed of DDM and cholesteryl hemisuccinate tris salt (CHS). This transmembrane protein and detergent mixture was combined with a 1 to 130 membrane scaffold protein to lipid mixture containing modified MSP1E3D1 membrane scaffold protein, which include a Bir-A tag at the carboxy terminal for biotinylation, and phosphatidylcholine (1-palmitoyl-2-oleoyl-glycero-3-phosphocholine) lipids that have been dissolved in sodium cholate detergent buffer to create a final mixture composed of transmembrane protein, detergent, membrane scaffold protein, lipids and buffer containing a ratio of 1 purified transmembrane protein to 20 membrane scaffold proteins. The detergent was then extracted from the final mixture using beads to facilitate the assembly of discoidal lipid-bilayer membrane scaffold protein complexes that integrated a single transmembrane protein of interest. Discoidal lipid-bilayer membrane scaffold protein complexes that incorporated the transmembrane protein of interest were then separated from discoidal lipid-bilayer membrane scaffold protein complexes that did not include a transmembrane protein of interest using 10×-his tag affinity purification and/or size exclusion chromatography to obtain discoidal lipid-bilayer membrane scaffold protein complexes that incorporated the transmembrane protein of interest for further use.

The mice being immunized varied. In certain cohorts, the mice were genetically-engineered such that the transmembrane protein of interest was not expressed from an endogenous gene. In other cohorts, the mice were wild-type mice, which expressed a mouse homolog of the transmembrane protein of interest. In some cohorts, the mice were genetically engineered as set forth in, U.S. Pat. Nos. 8,502,018, 8,642,835, 8,697,940, 8,791,323, 9,226,484, and WO2019/113065; all of which are incorporated herein by reference in their entireties. In some cohorts, the immunized genetically engineered mice were VELOCIMMUNE® mice (Regeneron Pharmaceuticals, Inc., Tarrytown, NY) as described in, for example, U.S. Pat. Nos. 8,502,018, 8,642,835, the entire contents of each of which is incorporated herein by reference. Generally, the VELOCIMMUNE® mice used for immunization comprise DNA encoding human immunoglobulin heavy (IgH) and human immunoglobulin light chain variable regions and can also lack the endogenous mouse gene encoding the transmembrane protein of interest. In specific cohorts, VELOCIMMUNE® mice that included a humanized IgH locus and/or a humanized Igκ locus were immunized. In some cohorts, genetically engineered mice comprising DNA encoding human immunoglobulin heavy and immunoglobulin lambda light chain (Igλ) variable regions, which lack the endogenous mouse gene encoding the transmembrane protein of interest were injected with an immunogen.

The antibody immune response was monitored by a cell binding assay using cells engineered to express the transmembrane protein of interest or a portion, thereof. Once a desired immune response was identified in the immunized mice, their spleens were harvested. Splenocytes were obtained and red blood cells were removed by lysis.

In instances where hybridomas were formed and used, splenocytes were harvested and fused with mouse myeloma cells to preserve their viability and form hybridoma cell lines. The hybridoma cell lines were then screened and selected to identify cell lines that produce antibodies to the transmembrane protein of interest.

Antibody-producing cells were also isolated with antigen-positive B cells. Once mice were immunized, their spleens were harvested. Splenocytes were obtained and red blood cells were removed by lysis. Splenocytes were then stained with fluorochrome-labelled antibodies specific to a B cell surface marker, such as IgG, to identify B cells.

Generally, a population of antibody-producing B cells is then identified by contacting the B cells with either a known sorting agent, such as a purified transmembrane protein or a portion thereof, a chimeric transmembrane protein of interest, a truncated transmembrane protein of interest, a transmembrane protein of interest in a VLP or exosome, or a lipid bilayer-membrane scaffold protein complex incorporating the transmembrane protein of interest or a portion thereof, to permit the transmembrane protein of interest to bind to an antibody present on the surface of a B cell. Bound B cells were then collected using FACS to provide a population of antibody-producing B cells that express antibody to the transmembrane protein of interest. In samples without the complex (control), sorting was performed with peptides or virus-like particles (VLPs) via FACS to obtain antibody-producing B cells from a heterogeneous population of B cells. In samples with complex, sorting was performed with fluorescently labeled complexes via FACS to obtain antibody-producing B cells. Here, B cells were incubated with biotinylated lipid bilayer-membrane scaffold protein complex containing a transmembrane protein of interest. Cells were then washed to remove unbound complex. Subsequently, cells were incubated with PE-streptavidin to enable streptavidin binding to each of the biotin (Bir-A) labeled membrane scaffold proteins in the lipid-bilayer-membrane scaffold protein complex. Cells were then washed in phosphate buffered saline (PBS) to remove excess PE-streptavidin. PE fluorescence of B cell samples were analyzed by FACS to identify a population of cells that expresses antibodies that bind to the transmembrane protein of interest.

Example 2. Generating Antibody from a Population of Antibody Producing Cells

For comparison, antibodies were isolated for screening by either traditional hybridoma technique or cell sorting with or without lipid bilayer-membrane scaffold protein complex. Single cells from a population of antibody-producing B cells were isolated in individual wells on 384-well plates. RT-PCR of antibody genes from these isolated antibody-producing B cells was performed according to the method described by Wang and Stollar *Journal of Immunological Methods* (2000) 244: 217-225, the entire contents of which is hereby incorporated by reference. Briefly, cDNAs for each single antibody-producing B cell were synthesized via reverse transcriptase (RT) reaction (Superscript™ III, Invitrogen). Each resulting RT product was then split and transferred into two corresponding wells on two 384-well plates. One set of the resulting RT products was first amplified by PCR using a 5' degenerate primer specific for human IgG heavy chain variable region leader sequence and a 3' primer specific for mouse heavy chain constant region, to form an amplicon. The amplicon was then amplified again by PCR using a 5' degenerate primer set specific for framework 1 of human IgG heavy chain variable region sequence and a 3' degenerate primer set specific for framework 4 of human IgG heavy chain variable region sequence. The other set of the resulting RT products was first amplified by PCR using a 5' degenerate primer specific for human kappa or lambda light chain variable region leader sequence and a 3' primer specific for mouse kappa or lambda light chain constant region to form an amplicon. The amplicon was then amplified again by PCR using a 5' degenerate primer set specific for framework 1 of human kappa or lambda light chain variable region sequence and a 3' degenerate primer set specific for framework 4 of human kappa or lambda light chain variable region sequence. The heavy chain and light chain PCR products were cloned into antibody vectors containing human IgG1 heavy chain constant region and kappa light chain constant region, respectively. Recombinant human IgG1 antibodies were produced by transient transfection of CHO cells.

The primary screens of antibodies obtained from antibody producing cells were tested for cell binding. Dissociation constants of the binding between a transmembrane protein of interest, and each antibody were determined on Biacore™ T200 (GE Healthcare). The results of several campaigns under varying conditions indicated that cell sorting using a lipid bilayer-membrane scaffold protein complex presenting a transmembrane protein of interest was most successful at identifying antibodies that bind to the transmembrane proteins of interest. See Table 1.

TABLE 1

| Transmembrane Protein of Interest (Antigen) | Platform | Antigen Presentation Strategy | Immunogen | Mouse Strain | Total # of antibodies that bind antigen | % of antibody that bind antigen |
|---|---|---|---|---|---|---|
| GPCR3 | Cell sorting | Complex w/ antigen | Protein | Genetically modified mouse w/out antigen | 118 | 20.0 |
| GPCR3 | Hybridoma | NA | Protein | Genetically modified mouse w/out antigen | 156 | 3.5 |
| GPCR3 | Cell sorting | Complex w/ antigen | Modified DNA | Genetically modified mouse w/out antigen | 63 | 20.6 |
| GPCR3 | Hybridoma | NA | Modified DNA | Genetically modified mouse w/out antigen | 252 | 6.5 |
| GPCR4 | Cell sorting | Complex w/ antigen | Protein | Genetically modified mouse w/out antigen | 313 | 80.5 |
| GPCR4 | Hybridoma | NA | Protein | Genetically modified mouse w/out antigen | 89 | 5.6 |
| GPCR4 | Cell sorting | Complex w/ antigen | Modified DNA | Genetically modified mouse w/out antigen | 213 | 48.4 |
| GPCR4 | Hybridoma | NA | Modified DNA | Genetically modified mouse w/out antigen | 2002 | 36.1 |
| GPCR5 | Cell sorting | Complex w/ antigen | DNA | Genetically modified mouse w/out antigen | 57 | 11.6 |
| GPCR5 | Hybridoma | NA | DNA | Genetically modified mouse w/out antigen | 315 | 7.0 |
| GPCR5 | Cell sorting | Complex w/ antigen | Protein | Genetically modified mouse w/out antigen | 124 | 70.5 |

TABLE 1-continued

| Transmembrane Protein of Interest (Antigen) | Platform | Antigen Presentation Strategy | Immunogen | Mouse Strain | Total # of antibodies that bind antigen | % of antibody that bind antigen |
|---|---|---|---|---|---|---|
| GPCR5 | Hybridoma | NA | Protein | Genetically modified mouse w/out antigen | 299 | 15.4 |
| Ion Channel 2 | Cell sorting | Complex w/ antigen | Protein | Genetically modified mouse | 70 | 39.8 |
| Ion Channel 2 | Hybridoma | NA | Protein | Genetically modified mouse | 308 | 4.3 |
| Ion Channel 2 | Cell sorting | Complex w/ antigen | Protein | Genetically modified mouse | 92 | 69.7 |
| Ion Channel 2 | Hybridoma | NA | Protein | Genetically modified mouse | 43 | 2.4 |
| GPCR6 | Cell sorting | Complex w/ antigen | Protein | Genetically modified mouse w/out antigen | 53 | 18.9 |
| GPCR6 | Hybridoma | NA | Protein | Genetically modified mouse w/out antigen | 8 | 1.0 |
| GPCR6 | Cell sorting | Complex w/ antigen | Modified DNA | Genetically modified mouse w/out antigen | 22 | 9.6 |
| GPCR6 | Hybridoma | NA | Modified DNA | Genetically modified mouse w/out antigen | 10 | 0.6 |
| GPCR1 | Cell sorting | Complex w/ antigen | DNA | Genetically modified mouse w/out antigen | 42 | 11.9 |
| GPCR1 | Hybridoma | NA | DNA | Genetically modified mouse w/out antigen | 82 | 4.4 |
| Ion Channel 1 | Cell sorting | Complex w/ antigen | DNA | Genetically modified mouse w/out antigen | 156 | 14.8 |
| Ion Channel 1 | Hybridoma | NA | DNA | Genetically modified mouse w/out antigen | 19 | 0.3 |
| Tetraspanin1 | Cell sorting | Complex w/ antigen | DNA, Protein, complex w/ antigen | Genetically modified mouse w/out antigen | 81 | 29 |
| Tetraspanin1 | Hybridoma | NA | DNA, Protein, complex w/ antigen | Genetically modified mouse w/out antigen | 162 | 8 |

Example 3. Detecting Binding Between a Transmembrane Protein of Interest Encompassed by a Lipid Bilayer-Membrane Scaffold Protein Complex and an Antibody In this example, the nucleotide sequence encoding an exemplary human transmembrane protein (GPCR1) was modified to affix a FLAG-tag and His-tag (10×-His tag) to the carboxy terminal of the GPCR1 protein sequence and the modified nucleotide sequence was expressed in cells and purified as set forth in Example 1. The exemplary GPCR1 transmembrane protein of interest was then incorporated into a lipid bilayer-membrane scaffold protein complex, and lipid bilayer-membrane scaffold protein complexes encompassing the GPCR1 transmembrane protein of interest were purified as described in Example 1.

The ability of known anti-GPCR1 antibody to bind to lipid bilayer-membrane scaffold protein complexes encompassing the GPCR1 transmembrane protein of interest was confirmed by octet assay, as shown in FIGS. 1A and 1B. Specifically, 38 µg/mL of discoidal lipid bilayer-membrane scaffold protein complex including GPCR1 transmembrane protein or 10 µg/mL of a control discoidal lipid bilayer-membrane scaffold protein complex without GPCR1 (empty complex) was provided to plates with immobilized anti-GPCR1 antibody (positive control AB) or iso-type control antibody (negative control AB).

Binding was detected between the positive control (anti-GPCR1) antibody and discoidal lipid bilayer-membrane scaffold protein complex including GPCR1 transmembrane protein (0.6 nm), and binding was not detected between anti-GPCR1 antibody and empty complex (−0.05 nm), between negative control antibody and discoidal lipid bilayer-membrane scaffold protein complex including GPCR1 transmembrane protein (−0.06 nm), or between negative control antibody and empty complex (−0.03 nm). See FIG. 1A. Confirming that the transmembrane protein of interest presented by the complex, but not the complex itself, binds to antibodies directed to the transmembrane protein of interest.

In order to confirm that biotinylated lipid bilayer-membrane scaffold protein complexes presenting a transmembrane protein of interest can be detected and isolated from control lipid bilayer-membrane scaffold protein complex biotinylated control lipid bilayer-membrane scaffold protein complex (empty complex), biotinylated lipid bilayer-membrane scaffold protein complex presenting a GPCR1 transmembrane protein (complex with GPCR1) or control lipid bilayer-membrane scaffold protein complex biotinylated control lipid bilayer-membrane scaffold protein complex (empty complex) was provided to plates having streptavidin tethered thereto to enable binding of streptavidin to the Bir-A tag affixed to the membrane scaffold protein in the complex. The plates were then incubated with either 50 μg/mL of anti-GPCR1 antibody (positive control AB) or 50 μg/mL of iso-type control antibody (negative control AB). See FIG. 1B.

First, FIG. 1B demonstrates that biotinylated lipid bilayer-membrane scaffold protein complexes presenting a GPCR1 transmembrane protein of interest and biotinylated control lipid bilayer-membrane scaffold protein complexes can be detected and isolated by streptavidin binding to the Bir-A tag affixed to each of the membrane scaffold proteins in the complex. This is shown by detecting binding between the tethered streptavidin and both biotinylated discoidal lipid bilayer-membrane scaffold protein complex including GPCR1 transmembrane protein (3.0 nm) and biotinylated empty complex (0.69 nm).

Binding was detected between the positive control (anti-GPCR1) antibody and biotinylated discoidal lipid bilayer-membrane scaffold protein complex including GPCR1 transmembrane protein tethered to the streptavidin plate (0.69 nm) but binding was not detected between anti-GPCR1 antibody and biotinylated empty complex (−0.04 nm), between negative control antibody and biotinylated discoidal lipid bilayer-membrane scaffold protein complex including transmembrane protein (−0.05 nm), or between negative control antibody and empty biotinylated complex (−0.06 nm). See FIG. 1B, demonstrating that biotinylated lipid bilayer-membrane scaffold protein complexes tethered to a streptavidin plate, which present a transmembrane protein of interest specifically bind to the anti-GPCR1 antibody but not control antibody.

Example 4. Obtaining Antibody Producing Cells that Express Antibody that Specifically Bind Exemplary Transmembrane Proteins of Interest The nucleotide sequence encoding a first, second and third exemplary human transmembrane protein was modified to affix a FLAG tag and His tag (10×-His tag) to the carboxy terminal of the transmembrane protein and the modified nucleotide sequence was expressed in cells and purified as set forth in Example 1. Lipid bilayer-membrane scaffold protein complexes encompassing either the first, second or third exemplary transmembrane protein of interest were generated using Bir-A labeled membrane scaffold proteins, and purified as described in Example 1 and 3.

Splenocytes were harvested from genetically modified VELOCIMMUNE® mice including a humanized IgH locus and/or a humanized Igκ locus that lack the endogenous mouse gene encoding the transmembrane protein of interest. Cells were isolated from control mice that were not immunized or genetically modified mice that have been immunized by injection of: DNA encoding a first transmembrane protein of interest (GPCR1), a second transmembrane protein of interest (GPCR2), or a third transmembrane protein of interest (GPCR3). Here, each mouse was genetically modified. The splenocytes collected from each mouse were stained with fluorescent labels to B cell markers (i.e., anti-IgG antibody) and at the same time incubated with 0.2 mg/ml to 5.0 mg/mL biotinylated lipid bilayer-membrane scaffold protein complex containing a transmembrane protein embedded therein. Cells were then washed to remove unbound complex. Subsequently, cells were incubated with PE-streptavidin to enable streptavidin binding to each of the biotin (Bir-A) labeled membrane scaffold proteins in the lipid-bilayer-membrane scaffold protein complex. Cells were then washed in phosphate buffered saline (PBS) to remove excess PE-streptavidin. PE fluorescence of cell populations from control mice and immunized mice was detected by FACS to identify a population of B-cells that express antibodies that bind a transmembrane protein of interest presented by a biotinylated lipid bilayer-membrane scaffold protein complex. See FIGS. 2A-2F.

Figure 2A:
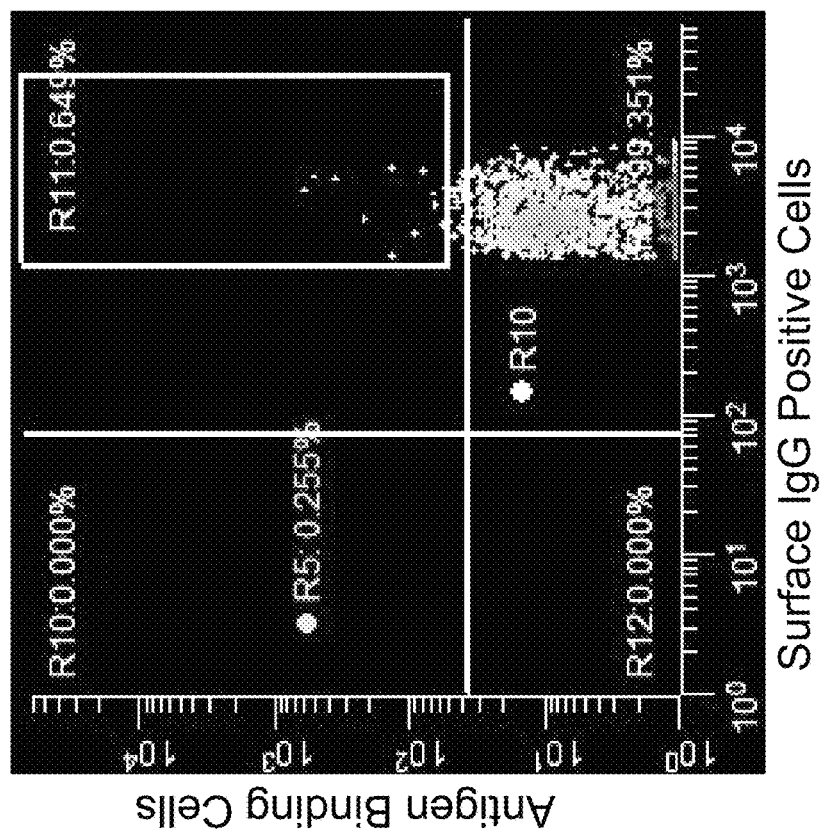
Figure 2B:
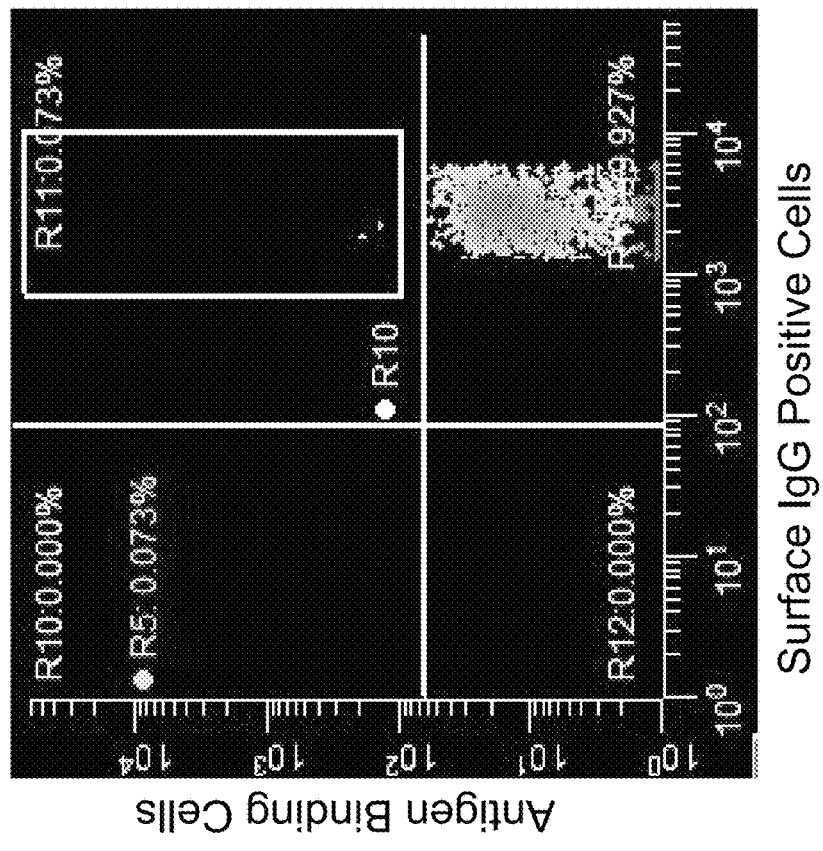

Only two B cells in one million control cells bound non-specifically to a GPCR1 transmembrane protein presented by a biotinylated lipid bilayer-membrane scaffold protein complex (FIG. 2A, rectangle), demonstrating that lipid bilayer-membrane scaffold protein complexes containing a transmembrane protein of interest are a highly specific sorting reagent for detecting and isolating cells that produce antibodies directed to the transmembrane protein antigen. By comparison, 11 out of one million, antibody-producing B cells which bound to a first transmembrane protein of interest presented by a biotinylated lipid bilayer-membrane scaffold protein complex were detected using the present methods (FIG. 2B, rectangle).

Figure 2C:
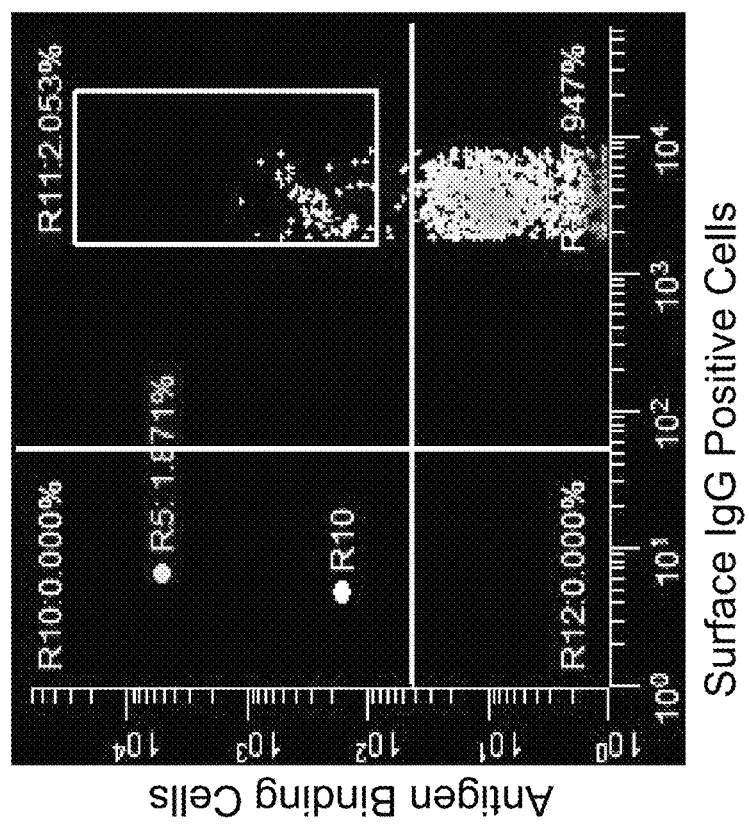
Figure 2D:
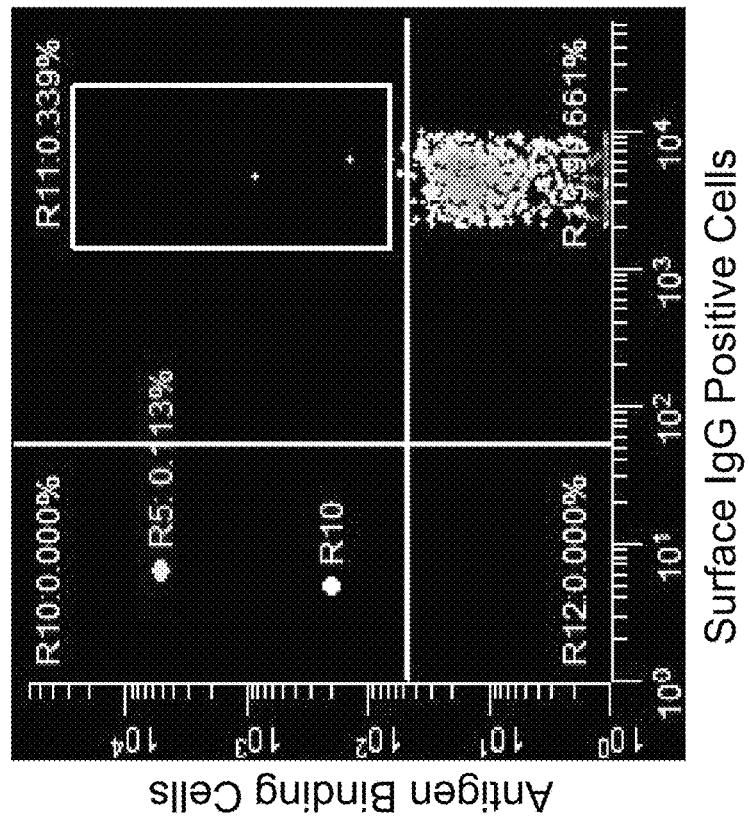
Figure 2E:
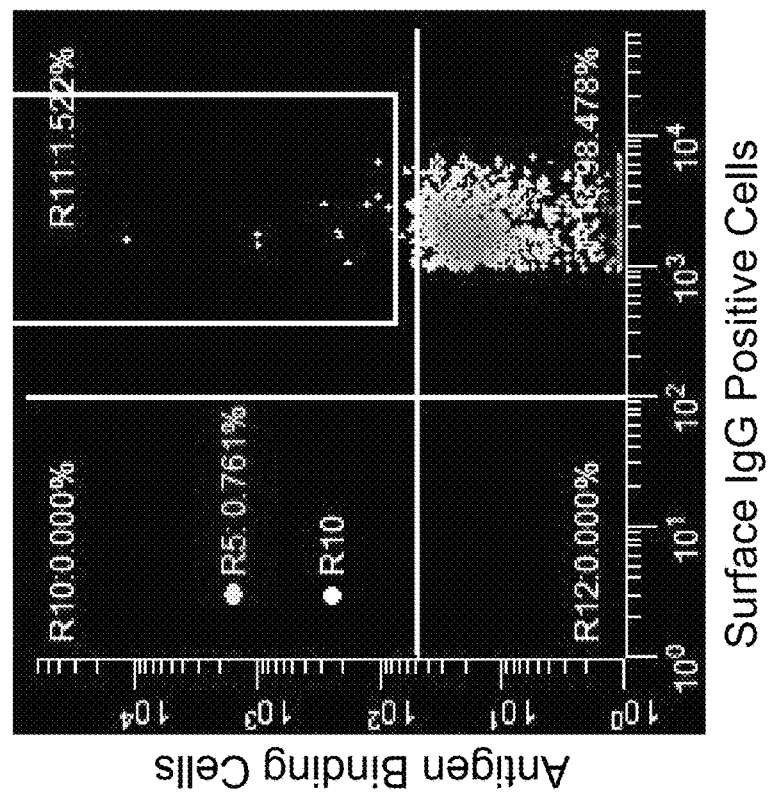
Figure 2F:
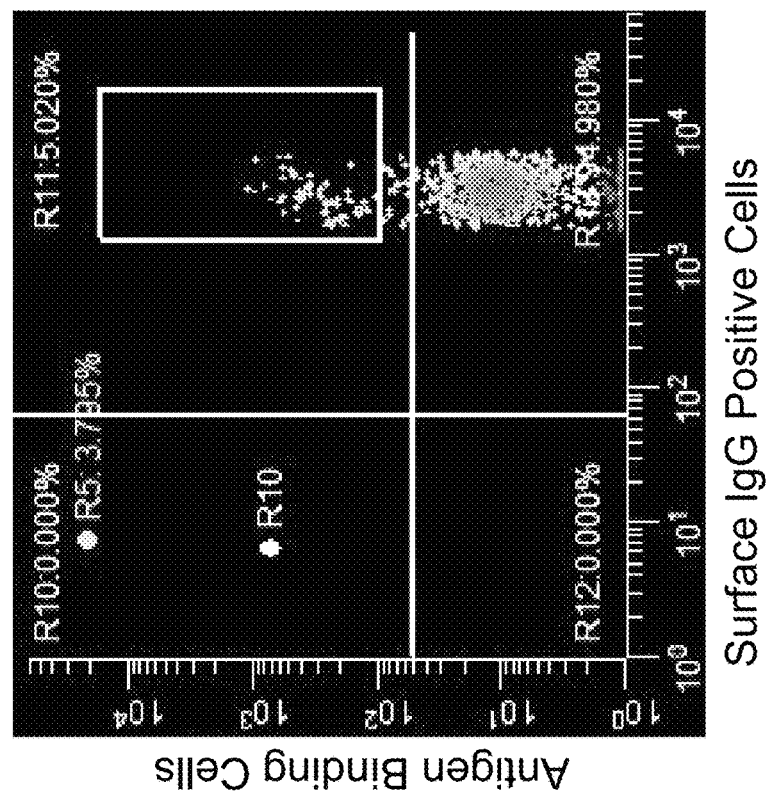

As shown in FIG. 2C, two B cells in one million splenocytes obtained from a control mouse were detected as non-specific binders to biotinylated lipid bilayer-membrane scaffold protein complex presenting the second transmembrane protein of interest (rectangle). In contrast, seventy-eight out of one million B cells expressing antibody specific to the second exemplary GPCR transmembrane protein of interest (GPCR2) were detected using the present methods (rectangle), as shown in FIG. 2D.

In yet another example, only eleven B cells that bound non-specifically to biotinylated lipid bilayer-membrane scaffold protein complex presenting the third transmembrane protein of interest (rectangle) were obtained from one million splenocytes harvested from a control mouse. See FIG. 2E. Whereas, sixty-five out of one million B cells expressing a primary-antibody specific to a third exemplary GPCR transmembrane protein of interest (GPCR3) were detected and obtained from splenocytes harvested from an immunized genetically modified mouse.

Example 5. Comparison of Known Cell-Sorting Strategies to Sorting Methods that Include the Use of Lipid Bilayer-Membrane Scaffold Protein Complexes In order to compare the utility of methods for obtaining antibody-producing cells known in the art to the inventive methods disclosed herein, DNA encoding an exemplary human transmembrane protein of interest was purified according to Example 1. For immunization of mouse cohorts with DNA encoding the transmembrane protein of interest, the purified human DNA was injected into genetically engineered VELOCIMMUNE® mice that express or do not express the endogenous mouse gene encoding the transmembrane protein of interest. For cohorts immunized with the transmembrane protein of interest, the nucleotide sequence encoding the first exemplary human transmembrane protein was expressed in cells, purified as set forth in Example 1 and administered directly to genetically engineered VELOCIMMUNE® mice that express or do not express the endogenous mouse gene encoding the transmembrane protein of interest by injection.

In certain cohorts, mice were immunized with VLPs. A plasmid containing DNA encoding the human transmembrane protein of interest was generated and expressed in viral cells. Lipoparticles were self-assembled in the viral cells, isolated and purified from the viral cells once budding occurred by pegylation (PEG) precipitation, followed by isopycnic centrifugation and fractionation of viral cell medium. The purified VLPs were injected into mice for immunization using known techniques.

For comparison, genetically engineered VELOCIMMUNE® mice comprising DNA encoding human immunoglobulin heavy (IgH) and human immunoglobulin light chain variable regions, with (VI) or without (VI—KO) the endogenous mouse gene encoding the transmembrane protein of interest, were immunized by injection as set forth in Table 2.

Next, a population of antibody-producing B cells was isolated using the sorting strategy described in Table 2. Specifically, splenocytes were collected from the immunized genetically modified mice. The collected splenocytes were stained with fluorescent labels to B cell markers (i.e., anti-IgG antibody) and at the same time incubated with 0.2 mg/ml to 5.0 mg/mL of a biotinylated transmembrane protein of interest sorting agent (Protein) or 0.2 mg/ml to 5.0 mg/mL of a biotinylated lipid bilayer-membrane scaffold protein complex encompassing the transmembrane protein of interest (Complex w/TMB) or 2.0 mg/mL to 20 mg/mL of biotin labeled VLP sorting agent (VLP), as set forth in Table 2. Cells were then washed to remove unbound sorting agent. Subsequently, cells were incubated with PE-streptavidin to enable streptavidin binding to each of the biotin (Bir-A) labeled sorting agent. Cells were washed in phosphate buffered saline (PBS) to remove excess PE-streptavidin and PE fluorescence of B cell samples were analyzed by FACS to identify B cells in a heterogeneous population of cells that express antibodies that bind to the transmembrane protein of interest presented by the sorting agent.

Single antibody producing B-cells that bound to a transmembrane protein of interest were then isolated to individual wells on 384-well plates as set forth in Example 2. RT-PCR of antibody genes from these B-cells was performed according to a method described by Wang and Stollar *Journal of Immunological Methods* (2000) 244: 217-225. Briefly, cDNAs for each single B cell were synthesized via reverse transcriptase (RT) reaction (Superscript™ III, Invitrogen). Each resulting RT product was then split and transferred into two corresponding wells on two 384-well plates. One set of the resulting RT products was first amplified by PCR using a 5' degenerate primer specific for human IgG heavy chain variable region leader sequence and a 3' primer specific for mouse heavy chain constant region, to form an amplicon. The amplicon was then amplified again by PCR using a 5' degenerate primer set specific for framework 1 of human IgG heavy chain variable region sequence and a 3' degenerate primer set specific for framework 4 of human IgG heavy chain variable region sequence. The other set of the resulting RT products was first amplified by PCR using a 5' degenerate primer specific for human kappa or lambda light chain variable region leader sequence and a 3' primer specific for mouse kappa or lambda light chain constant region to form an amplicon. The amplicon was then amplified again by PCR using a 5' degenerate primer set specific for framework 1 of human kappa or lambda light chain variable region sequence and a 3' degenerate primer set specific for framework 4 of human kappa or lambda light chain variable region sequence. The heavy chain and light chain PCR products were cloned into antibody vectors containing human IgG1 heavy chain constant region and kappa light chain constant region, respectively. Recombinant human IgG1 antibodies were produced by transient transfection of CHO K1 cells and analyzed for their ability to bind the transmembrane protein of interest.

TABLE 2

| Transmembrane Protein (TMB) | Mouse Strains | # Mice | Immunogen | Sorting Agent | Total # of Antibodies that Bind the TMB |
| --- | --- | --- | --- | --- | --- |
| GPCR1 | VI | 9 | VLP and DNA | VLP | None |
| GPCR1 | VI | 9 | Protein | Protein | 176 |
| GPCR1 | VI-KO | 3 | DNA | Complex w/TMB | 42 |
| Ion Channel 2 | VI-KO | 15 | Protein | Protein | 1 |
| Ion Channel 2 | VI-KO | 14 | Protein | Protein | 1 |
| Ion Channel 2 | VI-KO | 4 | Protein | Complex w/TMB | 236 |
| Ion Channel 2 | VI-KO | 4 | Protein | Complex w/TMB | 167 |

Table 2 demonstrates that methods for obtaining antibody-producing cells that utilize a lipid bilayer-membrane scaffold protein complex to present the transmembrane protein detect more antibody-producing cells that express antibody that specifically binds to the transmembrane of interest when compared to other sorting agents, independent of the immunogen used.

Cells sorted with a purified transmembrane protein sorting agent that were obtained from genetically modified mice that express the endogenous mouse gene encoding the transmembrane protein of interest (VI) generated more antibodies that bound to the transmembrane protein of interest, when compared to those obtained from genetically modified mice that did not express the endogenous mouse gene encoding the transmembrane protein of interest (VI—KO) and sorted with a lipid bilayer-membrane scaffold protein complex that presented the transmembrane protein. However, when analyzed, the antibodies generated from the VI mice were not functional binders. Demonstrating that methods for obtaining antibody-producing cells that use a lipid bilayer-membrane scaffold protein complex to present the transmembrane protein obtain antibodies that bind to functionally relevant epitopes of the transmembrane protein.

Example 6. Generating and Isolating Antibodies that Bind a Second Exemplary GPCR Transmembrane Protein of Interest The nucleotide sequence encoding a second exemplary GPCR transmembrane protein of interest (GPCR2) was modified as set forth in Example 1 to include a FLAG tag and a 10x-His tag affixed to the carboxy terminal of the GPCR2 protein. Additionally, the following stabilizing mutations were introduced into the transmembrane protein: amino acid substitutions: A2a-T4L-delta, as described in Veli-Pekka Jaakola et al., Science, Nov. 21, 2008; 322(5905) pp. 1211-1217, the entire contents of which is expressly incorporated herein by reference. The modified GPCR2 nucleotide sequence was cloned into an expression vector and expressed in Sf9 cells. The cells were then solubilized, and the modified GPCR2 transmembrane proteins were obtained and purified as in Example 1.

Next, discoidal lipid-bilayer membrane scaffold protein complexes containing modified human GPCR2 transmembrane protein were generated as set forth in Example 1 and herein.

Genetically modified GPCR2 knock-out mice, i.e., VELOCIMMUNE® mouse including a humanized IgH locus and a humanized Igκ locus that also lack the endogenous mouse gene encoding the transmembrane protein of interest, were immunized by injection of exogenous DNA encoding the modified human GPCR2 protein including stabilizing mutations (DNA immunogen) or injection of the modified human GPCR2 protein including stabilizing mutations (Protein immunogen) as shown in Table 3.

Splenocytes were collected from each mouse and stained with fluorescent labels to B cell markers (i.e., anti-IgG antibody) and at the same time incubated with 0.2 mg/ml to 5.0 mg/mL biotinylated lipid bilayer-membrane scaffold protein complex containing a transmembrane protein embedded therein. Cells were then washed to remove unbound complex. Subsequently, cells were incubated with PE-streptavidin to enable streptavidin binding to each of the biotin (Bir-A) labeled membrane scaffold proteins in the lipid-bilayer-membrane scaffold protein complex. Cells were then washed in phosphate buffered saline (PBS) to remove excess PE-streptavidin. PE fluorescence of cell populations from control mice and immunized mice was detected by FACS to identify a population of B cells that express antibodies that bind to the second exemplary GPCR transmembrane protein of interest presented by a biotinylated lipid bilayer-membrane scaffold protein complex.

Single antibody producing B cells that bound to the transmembrane protein of interest were then isolated to individual wells on 384-well plates, antibody encoding DNA was isolated from each cell, antibodies were generated as set forth in Example 2 for further analysis.

FIG. 3 demonstrates that the inventive methods for obtaining antibody-producing cells detect antibody-producing cells that express antibody that specifically binds to the transmembrane of interest, independent of the type of immunogen used. Specifically antibody-producing cells were obtained from genetically engineered mice immunized with either DNA encoding the transmembrane protein (DNA) or a purified transmembrane protein of interest (Protein) using a biotinylated lipid bilayer-membrane scaffold protein complex presenting an the transmembrane protein of interest according to the disclosed methods. Antibodies were generated for screening as set forth in Example 2. A full-length transmembrane protein of interest antigen was expressed in 293 cells (TMB over-expressed) using standard transfection techniques and antigen-expressing 293 cells were compared to control 293 cells that were not transfected with DNA encoding the exemplary transmembrane protein of interest (parental cells). Cells were then incubated with antibodies to permit binding between antigen on the surface of the cells and an antibody that specifically bind the exemplary transmembrane protein of interest. A MSD (Meso scale diagnostics) immunoassay was carried out according to manufacturers to identify cell-binding antibodies generated from antibody-producing cells obtained from 5 different immunized mice. Mouse 1, 3, 4 and 5 were immunized with purified human GPCR2 transmembrane protein, while mouse 2 was immunized with DNA encoding human GPCR2 transmembrane protein. Antibodies above the dashed line were capable of binding the transmembrane protein of interest. In contrast, antibodies below the dashed line were weak binders or unable to bind the transmembrane protein of interest, as indicated by comparison to the positive (square) and negative (triangle) control antibodies.

The results show that antibody-producing cells obtained using the inventive methods produced ample amounts of antibodies capable of binding the transmembrane protein of interest (above the dashed line), regardless of whether the mice were immunized with DNA encoding the transmembrane protein of interest or the transmembrane protein of interest.

As shown in Table 3, B cells were obtained from each immunized mouse using a biotinylated lipid bilayer-membrane scaffold protein complex that present the transmembrane protein (Complex w/TMB), antibodies were generated from a subset of the B cells collected and the antibodies were tested by immunoassay for the ability to bind to the antigen of interest. Antibody-producing cells that express antibody that specifically bind to the transmembrane protein of interest (antigen) were obtained in abundance using the inventive methods regardless of whether the mice were immunized with DNA encoding the transmembrane protein or purified transmembrane protein.

TABLE 3

| Mouse | Immunogen | Sorting Agent | # Antibody-producing cells | # Antibodies Tested | # Antigen Binding Antibodies | % Antibody that bind antigen |
| --- | --- | --- | --- | --- | --- | --- |
| 1 | Protein | Complex w/TMB | 723 | 141 | 59 | 42 |
| 2 | DNA | Complex w/TMB | 561 | 140 | 88 | 63 |
| 3 | Protein | Complex w/TMB | 880 | 141 | 98 | 70 |
| 4 | Protein | Complex w/TMB | 1040 | 141 | 99 | 70 |
| 5 | Protein | Complex w/TMB | 640 | 141 | 102 | 72 |
| Total | | | 3844 | 704 | 446 | 63 |

Example 7. Obtaining Antibody Producing Cells that Express Antibody that Binds a Specific Domain of a Transmembrane Protein of Interest The inventive methods were also used to generate antibodies that specifically bind to an epitope located on a particular domain of a transmembrane protein of interest.

In a first instance, the nucleotide sequence encoding a full-length human transmembrane protein (full-length TMB) was modified to affix a FLAG-tag and His-tag (10×-His tag) to the carboxy-terminal of the transmembrane protein, purified and isolated as set forth in Example 1. In addition, the nucleotide sequence encoding a truncated human transmembrane protein missing the extracellular portion of the N-terminus (truncated TMB) was further modified to affix a FLAG-tag and His-tag (10×-His tag) to the carboxy-terminal of the transmembrane protein and the modified nucleotide sequence was expressed in cells and purified as set forth in Example 1. Lipid bilayer-membrane scaffold protein complexes encompassing the truncated TMB were generated using Bir-A labeled membrane scaffold proteins, and purified as described in Examples 1 and 3. Here, the truncated TMB protein includes each of the extracellular loop domains, the transmembrane domains and the intracellular C-terminal domain of the wild-type human transmembrane protein but not the extracellular N-terminal domain. Therefore, lipid bilayer-membrane scaffold protein complexes encompassing the truncated TMB present only the extracellular loop domains of the wild-type human transmembrane protein to a cell.

Genetically-engineered VELOCIMMUNE® mice including DNA encoding human immunoglobulin heavy (IgH) and human immunoglobulin light chain variable regions were immunized with DNA encoding the full-length TMB. Immune response was monitored, and splenocytes were harvested from the immunized mice. The splenocytes collected from each mouse were stained with fluorescent labels to B cell markers (i.e., anti-IgG antibody) and at the same time incubated with 0.2 mg/ml to 5.0 mg/mL biotinylated lipid bilayer-membrane scaffold protein complex presenting the truncated TMB embedded therein to permit binding between an epitope on the extracellular domain of the truncated TMB and an antibody on the surface of a B cell. Cells were then washed to remove unbound complex. Subsequently, cells were incubated with PE-streptavidin to enable streptavidin binding to each of the biotin (Bir-A) labeled membrane scaffold proteins in the lipid-bilayer-membrane scaffold protein complex. Cells were then washed in phosphate buffered saline (PBS) to remove excess PE-streptavidin. PE fluorescence of cell populations collected from the mice was detected by FACS to identify a population of B cells that express antibodies specific to an extracellular loop domain of the transmembrane protein of interest.

Single antibody-producing B cells that bound to the transmembrane protein of interest were then isolated to individual wells on 384-well plates, antibody encoding DNA was isolated from each cell, and antibodies were generated as set forth in Example 2 for further analysis.

As shown in FIG. 4, antibodies that bind an epitope located in an extracellular loop domain of the exemplary transmembrane protein of interest were obtained using the inventive methods (box).

In another instance, the nucleotide sequence encoding a full-length human transmembrane protein (full-length TMB) is modified to affix a FLAG tag and His tag (10×-His tag) to the carboxy terminal of the transmembrane protein, purified and isolated as set forth in Example 1. In addition, the nucleotide sequence encoding a portion of the human transmembrane protein (TMB-Fragment) is generated and the TMB-Fragment nucleotide sequence is expressed in cells and purified as set forth in Example 1. Here, the TMB-fragment polypeptide TMB corresponds to the N-terminus portion of the full-length transmembrane protein of interest.

Lipid bilayer-membrane scaffold protein complexes encompassing the full-length TMB are generated using Bir-A labeled membrane scaffold proteins, and purified as described in Examples 1 and 3.

Genetically modified VELOCIMMUNE® mice including DNA encoding human immunoglobulin heavy (IgH) and human immunoglobulin light chain variable regions, are immunized with DNA encoding the full-length TMB or purified full-length TMB protein. Immune response is monitored, and splenocytes are harvested from the immunized mice. The splenocytes collected from each mouse are incubated with the TMB-Fragment to permit binding between the TMB-Fragment and antibody on the surface of the cells that are specific to an epitope located on the N-terminus of the full-length TMB. This step effectively blocks all antibody-producing cells that express antibody specific to an epitope in the N-terminus domain of the full-length TMB from binding to the full-length TMB presented by the biotinylated lipid bilayer-membrane scaffold protein complex containing the embedded full-length TMB. Cells are then stained with fluorescent labels to B cell markers (i.e., anti-IgG antibody) to identify antibody-producing B-cells in the splenocyte population and also incubated with 0.2 mg/ml to 5.0 mg/mL biotinylated lipid bilayer-membrane scaffold protein complexes encompassing the full-length TMB to permit binding between an epitope on an extracellular loop domain of the full-length TMB and an antibody on the surface of an antibody-producing B cell. Cells are then washed to remove unbound complex. Cells are incubated with PE-streptavidin to enable streptavidin binding to each of the biotin (Bir-A) labeled membrane scaffold proteins in the lipid-bilayer-membrane scaffold protein complex. Cells are then washed in phosphate buffered saline (PBS) to remove excess PE-streptavidin and cells bound to the TMB-fragment from the sort. PE fluorescence of cell populations collected from the mice are detected by FACS to identify a population of antibody-producing B cells that express antibodies specific to an extracellular loop domain of the transmembrane protein of interest.

Single antibody-producing B cells that bind to the transmembrane protein of interest are then isolated to individual wells on 384-well plates, antibody encoding DNA is isolated from each cell, and antibodies are generated as set forth in Example 2 for further analysis.

In another instance, a chimeric transmembrane protein of interest composed of a portion of a human transmembrane protein of interest and a portion of a mouse homolog of the transmembrane protein of interest is used to generate antibodies that specifically bind to an epitope located on a particular domain of a transmembrane protein of interest.

Here, the chimeric transmembrane protein is created by generating a nucleotide sequence encoding a portion of a human transmembrane protein of interest operably linked to a portion of the mouse homolog of the transmembrane protein of interest and further modifying the nucleotide sequence to affix a FLAG tag and His tag (10×-His tag) to the carboxy terminal of the chimeric transmembrane protein. The nucleotide sequence is then purified and isolated as set forth in Example 1. In addition, the nucleotide sequence encoding the chimeric transmembrane protein is expressed in cells and purified as set forth in Example 1 to generate labeled chimeric transmembrane protein of interest (chimeric-TMB). In this instance, the chimeric transmembrane protein of interest has an N-terminus that corresponds to the mouse homolog of the transmembrane protein and extracellular loop domains, transmembrane domains and an intracellular C-terminal domain corresponding to the human transmembrane protein of interest.

In addition, the nucleotide sequence encoding the wild-type human transmembrane protein (human-TMB) is modified to affix a FLAG tag and His tag (10x-His tag) to the carboxy terminal of the transmembrane protein, purified and isolated; then the nucleotide sequence the nucleotide sequence encoding the human transmembrane protein is expressed in cells and purified as set forth in Example 1.

Lipid bilayer-membrane scaffold protein complexes encompassing the human-TMB or the chimeric-TMB are generated using Bir-A labeled membrane scaffold proteins, and purified as described in Examples 1 and 3.

Genetically modified VELOCIMMUNE® mice including DNA encoding human immunoglobulin heavy (IgH) and human immunoglobulin light chain variable regions, are immunized with DNA encoding the human-TMB or purified human-TMB protein. Immune response is monitored, and splenocytes are harvested from the immunized mice. The splenocytes collected from each mouse are stained with fluorescent labels to B cell markers (i.e., anti-IgG antibody) and at the same time incubated with biotinylated lipid bilayer-membrane scaffold protein complexes encompassing the chimeric-TMB to permit binding between an epitope on a human portion of the chimeric-TMB presented by the complex and an antibody on the surface of a B cell. Cells are then washed to remove unbound complex.

Cells are incubated with PE-streptavidin to enable streptavidin binding to each of the biotin (Bir-A) labeled membrane scaffold proteins in the lipid-bilayer-membrane scaffold protein complex. Cells are then washed in phosphate buffered saline (PBS) to remove excess PE-streptavidin and cells bound to the TMB-fragment from the sort. PE fluorescence of cell populations collected from the mice are detected by FACS to identify a population of antibody-producing B cells that express antibodies specific to an extracellular loop domain of the transmembrane protein of interest.

This immunization and sorting strategy effectively removes all antibody-producing B cells that express antibody specific to an epitope of the human-TMB located on a mouse portion of the chimeric-TMB.

In another immunization and sorting strategy, genetically modified VELOCIMMUNE® mice including DNA encoding human immunoglobulin heavy (IgH) and human immunoglobulin light chain variable regions, are immunized with DNA encoding the chimeric-TMB or purified chimeric-TMB protein. Immune response is monitored, and splenocytes are harvested from the immunized mice. The splenocytes collected from each mouse are stained with fluorescent labels to B cell markers (i.e., anti-IgG antibody) and at the same time incubated with biotinylated lipid bilayer-membrane scaffold protein complexes encompassing the human-TMB to permit binding between an epitope located on an extracellular portion of the human-TMB presented by the complex and an antibody on the surface of a B cell. Cells are then washed to remove unbound complex.

Cells are incubated with PE-streptavidin to enable streptavidin binding to each of the biotin (Bir-A) labeled membrane scaffold proteins in the lipid-bilayer-membrane scaffold protein complex. Cells are then washed in phosphate buffered saline (PBS) to remove excess PE-streptavidin from the sort. PE fluorescence of cell populations collected from the mice are detected by FACS to identify a population of antibody-producing B cells that express antibodies specific to an extracellular loop domain of the human transmembrane protein of interest.

This particular immunization and sorting strategy also effectively removes all antibody-producing B cells that express antibody specific to an epitope located on a mouse portion of the chimeric-TMB.

Single antibody-producing B cells that bind to the transmembrane protein of interest presented by the complex can then be isolated to individual wells on 384-well plates, and antibody encoding DNA isolated from each cell, for the generation and analysis of antibody as per Example 2.

Example 8: Obtaining Antibody-Producing Cells that Express Cross-Reactive Antibody Specific to a Transmembrane Protein of Interest The inventive methods were also used to generate antibodies that recognize both mouse and human forms of an exemplary transmembrane protein of interest.

The nucleic acids encoding two different exemplary human transmembrane proteins, human TMB1, and human TMB2 were modified to affix a FLAG tag and His tag (10x-His tag) to the carboxy terminal of each human transmembrane protein amino acid sequence were purified as set forth in Example 1. In addition, the nucleic acids encoding the mouse homolog of each of the two human transmembrane proteins, mouse TMB1 and mouse TMB2, were modified to affix a FLAG tag and His tag (10x-His tag) to the carboxy terminal of each mouse transmembrane protein amino acid sequence and the modified nucleotide sequence was purified as set forth in Example 1. Next, the nucleic acids encoding human TMB1, human TMB2, mouse TMB1 and mouse TMB2, respectively, were each expressed in cells, and each protein was isolated and purified as set forth in Example 1. Lipid bilayer-membrane scaffold protein complexes encompassing one of the human TMB1 protein, the human TMB2 protein, the mouse TMB1 protein and the mouse TMB2 protein were generated using Bir-A labeled membrane scaffold proteins, and purified as described in Example 1.

Genetically-engineered VELOCIMMUNE® mice including DNA encoding human immunoglobulin heavy (IgH) and human immunoglobulin light chain variable regions, which do not express the endogenous mouse homolog to the transmembrane protein of interest (i.e, mouse TMB1 or mouse TMB2) were immunized by injection of exogenous DNA encoding a mouse or human transmembrane protein, or a combination of exogenous DNA encoding the human TMB1 protein and the mouse TMB2 protein as set forth in Table 4.

Immune response was monitored, and splenocytes were harvested from the immunized mice. The splenocytes collected from each mouse were stained with fluorescent labels to B cell markers (i.e., anti-IgG antibody) and at the same time incubated with biotinylated lipid-bilayer membrane scaffold protein complexes including either a specific human TMB protein (Complex w/human TMB) or a specific mouse TMB protein (Complex w/mouse TMB) to permit binding between an the transmembrane protein of interest presented by the biotinylated lipid-bilayer membrane scaffold protein complexes and an antibody on the surface of a B cell. Cells were then washed to remove unbound complex and incubated with PE-streptavidin to enable streptavidin binding to each of the biotin (Bir-A) labeled membrane scaffold proteins in the lipid-bilayer-membrane scaffold protein complex. Cells were then washed in phosphate buffered saline (PBS) to remove excess PE-streptavidin from the sort. PE fluorescence of cell populations collected from the mice were detected by FACS to identify a population of antibody-producing B cells that express antibodies specific to the transmembrane protein of interest.

Single antibody-producing B cells that bound to the transmembrane protein of interest were then isolated to individual wells on 384-well plates, antibody encoding DNA was isolated from each cell, and antibodies were generated as set forth in Example 2 for further analysis.

As shown in Table 4, immunization of genetically modified mice with DNA encoding mouse TMB1 alone and sorting of antibody-producing B cells with a lipid-bilayer membrane scaffold protein complex presenting human TMB1 protein, identified antibody producing B cells that express cross-reactive antibody capable of binding the mouse TMB1 and the human TMB1 protein.

In addition, immunization of genetically modified mice with DNA encoding mouse TMB1 protein and DNA encoding the human TMB1 protein together, and sorting of antibody-producing B cells with either a lipid-bilayer membrane scaffold protein complex presenting human TMB1 protein or a lipid-bilayer membrane scaffold protein complex presenting mouse TMB1 protein, identified antibody-producing B cells that express cross-reactive antibody capable of binding the mouse TMB1 and the human TMB1 protein.

Table 4 also shows that, immunization of genetically modified mice with DNA encoding mouse TMB2 alone and sorting of antibody-producing B cells with a lipid-bilayer membrane scaffold protein complex presenting human TMB2 protein or sorting of antibody-producing B cells with a lipid-bilayer membrane scaffold protein complex presenting mouse TMB2 protein, identified antibody-producing B cells that express cross-reactive antibody capable of binding the mouse TMB2 and the human TMB2 protein. Immunization of genetically modified mice with DNA encoding human TMB2 alone and sorting of antibody-producing B cells with a lipid-bilayer membrane scaffold protein complex presenting human TMB2 protein or sorting of antibody-producing B cells with a lipid-bilayer membrane scaffold protein complex presenting mouse TMB2 protein, also identified antibody-producing B cells that express cross-reactive antibody capable of binding the mouse TMB1 and the human TMB1 protein.

TABLE 4

| Mouse | Immunogen | Antigen Presentation Strategy | # Antibody-producing cells | # Antibodies Tested | # Antigen Binding Antibodies | % Antibody that Bind Antigen |
|---|---|---|---|---|---|---|
| VI-KO | DNA Mouse TMB1 | Complex w/ Human TMB1 | 240 | 131 | 15 | 11 |
| VI-KO | DNA Mouse TMB1 & DNA Human TMB1 | Complex w/ mouse TMB1 | 97 | 66 | 3 | 5 |
| VI-KO | DNA Mouse TMB1 & DNA Human TMB1 | Complex w/ Human TMB1 | 111 | 66 | 3 | 5 |
| VI-KO | DNA Mouse TMB2 | Complex w/ Human TMB2 | 257 | 146 | 42 | 29 |
| VI-KO | DNA Mouse TMB2 | Complex w/ mouse TMB2 | 624 | 166 | 4 | 2 |
| VI-KO | DNA Human TMB2 | Complex w/ Human TMB2 | 736 | 213 | 77 | 36 |
| VI-KO | DNA Human TMB2 | Complex w/ mouse TMB2 | 309 | 125 | 25 | 20 |

Example 9: Obtaining Antibody-Producing Cells that Express Antibody Specific to a Transmembrane Protein of Interest from Mice Immunized with a Lipid-Bilayer Membrane Scaffold Protein Complex Containing the Transmembrane Protein In order to determine whether or not a lipid bilayer-membrane scaffold protein complex encompassing a transmembrane protein of interest could be used as an immunogen to obtain antibody-producing cells that express antibody specific to the transmembrane protein of interest, the nucleotide sequence encoding the exemplary human transmembrane protein, human TMB2 comprising a FLAG tag and His tag (10×-His tag) affixed to the carboxy terminal thereof were generated and purified as set forth in Example 8. The nucleotide sequence encoding the modified human TMB2 protein was expressed in cells, and the modified TMB2 protein was isolated and purified as set forth in Example 8. Lipid bilayer-membrane scaffold protein complexes encompassing the human TMB2 protein were generated using Bir-A labeled membrane scaffold proteins, and purified as described in Example 8.

Additionally, a nucleotide sequence encoding the His tag and a nucleotide sequence encoding the FLAG tag affixed to the modified human TMB2 protein were generated, expressed separately in cells and purified as set forth in Example 1 to provide a FLAG-peptide and HIS-peptide, respectively. Next, a nucleotide sequence encoding the membrane scaffold protein included in the lipid bilayer-membrane scaffold protein complexes was generated, expressed separately in cells and purified as set forth in Example 1 to provide an MSP-peptide.

As demonstrated in Table 5, genetically-engineered VELOCIMMUNE® mice including DNA encoding human immunoglobulin heavy (IgH) and human immunoglobulin light chain variable regions, which do not express the endogenous mouse homolog to the transmembrane protein of interest (i.e, mouse TMB2) were immunized by injection of 0.54 mg/mL lipid bilayer-membrane scaffold protein complexes encompassing the human TMB2 protein (complex w/human TMB2). Immune response was monitored, and splenocytes were harvested from the immunized mice. The splenocytes collected from each immunized mouse were stained with fluorescent labels to B cell markers (i.e., anti-IgG antibody) and at the same time incubated with the MSP-peptide, FLAG-peptide and HIS-peptide to permit binding between the MSP-peptide, FLAG-peptide and HIS-peptide and antibody on the surface of B cells that are specific to an epitope located on the MSP-peptide, FLAG-peptide and HIS-peptide, respectively. This step effectively blocks all antibody-producing B cells that express antibody specific to elements of the complex other than the human TMB2 protein presented by the complex.

Subsequently, the remaining B cells were incubated with biotinylated lipid bilayer-membrane scaffold protein complexes including either a human TMB2 protein (Complex w/human TMB2) or a mouse TMB2 protein (Complex w/mouse TMB2) to permit binding between the transmembrane protein of interest presented by the biotinylated lipid bilayer-membrane scaffold protein complex and an antibody on the surface of a B cell. Cells were then washed to remove unbound complex and incubated with PE-streptavidin to enable streptavidin binding to each of the biotin (Bir-A) labeled membrane scaffold proteins in the lipid bilayer-membrane scaffold protein complex. Cells were then washed in phosphate buffered saline (PBS) to remove excess PE-streptavidin from the sort. PE fluorescence of cell populations collected from the mice were detected by FACS to identify a population of antibody-producing B cells that express antibodies specific to the transmembrane protein of interest.

Single antibody-producing B cells that bound to the transmembrane protein of interest were then isolated to individual wells on 384-well plates, antibody encoding DNA was isolated from each cell, and antibodies were generated as set forth in Example 2 for further analysis.

As shown in Table 5, immunization of genetically modified mice with lipid bilayer-membrane scaffold protein complex encompassing the human TMB2 protein and sorting of antibody-producing B cells with a lipid bilayer-membrane scaffold protein complex presenting human TMB2 protein, identified antibody producing B cells that express cross-reactive antibody capable of binding the mouse TMB2 and the human TMB2 protein homologs, as well as antibody specific to the human TMB2 protein. In addition, immunization of genetically modified mice with lipid bilayer-membrane scaffold protein complex encompassing the human TMB2 protein and sorting of antibody-producing B cells with al lipid bilayer-membrane scaffold protein complex presenting mouse TMB2 protein, identified antibody producing B cells that express only cross-reactive antibody capable of binding the mouse TMB2 protein and the human TMB2 protein.

Example 10. Generating Antibody Producing Cells that Express Antibody that Binds to an Exemplary SLC Transmembrane Protein of Interest, and Obtaining SLC Protein Specific Antibodies from the Cells The nucleotide sequence encoding a first exemplary SLC transmembrane protein of interest is modified as set forth in Example 1 to include a FLAG tag and a 10×-His tag affixed to the N terminal of the exemplary SLC protein. The nucleotide sequence encoding the modified SLC transmembrane protein is cloned into an expression vector and expressed in Sf9 cells. The cells are then solubilized, and modified SLC transmembrane proteins are obtained and purified as described in Example 1.

Next, discoidal lipid-bilayer membrane scaffold protein complexes containing modified human SLC transmembrane protein are generated as set forth in Example 1 and herein.

Genetically modified SLC knock-out mice, i.e., VELOCIMMUNE® mouse including a humanized IgH locus and a humanized Igκ locus that also lack the endogenous mouse gene encoding the SLC transmembrane protein of interest, are immunized by injection of exogenous DNA encoding the modified human SLC protein and injection of the modified human SLC protein as described in Example 1.

Splenocytes are collected from each immunized mouse and stained with fluorescent labels to B cell markers (i.e., anti-IgG antibody) and at the same time incubated with 0.2 mg/ml to 5.0 mg/mL biotinylated lipid bilayer-membrane scaffold protein complex containing a SLC transmembrane protein embedded therein. Cells are then washed to remove unbound complex. Subsequently, cells are incubated with PE-streptavidin to enable streptavidin binding to each of the biotin (Bir-A) labeled membrane scaffold proteins in the lipid-bilayer-membrane scaffold protein complex. Cells are then washed in phosphate buffered saline (PBS) to remove excess PE-streptavidin. PE fluorescence of cell populations from control mice and immunized mice is detected by FACS to identify a population of B cells that express antibodies that bind to the exemplary SLC transmembrane protein of interest presented by a biotinylated lipid bilayer-membrane scaffold protein complex.

Single antibody-producing B cells that bound to the SLC transmembrane protein of interest are then isolated to individual wells on 384-well plates, antibody-encoding DNA is isolated from each cell, and antibodies are generated as set forth in Example 2 for further analysis.

While several aspects of the present disclosure have been described and depicted herein, alternative aspects may be affected by those skilled in the art to accomplish the same objectives. Accordingly, it is intended by the appended claims to cover all such alternative aspects as fall within the true spirit and scope of the disclosure.

TABLE 5

| Mouse | Immunogen | Antigen Presentation Strategy | Total # Antibody-producing cells collected | # Antibody-producing cells analyzed | # Antibodies Tested | # Antigen Binding Antibodies | % Antibody that Bind Antigen |
|---|---|---|---|---|---|---|---|
| VI-KO | Complex w/ Human TMB2 | Complex w/ Human TMB2 | 1370 | 666 | 116 | 32 | 28 |
| VI-KO | Complex w/ Human TMB2 | Complex w/ mouse TMB2 | 102 | 102 | 78 | 10 | 13 |

What is claimed is:

1. A method for obtaining an antibody-producing cell that expresses an antibody that binds to a transmembrane protein of interest, the method comprising:
   (a) contacting a population of antibody-producing cells with a lipid bilayer-membrane scaffold protein complex comprising the transmembrane protein of interest and with at least one blocking agent, to permit the transmembrane protein of interest to bind to an antibody expressed on the cell surface; and
   (b) collecting cells bound to the transmembrane protein of interest.

2. The method of claim 1, wherein the complex comprises a plurality of lipids that form a discoidal phospholipid bilayer surrounded by at least one membrane scaffold protein.

3. The method of claim 1, wherein the population of antibody-producing cells are obtained from spleen, lymph node, peripheral blood, bone marrow, or a combination thereof.

4. The method of claim 1, wherein the population of antibody-producing cells comprises peripheral blood cells, B cells, plasma cells, plasma cell myelomas, or a combination thereof.

5. The method of claim 4, wherein the population of antibody-producing cells comprises B-cells.

6. The method of claim 1, wherein the antibody-producing cells are obtained from a mammal previously immunized to the transmembrane protein of interest.

7. The method of claim 6, wherein the mammal is a non-human mammal that has been immunized with a nucleic acid encoding at least a portion of the transmembrane protein of interest, or with at least a portion of the transmembrane protein of interest.

8. The method of claim 7, wherein the non-human mammal is genetically-engineered and does not express the transmembrane protein of interest from an endogenous gene.

9. The method of claim 8, wherein the genetically-engineered non-human mammal comprises a nucleic acid sequence encoding a human heavy chain variable region and a nucleic acid sequence encoding a human light chain variable region.

10. The method of claim 8, wherein the genetically-engineered non-human mammal is a mouse.

11. The method of claim 8, wherein said transmembrane protein of interest is a human transmembrane protein.

12. The method of claim 11, wherein the genetically-engineered non-human mammal has been immunized with a non-human homolog of the transmembrane protein or a nucleic acid encoding the non-human homolog of the transmembrane protein.

13. The method of claim 12, wherein the cells collected in step (b) express an antibody that binds to the human transmembrane protein and the non-human homolog of the transmembrane protein.

14. The method of claim 11, wherein the genetically-engineered non-human mammal has been immunized with a chimeric transmembrane protein of interest or a nucleic acid encoding the chimeric transmembrane protein of interest, and wherein the chimeric transmembrane protein comprises a portion of a non-human homolog of the transmembrane protein of interest and a portion of the human transmembrane protein.

15. The method of claim 14, wherein the cells collected in step (b) express an antibody that binds to an epitope located on the human transmembrane protein.

16. The method of claim 8, wherein the transmembrane protein of interest is a chimeric transmembrane protein, wherein the chimeric protein comprises a portion of a human transmembrane protein operably linked to a portion of a non-human transmembrane protein.

17. The method of claim 16, wherein the genetically-engineered non-human mammal has been immunized with the human transmembrane protein or a nucleic acid encoding the human transmembrane protein.

18. The method of claim 17, wherein the cells collected in step (b) express an antibody that binds to the human portion of the chimeric transmembrane protein.

19. The method of claim 8, wherein the genetically-engineered non-human mammal has been immunized with a truncated form of the transmembrane protein, or with the full-length form of the transmembrane protein or a nucleic acid encoding the same.

20. The method of claim 19, wherein the truncated form of the transmembrane protein does not contain an N-terminal domain or a C-terminal domain of the full-length form of the transmembrane protein.

21. The method of claim 20, wherein the truncated form of the transmembrane protein comprises an extracellular loop, and wherein the cells collected in step (b) express an antibody that binds to an epitope located on the extracellular loop of the truncated form of the transmembrane protein.

22. The method of claim 1, wherein the at least one blocking agent is a polypeptide that binds to a portion of the transmembrane protein of interest.

23. The method of claim 22, wherein the polypeptide binds to an N-terminal domain of the transmembrane protein of interest or a C-terminal domain of the transmembrane protein of interest.

24. The method of claim 23, wherein the transmembrane protein comprises an extracellular loop, and wherein the cells collected in step (b) express an antibody that binds to an epitope located on the extracellular loop of the transmembrane protein of interest.

25. The method of claim 1, wherein the population of antibody-producing cells are obtained from a mammal that has been immunized with said lipid bilayer-membrane scaffold protein complex comprising the transmembrane protein of interest, wherein the complex further comprises a first detectable label, and wherein the transmembrane protein of interest comprises a second detectable label.

26. The method of claim 25, wherein the at least one blocking agent comprises (i) a first blocking agent that binds to said first detectable label and (ii) a second blocking agent that binds to said second detectable label.

27. The method of claim 26, wherein the at least one blocking agent comprises a third blocking agent that binds to the membrane scaffold protein.

28. The method of claim 1, wherein the transmembrane protein of interest is selected from the group consisting of a G-protein Coupled Receptor (GPCR) protein, a tetraspanin protein, and an ion channel protein.

29. The method of claim 1, wherein the complex further comprises at least one membrane scaffold protein that is conjugated to a detectable label.

30. The method of claim 29, wherein collecting the cells bound to the transmembrane protein of interest comprises:
    detecting binding of the cells to the transmembrane protein of interest;
    separating the cells bound to the transmembrane protein of interest from cells that are not bound to the transmembrane protein of interest; and
    collecting the bound cells.

31. The method of claim 30, wherein the detectable label is biotin.

32. The method of claim 31, wherein said detecting comprises:
    incubating the cells of step (b) with streptavidin-phycoerythrin (PE-streptavidin); and
    identifying the bound cells using fluorescence-activated cell sorting (FACS).

33. The method of claim 30, wherein the detectable label is a fluorescent molecule.

34. The method of claim 33, wherein said detecting comprises identifying the bound cells using FACS.

35. The method of claim 1, further comprising (i) isolating from a cell of the cell collected in step (b), a nucleic acid comprising a nucleotide sequence encoding the heavy chain variable region of the antibody expressed by the cell, and a nucleic acid comprising a nucleotide sequence encoding the light chain variable region of the antibody expressed by the cell.

36. The method of claim 35, wherein the method further comprises, after step (i):
    (ii) transfecting a host mammalian cell to introduce the nucleic acid comprising the nucleotide sequence encoding the heavy chain variable region, and the nucleic acid comprising the nucleotide sequence encoding the light chain variable region isolated in step (i); and
    (iii) culturing the host mammalian cell from step (ii) under conditions that express an antibody comprising the heavy chain variable region and the light chain variable region.

37. The method of claim 36, wherein the host cell in step (ii) is transfected with a first expression vector comprising the nucleotide sequence encoding the heavy chain variable region, and a second expression vector comprising the nucleotide sequence encoding the light chain variable region.

38. The method of claim 36, wherein the mammalian cell is a Chinese hamster ovary (CHO) cell.

39. The method according to claim 1, wherein the lipid bilayer-membrane scaffold protein complex comprising the transmembrane protein of interest is formed by mixing lipids, a membrane scaffold protein, and the transmembrane protein of interest provided in the presence of one or more detergents, and removing the one or more detergents to induce the formation of the complex comprising the transmembrane protein of interest.

* * * * *

UNITED STATES PATENT AND TRADEMARK OFFICE
CERTIFICATE OF CORRECTION

PATENT NO. : 12,371,487 B2
APPLICATION NO. : 17/558645
DATED : July 29, 2025
INVENTOR(S) : Gang Chen et al.

Page 1 of 1

It is certified that error appears in the above-identified patent and that said Letters Patent is hereby corrected as shown below:

In the Claims

Column 100, Claim 35, Line 6 should read:
from a cell of the cells collected in step (b), a nucleic acid Signed and Sealed this
Second Day of September, 2025

Coke Morgan Stewart
*Acting Director of the United States Patent and Trademark Office*

SEQUENCE LISTING

<160> NUMBER OF SEQ ID NOS: 24

<210> SEQ ID NO 1
<211> LENGTH: 12
<212> TYPE: PRT
<213> ORGANISM: Artificial Sequence
<220> FEATURE:
<223> OTHER INFORMATION: synthetic peptide

<400> SEQUENCE: 1

Met Gly His His His His His His Ile Glu Gly Arg
1               5                   10

<210> SEQ ID NO 2
<211> LENGTH: 22
<212> TYPE: PRT
<213> ORGANISM: Artificial Sequence
<220> FEATURE:
<223> OTHER INFORMATION: synthetic peptide

<400> SEQUENCE: 2

Leu Lys Leu Leu Asp Asn Trp Asp Ser Val Thr Ser Thr Phe Ser Lys
1               5                   10                  15

Leu Arg Glu Gln Leu Gly
            20

<210> SEQ ID NO 3
<211> LENGTH: 22
<212> TYPE: PRT
<213> ORGANISM: Artificial Sequence
<220> FEATURE:
<223> OTHER INFORMATION: synthetic peptide

<400> SEQUENCE: 3

Pro Val Thr Gln Glu Phe Trp Asp Asn Leu Glu Lys Glu Thr Glu Gly
1               5                   10                  15

Leu Arg Gln Glu Met Ser
            20

<210> SEQ ID NO 4
<211> LENGTH: 11
<212> TYPE: PRT
<213> ORGANISM: Artificial Sequence
<220> FEATURE:
<223> OTHER INFORMATION: synthetic peptide

<400> SEQUENCE: 4

Lys Asp Leu Glu Glu Val Lys Ala Lys Val Gln
1               5                   10

<210> SEQ ID NO 5
<211> LENGTH: 22
<212> TYPE: PRT
<213> ORGANISM: Artificial Sequence
<220> FEATURE:
<223> OTHER INFORMATION: synthetic peptide

<400> SEQUENCE: 5

Pro Tyr Leu Asp Asp Phe Gln Lys Lys Trp Gln Glu Glu Met Glu Leu
1               5                   10                  15

Tyr Arg Gln Lys Val Glu
            20

<210> SEQ ID NO 6
<211> LENGTH: 22

```
<212> TYPE: PRT
<213> ORGANISM: Artificial Sequence
<220> FEATURE:
<223> OTHER INFORMATION: synthetic peptide

<400> SEQUENCE: 6

Pro Leu Arg Ala Glu Leu Gln Glu Gly Ala Arg Gln Lys Leu His Glu
1               5                   10                  15

Leu Gln Glu Lys Leu Ser
            20

<210> SEQ ID NO 7
<211> LENGTH: 22
<212> TYPE: PRT
<213> ORGANISM: Artificial Sequence
<220> FEATURE:
<223> OTHER INFORMATION: synthetic peptide

<400> SEQUENCE: 7

Pro Leu Gly Glu Glu Met Arg Asp Arg Ala Arg Ala His Val Asp Ala
1               5                   10                  15

Leu Arg Thr His Leu Ala
            20

<210> SEQ ID NO 8
<211> LENGTH: 22
<212> TYPE: PRT
<213> ORGANISM: Artificial Sequence
<220> FEATURE:
<223> OTHER INFORMATION: synthetic peptide

<400> SEQUENCE: 8

Pro Tyr Ser Asp Glu Leu Arg Gln Arg Leu Ala Ala Arg Leu Glu Ala
1               5                   10                  15

Leu Lys Glu Asn Gly Gly
            20

<210> SEQ ID NO 9
<211> LENGTH: 22
<212> TYPE: PRT
<213> ORGANISM: Artificial Sequence
<220> FEATURE:
<223> OTHER INFORMATION: synthetic peptide

<400> SEQUENCE: 9

Ala Arg Leu Ala Glu Tyr His Ala Lys Ala Thr Glu His Leu Ser Thr
1               5                   10                  15

Leu Ser Glu Lys Ala Lys
            20

<210> SEQ ID NO 10
<211> LENGTH: 11
<212> TYPE: PRT
<213> ORGANISM: Artificial Sequence
<220> FEATURE:
<223> OTHER INFORMATION: synthetic peptide

<400> SEQUENCE: 10

Pro Ala Leu Glu Asp Leu Arg Gln Gly Leu Leu
1               5                   10

<210> SEQ ID NO 11
<211> LENGTH: 24
<212> TYPE: PRT
<213> ORGANISM: Artificial Sequence
```

<220> FEATURE:
<223> OTHER INFORMATION: synthetic peptide

<400> SEQUENCE: 11

Pro Val Leu Glu Ser Phe Lys Val Ser Phe Leu Ser Ala Leu Glu Glu
1               5                   10                  15

Tyr Thr Lys Lys Leu Asn Thr Gln
            20

<210> SEQ ID NO 12
<211> LENGTH: 212
<212> TYPE: PRT
<213> ORGANISM: Artificial Sequence
<220> FEATURE:
<223> OTHER INFORMATION: synthetic peptide

<400> SEQUENCE: 12

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln
    210

<210> SEQ ID NO 13
<211> LENGTH: 414
<212> TYPE: PRT
<213> ORGANISM: Artificial Sequence
<220> FEATURE:
<223> OTHER INFORMATION: synthetic peptide

<400> SEQUENCE: 13

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
             35                  40                  45

Glu Gly Leu Arg Gln Glu Met Ser Lys Asp Leu Glu Glu Val Lys Ala
 50                  55                  60

Lys Val Gln Pro Tyr Leu Asp Asp Phe Gln Lys Lys Trp Gln Glu Glu
 65                  70                  75                  80

Met Glu Leu Tyr Arg Gln Lys Val Glu Pro Leu Arg Ala Glu Leu Gln
                 85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
            115                 120                 125

Arg Thr His Leu Ala Pro Tyr Ser Asp Glu Leu Arg Gln Arg Leu Ala
130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
            195                 200                 205

Leu Asn Thr Gln Gly Thr Leu Lys Leu Leu Asp Asn Trp Asp Ser Val
210                 215                 220

Thr Ser Thr Phe Ser Lys Leu Arg Glu Gln Leu Gly Pro Val Thr Gln
225                 230                 235                 240

Glu Phe Trp Asp Asn Leu Glu Lys Glu Thr Glu Gly Leu Arg Gln Glu
                245                 250                 255

Met Ser Lys Asp Leu Glu Glu Val Lys Ala Lys Val Gln Pro Tyr Leu
            260                 265                 270

Asp Asp Phe Gln Lys Lys Trp Gln Glu Glu Met Glu Leu Tyr Arg Gln
            275                 280                 285

Lys Val Glu Pro Leu Arg Ala Glu Leu Gln Glu Gly Ala Arg Gln Lys
            290                 295                 300

Leu His Glu Leu Gln Glu Lys Leu Ser Pro Leu Gly Glu Glu Met Arg
305                 310                 315                 320

Asp Arg Ala Arg Ala His Val Asp Ala Leu Arg Thr His Leu Ala Pro
                325                 330                 335

Tyr Ser Asp Glu Leu Arg Gln Arg Leu Ala Ala Arg Leu Glu Ala Leu
            340                 345                 350

Lys Glu Asn Gly Gly Ala Arg Leu Ala Glu Tyr His Ala Lys Ala Thr
            355                 360                 365

Glu His Leu Ser Thr Leu Ser Glu Lys Ala Lys Pro Ala Leu Glu Asp
            370                 375                 380

Leu Arg Gln Gly Leu Leu Pro Val Leu Glu Ser Phe Lys Val Ser Phe
385                 390                 395                 400

Leu Ser Ala Leu Glu Glu Tyr Thr Lys Lys Leu Asn Thr Gln
                405                 410

<210> SEQ ID NO 14
<211> LENGTH: 234
<212> TYPE: PRT
<213> ORGANISM: Artificial Sequence
<220> FEATURE:
<223> OTHER INFORMATION: synthetic peptide

<400> SEQUENCE: 14

Met Gly His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Tyr Leu Asp Asp Phe Gln
                85                  90                  95

Lys Lys Trp Gln Glu Glu Met Glu Leu Tyr Arg Gln Lys Val Glu Pro
            100                 105                 110

Leu Arg Ala Glu Leu Gln Glu Gly Ala Arg Gln Lys Leu His Glu Leu
        115                 120                 125

Gln Glu Lys Leu Ser Pro Leu Gly Glu Glu Met Arg Asp Arg Ala Arg
    130                 135                 140

Ala His Val Asp Ala Leu Arg Thr His Leu Ala Pro Tyr Ser Asp Glu
145                 150                 155                 160

Leu Arg Gln Arg Leu Ala Ala Arg Leu Glu Ala Leu Lys Glu Asn Gly
                165                 170                 175

Gly Ala Arg Leu Ala Glu Tyr His Ala Lys Ala Thr Glu His Leu Ser
            180                 185                 190

Thr Leu Ser Glu Lys Ala Lys Pro Ala Leu Glu Asp Leu Arg Gln Gly
        195                 200                 205

Leu Leu Pro Val Leu Glu Ser Phe Lys Val Ser Phe Leu Ser Ala Leu
    210                 215                 220

Glu Glu Tyr Thr Lys Lys Leu Asn Thr Gln
225                 230

<210> SEQ ID NO 15
<211> LENGTH: 256
<212> TYPE: PRT
<213> ORGANISM: Artificial Sequence
<220> FEATURE:
<223> OTHER INFORMATION: synthetic peptide

<400> SEQUENCE: 15

Met Gly His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

```
Tyr Leu Asp Asp Phe Gln Lys Lys Trp Gln Glu Glu Met Glu Leu Tyr
            115                 120                 125

Arg Gln Lys Val Glu Pro Leu Arg Ala Glu Leu Gln Glu Gly Ala Arg
        130                 135                 140

Gln Lys Leu His Glu Leu Gln Glu Lys Leu Ser Pro Leu Gly Glu Glu
145                 150                 155                 160

Met Arg Asp Arg Ala Arg Ala His Val Asp Ala Leu Arg Thr His Leu
                165                 170                 175

Ala Pro Tyr Ser Asp Glu Leu Arg Gln Arg Leu Ala Ala Arg Leu Glu
            180                 185                 190

Ala Leu Lys Glu Asn Gly Gly Ala Arg Leu Ala Glu Tyr His Ala Lys
        195                 200                 205

Ala Thr Glu His Leu Ser Thr Leu Ser Glu Lys Ala Lys Pro Ala Leu
    210                 215                 220

Glu Asp Leu Arg Gln Gly Leu Leu Pro Val Leu Glu Ser Phe Lys Val
225                 230                 235                 240

Ser Phe Leu Ser Ala Leu Glu Glu Tyr Thr Lys Lys Leu Asn Thr Gln
                245                 250                 255

<210> SEQ ID NO 16
<211> LENGTH: 278
<212> TYPE: PRT
<213> ORGANISM: Artificial Sequence
<220> FEATURE:
<223> OTHER INFORMATION: synthetic peptide

<400> SEQUENCE: 16

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Leu Asp Asp Phe Gln Lys Lys Trp Gln
    130                 135                 140

Glu Glu Met Glu Leu Tyr Arg Gln Lys Val Glu Pro Leu Arg Ala Glu
145                 150                 155                 160

Leu Gln Glu Gly Ala Arg Gln Lys Leu His Glu Leu Gln Glu Lys Leu
                165                 170                 175

Ser Pro Leu Gly Glu Glu Met Arg Asp Arg Ala Arg Ala His Val Asp
            180                 185                 190

Ala Leu Arg Thr His Leu Ala Pro Tyr Ser Asp Glu Leu Arg Gln Arg
        195                 200                 205

Leu Ala Ala Arg Leu Glu Ala Leu Lys Glu Asn Gly Gly Ala Arg Leu
    210                 215                 220
```

```
Ala Glu Tyr His Ala Lys Ala Thr Glu His Leu Ser Thr Leu Ser Glu
225                 230                 235                 240

Lys Ala Lys Pro Ala Leu Glu Asp Leu Arg Gln Gly Leu Leu Pro Val
                245                 250                 255

Leu Glu Ser Phe Lys Val Ser Phe Leu Ser Ala Leu Glu Glu Tyr Thr
            260                 265                 270

Lys Lys Leu Asn Thr Gln
        275

<210> SEQ ID NO 17
<211> LENGTH: 212
<212> TYPE: PRT
<213> ORGANISM: Artificial Sequence
<220> FEATURE:
<223> OTHER INFORMATION: synthetic peptide

<400> SEQUENCE: 17

Met Gly His His His His His His Asp Tyr Asp Ile Pro Thr Thr
1               5                   10                  15

Glu Asn Leu Tyr Phe Gln Gly Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln
    210

<210> SEQ ID NO 18
<211> LENGTH: 23
<212> TYPE: PRT
<213> ORGANISM: Artificial Sequence
<220> FEATURE:
<223> OTHER INFORMATION: synthetic peptide

<400> SEQUENCE: 18

Met Gly His His His His His His Asp Tyr Asp Ile Pro Thr Thr
1               5                   10                  15

Glu Asn Leu Tyr Phe Gln Gly
            20
```

```
<210> SEQ ID NO 19
<211> LENGTH: 11
<212> TYPE: PRT
<213> ORGANISM: Artificial Sequence
<220> FEATURE:
<223> OTHER INFORMATION: synthetic peptide

<400> SEQUENCE: 19

Ser Thr Phe Ser Lys Leu Arg Glu Gln Leu Gly
1               5                   10

<210> SEQ ID NO 20
<211> LENGTH: 201
<212> TYPE: PRT
<213> ORGANISM: Artificial Sequence
<220> FEATURE:
<223> OTHER INFORMATION: synthetic peptide

<400> SEQUENCE: 20

Met Gly His His His His His His Asp Tyr Asp Ile Pro Thr Thr
1               5                   10                  15

Glu Asn Leu Tyr Phe Gln Gly Pro Val Thr Gln Glu Phe Trp Asp Asn
            20                  25                  30

Leu Glu Lys Glu Thr Glu Gly Leu Arg Gln Glu Met Ser Lys Asp Leu
        35                  40                  45

Glu Glu Val Lys Ala Lys Val Gln Pro Tyr Leu Asp Asp Phe Gln Lys
    50                  55                  60

Lys Trp Gln Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
            180                 185                 190

Glu Tyr Thr Lys Lys Leu Asn Thr Gln
        195                 200

<210> SEQ ID NO 21
<211> LENGTH: 403
<212> TYPE: PRT
<213> ORGANISM: Artificial Sequence
<220> FEATURE:
<223> OTHER INFORMATION: synthetic peptide

<400> SEQUENCE: 21

Met Gly His His His His His His Asp Tyr Asp Ile Pro Thr Thr
1               5                   10                  15

Glu Asn Leu Tyr Phe Gln Gly Ser Thr Phe Ser Lys Leu Arg Glu Gln
            20                  25                  30
```

```
Leu Gly Pro Val Thr Gln Glu Phe Trp Asp Asn Leu Glu Lys Glu Thr
         35                  40                  45

Glu Gly Leu Arg Gln Glu Met Ser Lys Asp Leu Glu Glu Val Lys Ala
 50                  55                  60

Lys Val Gln Pro Tyr Leu Asp Asp Phe Gln Lys Lys Trp Gln Glu Glu
 65                  70                  75                  80

Met Glu Leu Tyr Arg Gln Lys Val Glu Pro Leu Arg Ala Glu Leu Gln
                 85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
            115                 120                 125

Arg Thr His Leu Ala Pro Tyr Ser Asp Glu Leu Arg Gln Arg Leu Ala
130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
            195                 200                 205

Leu Asn Thr Gln Gly Thr Ser Thr Phe Ser Lys Leu Arg Glu Gln Leu
210                 215                 220

Gly Pro Val Thr Gln Glu Phe Trp Asp Asn Leu Glu Lys Glu Thr Glu
225                 230                 235                 240

Gly Leu Arg Gln Glu Met Ser Lys Asp Leu Glu Glu Val Lys Ala Lys
                245                 250                 255

Val Gln Pro Tyr Leu Asp Asp Phe Gln Lys Lys Trp Gln Glu Glu Met
            260                 265                 270

Glu Leu Tyr Arg Gln Lys Val Glu Pro Leu Arg Ala Glu Leu Gln Glu
            275                 280                 285

Gly Ala Arg Gln Lys Leu His Glu Leu Gln Glu Lys Leu Ser Pro Leu
290                 295                 300

Gly Glu Glu Met Arg Asp Arg Ala Arg Ala His Val Asp Ala Leu Arg
305                 310                 315                 320

Thr His Leu Ala Pro Tyr Ser Asp Glu Leu Arg Gln Arg Leu Ala Ala
                325                 330                 335

Arg Leu Glu Ala Leu Lys Glu Asn Gly Gly Ala Arg Leu Ala Glu Tyr
            340                 345                 350

His Ala Lys Ala Thr Glu His Leu Ser Thr Leu Ser Glu Lys Ala Lys
            355                 360                 365

Pro Ala Leu Glu Asp Leu Arg Gln Gly Leu Leu Pro Val Leu Glu Ser
            370                 375                 380

Phe Lys Val Ser Phe Leu Ser Ala Leu Glu Glu Tyr Thr Lys Lys Leu
385                 390                 395                 400

Asn Thr Gln
```

<210> SEQ ID NO 22
<211> LENGTH: 392
<212> TYPE: PRT
<213> ORGANISM: Artificial Sequence
<220> FEATURE:
<223> OTHER INFORMATION: synthetic peptide

<400> SEQUENCE: 22

```
Met Gly His His His His His His Asp Tyr Asp Ile Pro Thr Thr
1               5                   10                  15

Glu Asn Leu Tyr Phe Gln Gly Ser Thr Phe Ser Lys Leu Arg Glu Gln
            20                  25                  30

Leu Gly Pro Val Thr Gln Glu Phe Trp Asp Asn Leu Glu Lys Glu Thr
            35                  40                  45

Glu Gly Leu Arg Gln Glu Met Ser Lys Asp Leu Glu Glu Val Lys Ala
        50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln Gly Thr Pro Val Thr Gln Glu Phe Trp Asp Asn Leu
    210                 215                 220

Glu Lys Glu Thr Glu Gly Leu Arg Gln Glu Met Ser Lys Asp Leu Glu
225                 230                 235                 240

Glu Val Lys Ala Lys Val Gln Pro Tyr Leu Asp Asp Phe Gln Lys Lys
                245                 250                 255

Trp Gln Glu Glu Met Glu Leu Tyr Arg Gln Lys Val Glu Pro Leu Arg
            260                 265                 270

Ala Glu Leu Gln Glu Gly Ala Arg Gln Lys Leu His Glu Leu Gln Glu
        275                 280                 285

Lys Leu Ser Pro Leu Gly Glu Glu Met Arg Asp Arg Ala Arg Ala His
    290                 295                 300

Val Asp Ala Leu Arg Thr His Leu Ala Pro Tyr Ser Asp Glu Leu Arg
305                 310                 315                 320

Gln Arg Leu Ala Ala Arg Leu Glu Ala Leu Lys Glu Asn Gly Gly Ala
                325                 330                 335

Arg Leu Ala Glu Tyr His Ala Lys Ala Thr Glu His Leu Ser Thr Leu
            340                 345                 350

Ser Glu Lys Ala Lys Pro Ala Leu Glu Asp Leu Arg Gln Gly Leu Leu
        355                 360                 365

Pro Val Leu Glu Ser Phe Lys Val Ser Phe Leu Ser Ala Leu Glu Glu
    370                 375                 380

Tyr Thr Lys Lys Leu Asn Thr Gln
385                 390
```

<210> SEQ ID NO 23

```
<211> LENGTH: 5
<212> TYPE: PRT
<213> ORGANISM: Artificial Sequence
<220> FEATURE:
<223> OTHER INFORMATION: synthetic peptide

<400> SEQUENCE: 23

Arg Glu Gln Leu Gly
1               5

<210> SEQ ID NO 24
<211> LENGTH: 397
<212> TYPE: PRT
<213> ORGANISM: Artificial Sequence
<220> FEATURE:
<223> OTHER INFORMATION: synthetic peptide

<400> SEQUENCE: 24

Met Gly His His His His His His Asp Tyr Asp Ile Pro Thr Thr
1               5                   10                  15

Glu Asn Leu Tyr Phe Gln Gly Ser Thr Phe Ser Lys Leu Arg Glu Gln
                20                  25                  30

Leu Gly Pro Val Thr Gln Glu Phe Trp Asp Asn Leu Glu Lys Glu Thr
            35                  40                  45

Glu Gly Leu Arg Gln Glu Met Ser Lys Asp Leu Glu Glu Val Lys Ala
50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln Gly Thr Arg Glu Gln Leu Gly Pro Val Thr Gln Glu
    210                 215                 220

Phe Trp Asp Asn Leu Glu Lys Glu Thr Glu Gly Leu Arg Gln Glu Met
225                 230                 235                 240

Ser Lys Asp Leu Glu Glu Val Lys Ala Lys Val Gln Pro Tyr Leu Asp
                245                 250                 255

Asp Phe Gln Lys Lys Trp Gln Glu Glu Met Glu Leu Tyr Arg Gln Lys
            260                 265                 270

Val Glu Pro Leu Arg Ala Glu Leu Gln Glu Gly Ala Arg Gln Lys Leu
        275                 280                 285

His Glu Leu Gln Glu Lys Leu Ser Pro Leu Gly Glu Glu Met Arg Asp
    290                 295                 300

Arg Ala Arg Ala His Val Asp Ala Leu Arg Thr His Leu Ala Pro Tyr
```

-continued

```
305                 310                 315                 320
Ser Asp Glu Leu Arg Gln Arg Leu Ala Ala Arg Leu Glu Ala Leu Lys
                325                 330                 335

Glu Asn Gly Gly Ala Arg Leu Ala Glu Tyr His Ala Lys Ala Thr Glu
            340                 345                 350

His Leu Ser Thr Leu Ser Glu Lys Ala Lys Pro Ala Leu Glu Asp Leu
        355                 360                 365

Arg Gln Gly Leu Leu Pro Val Leu Glu Ser Phe Lys Val Ser Phe Leu
    370                 375                 380

Ser Ala Leu Glu Glu Tyr Thr Lys Lys Leu Asn Thr Gln
385                 390                 395
```